(12) United States Patent
Todd et al.

(10) Patent No.: US 9,127,311 B2
(45) Date of Patent: Sep. 8, 2015

(54) MOLECULAR SWITCHES AND METHODS FOR THEIR USE

(75) Inventors: Alison Velyian Todd, Glebe (AU); Elisa Mokany, Woolooware (AU); Donald John Birkett, Mosman (AU); Tram Bich Doan, Fairfield West (AU); Christopher Roland Reid, Dulwich Hill (AU)

(73) Assignee: SpeeDx Pty Ltd (AU)

( * ) Notice: Subject to any disclaimer, the term of this patent is extended or adjusted under 35 U.S.C. 154(b) by 586 days.

(21) Appl. No.: 12/442,275

(22) PCT Filed: Oct. 5, 2007

(86) PCT No.: PCT/AU2007/001517
§ 371 (c)(1),
(2), (4) Date: Aug. 26, 2009

(87) PCT Pub. No.: WO2008/040095
PCT Pub. Date: Apr. 10, 2008

(65) Prior Publication Data
US 2010/0136536 A1 Jun. 3, 2010

Related U.S. Application Data

(60) Provisional application No. 60/828,451, filed on Oct. 6, 2006.

(51) Int. Cl.
C12Q 1/68 (2006.01)
C07H 21/04 (2006.01)
C12N 15/11 (2006.01)

(52) U.S. Cl.
CPC .............. *C12Q 1/6818* (2013.01); *C12Q 1/682* (2013.01)

(58) Field of Classification Search
None
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 4,800,159 A | 1/1989 | Mullis et al. | |
| 4,965,188 A | 10/1990 | Mullis et al. | |
| 5,176,995 A | 1/1993 | Sninsky et al. | |
| 5,545,729 A * | 8/1996 | Goodchild et al. | 536/24.5 |
| 5,589,332 A | 12/1996 | Shih et al. | |
| 5,807,718 A | 9/1998 | Joyce et al. | |
| 5,876,924 A | 3/1999 | Zhang et al. | |
| 6,140,055 A | 10/2000 | Todd et al. | |
| 6,201,113 B1 | 3/2001 | Todd et al. | |
| 6,326,174 B1 | 12/2001 | Joyce et al. | |
| 6,365,724 B2 | 4/2002 | Todd et al. | |
| 6,451,535 B1 | 9/2002 | Jenne et al. | |
| 6,861,223 B2 * | 3/2005 | Jenne et al. | 435/6.1 |
| 7,141,665 B1 | 11/2006 | Joyce et al. | |
| 7,553,945 B2 * | 6/2009 | Leontis | 536/23.1 |
| 8,354,227 B2 * | 1/2013 | Kolpashchikov | 435/6.1 |
| 2002/0102568 A1 | 8/2002 | Usman et al. | |
| 2003/0013095 A1 * | 1/2003 | Taira et al. | 435/6 |
| 2007/0231810 A1 | 10/2007 | Todd et al. | |
| 2010/0221711 A1 | 9/2010 | Nauwelaers et al. | |
| 2011/0143338 A1 | 6/2011 | Todd et al. | |
| 2013/0123480 A1 | 5/2013 | Todd et al. | |

FOREIGN PATENT DOCUMENTS

| | | |
|---|---|---|
| AU | PI 5911 | 12/1987 |
| AU | 199959817 B2 | 10/2000 |
| EP | 0 552 931 A1 | 7/1993 |
| EP | 1 063 296 A1 | 12/2000 |
| WO | WO 96/17086 A1 | 6/1996 |
| WO | WO 96/27026 A1 | 9/1996 |
| WO | WO 98/49346 A1 | 11/1998 |
| WO | WO 99/45146 A1 | 9/1999 |
| WO | WO 99/50452 A1 | 10/1999 |
| WO | WO 00/58505 A1 | 10/2000 |
| WO | WO 03/089650 A2 | 10/2003 |
| WO | WO 2005/051174 A2 | 6/2005 |
| WO | WO 2005/073405 A2 | 8/2005 |
| WO | WO 2007/041774 A1 | 4/2007 |
| WO | WO 2007/065926 A1 | 6/2007 |
| WO | WO 2008/040095 A1 | 4/2008 |
| WO | WO 2008/054834 A2 | 5/2008 |
| WO | WO 2008/122084 A1 | 10/2008 |
| WO | WO 2009/022125 A1 | 2/2009 |
| WO | WO 2010/017246 A1 | 2/2010 |

OTHER PUBLICATIONS

Kuwabara et al (Mol. Cell. 2:617-627, 1998).*
International Search Report dated Jan. 19, 2008, (Three (3) pages).
Stojanovic, M.N., "Deoxyribosyme-Based Logic Gates", J. Am. Chem. Soc., 2002, vol. 124, No. 14, pp. 3555-3561.
Stojanovic, M.N., "Deoxyribozyme-Based Half-Adder", J. Am. Chem. Soc., 2003, vol. 125, No. 22, pp. 6673-6676.
Stojanovic, M.N., "Deoxyribozyme-Based Ligase Logic Gates and Their Initial Circuits", J. Am. Chem. Soc., 2005, vol. 127, No. 19, pp. 6914-6915.
U.S. Appl. No. 11/697,021, filed Apr. 5, 2007, Todd et al.
Achenbach et al., "Structure-switching allosteric deoxyribozymes," *Analytica Chimica Acta.*, 534(1):41-51, (2005).
Australian Application No. AU2007304837, first Examination Report mailed Jan. 14, 2010.

(Continued)

*Primary Examiner* — Richard Schnizer
(74) *Attorney, Agent, or Firm* — Alston & Bird LLP

(57) ABSTRACT

The present invention relates to compositions and methods that allow the manipulation of the catalytic activity of multi-component nucleic acid complexes. Further, the invention provides methods which use these compositions and methods to create molecular sensors, molecular switches, and/or modulators or propagators of autocatalytic self-replicating cascades and other iterative processes. More particularly, the invention relates to compositions allowing self-assembly of active and inactive multicomponent nucleic acid complexes, methods of making such compositions, and methods for use.

12 Claims, 12 Drawing Sheets

(56) References Cited

OTHER PUBLICATIONS

Australian Application No. AU2007304837, Notice of Acceptance mailed Sep. 15, 2011.
Australian Application No. AU2007304837, second Examination Report mailed Mar. 7, 2011.
Australian Application No. AU2007304837, third Examination Report mailed Jun. 27, 2011.
Barany, "Genetic disease detection and DNA amplification using cloned thermostable ligase," *PNAS*, 88:189-193, (1991).
Benenson et al., "An autonomous molecular computer for logical control of gene expression," *Nature*, 429:423-429, (2004).
Benenson et al., "Programmable and autonomous computing machine made of biomolecules," *Nature*, 414(6862):430-434, (2001).
Beyer et al., "A modular DNA signal translator for the controlled release of a protein by an aptameter," *Nucleic Acids Research*, 34(5):1581-1587, (2006).
Breaker et al., "A DNA enzyme that cleaves RNA," *Chem Biol.*, 1(4):223-229, (1994).
Breaker, "DNA enzymes," *Nature Biotech.*, 15:427-431, (1997).
Brown et al., "A lead-dependent DNAzyme with a two-step mechanism," *Biochem.*, 42(23):7152-7167, (2003).
Cairns et al., "Nucleic acid mutation analysis using catalytic DNA," Nucl Acids Res, 28(3):e9(i-vi), (2000).
Cairns et al., "Optimisation of the 10-23 DNAzyme-substrate pairing interactions enhanced RNA cleavage acivity at purine-cytosine target sites," *Nucl Acids Res*, 31(11):2883-2889, (2003).
Carmi et al., "In vitro selection of self-cleaving DNAs," *Chem Biol*, 3(12):1039-1046, (1996).
Cox et al., "DNA computation," *Curr Biol*, 11(9):R336, (2001).
Cruz et al., "Dinucleotide junction cleavage versatility of 8-17 deoxyribozyme," *Chem Biol*, 11:57-67, (2004).
Cuenoud et al., "A DNA metalloenzyme with DNA ligase activity," *Nature*, 375:611-614, (1995).
Elghanian et al., "Selective colorimetric detection of polynucleotides based on the distance-dependent optical properties of gold nanoparticles," *Science*, 277:1078-1081, (1997).
Emilsson et al., "Deoxyribozymes: new activities and new applications," *Cell. Mol. Life Sci*, 59:596-607, (2002).
European Search Opinion for application EP07815323.6 mailed Jan. 31, 2011.
European Search Report for application EP07815323.6 mailed Jan. 12, 2011.
Haseloff et al., "Simple RNA enzymes with new and highly specific endoribonuclease activities," *Nature*, 334:585-591, (1988).
Huizenga et al., "A DNA aptamer that binds adenosine and ATP," *Biochemistry*, 34:656-665, (1995).
Illangasekare et al., "Aminoacyl-RNA synthesis catalyzed by an RNA," *Science*, 267:643-647, (1995).
Israel Application No. IL197543, Office Action mailed Jul. 4, 2011. (Hebrew).
Israel Application No. IL197543, Office Action mailed Jul. 4, 2011. (English translation).
Kossen et al., "High throughput ribozyme-based assays for detection of viral nucleic acids," *Chemistry and Biology*, 11:807-815, (2004).
Kuwubara et al., "Allosterically controllable maxizymes cleave mRNA with high efficiency and specificity," *TIBTECH*, 18:462-468, (2000).
Lee et al., "Aptamer Database," *Nucl Acids Res.*, Database Issue, 32:D95-D100, (2004).
Levy et al., "Exponential growth by cross-catalytic cleavage of deoxyribozymogens," *Proc Natl. Acad Sci U S A*, 100(11):6416-6421, (2003).
Li et al., "A catalytic DNA for porphyrin metallation," *Nat Struct Biol*, Correspondence, 3(9):743-747, (1996).
Liu et al., "Adenosine-dependent assembly of aptazyme-functionalized gold nanoparticles and its application as a colorimetric biosensor," *Analytical Chemistry*, 76:1627-1632, (2004).
Lohse et al., "Ribozyme-catalysed amino-acid transfer reactions," *Nature*, 381:442-444, (1996).

Mirkin et al., "A DNA-based method for rationally assembling nanoparticles into macroscopic materials," *Nature*, 382:607-609, (1996).
Mokany et al. "MNAzymes, a versatile new class of nucleic acid enzymes that can function as biosensors and molecular switches," *J Am Chem Soc*, 132:1051-1059, (2010).
New Zealand Application No. NZ575802, first Examination Report mailed Sep. 27, 2010.
Paul et al.,"Minimal self-replicating systems," *Current Opinion in Chemical Biology*, 8:634-639, (2004).
PCT International Preliminary Report on Patentability (Chapter I) for application PCT/AU07/001517 mailed Jan. 19, 2008.
Perreault et al., "Mixed deoxyribo- and ribo-oligonucleotides with catalytic activity," *Nature*, 344:565-567, (1990).
Perreault et al., "Relationship between 2'-hydroxyls and magnesium binding in the hammerhead RNA domain: a model for ribozyme catalysis," *Biochemistry*, 30:4020-4025, (1991).
Prior et al., "Structure-function correlations derived from faster variants of a RNA ligase deoxyribozyme," *Nucleic Acids Research*, 32(3):1075-1082, (2004).
Raillard et al., "Targeting sites within HIV-1 cDNA with a DNA-cleaving ribozyme," *Biochemistry*, 35:11693-11701, (1996).
Sando et al., "Amplified Nucleic Acid Sensing Using Programmed Self-Cleaving DNAzyme," *J. Am. Chem. Soc.*,125:15720-15721, (2003).
Santoro et al., "A general purpose RNA cleaving DNA enzyme," *Proc Natl Acad Sci U S A*, 94:4262-4266, (1997).
Santoro et al., "Mechanism and utility of an RNA-cleaving DNA enzyme," *Biochem*, 37:13330-13342, (1998).
Schubert et al., "Gaining target access for deoxyribozymes," *J Mol Biol*, 339:355-363, (2004).
Schweitzer et al., "Combining nucleic acid amplification and detection," *Current Opinion in Biotechnology*, 12:21-27, (2001).
Sidorov et al., "Sequence-specific cleavage of RNA in the absence of divalent metal ions by a DNAzyme incorporating imidazolyl and amino functionalities," *Nucl Acids Res*, 32(4):1591-1601, (2004).
Silverman, "Breaking up is easy to do (if you're a DNA enzyme that cleaves RNA)," *Chem Biol*, 11:7-8, (2004).
Singapore Application No. SG 00901779-9, first Written Opinion mailed Oct. 5, 2010.
Singapore Application No. SG 00901779-9, second Written Opinion mailed Jun. 13, 2011.
Stojanovic et al., "A Deoxyribozyme-Based Molecular Automaton," *Nature Biotechnology*, 21(9):1069-1074, (2003).
Tabor et al., "Deoxyribozymes that recode sequence information," Nucleic Acids Res, 34(8):2166-2172, (2006).
Tarasow et al., "RNA-catalysed carbon—carbon bond formation," Nature, 389:54-57, (1997).
Todd et al., "DzyNA-PCR: Use of DNAzymes to detect and quantify nucleic acid sequences in a real time fluorescent format," *Clinical Chemistry*, 46(5):625-630, (2000).
U.S. Appl. No. 11/544,926, Final Office Action mailed Nov. 24, 2010.
U.S. Appl. No. 11/544,926, Non-Final Office Action mailed Apr. 6, 2010.
Vaish et al., "Zeptomole detection of a viral nucleic acid using a target-activated ribozyme,"*RNA*, 9:1058-1072, (2003).
Warashina et al., "Extremely high and specific activity of DNA enzymes in cells with a Philadelphia chromosome," *Chem Biol*, 6(4):237-250, (1999).
Zaborowska et al., "Sequence requirements in the catalytic core of the '10-23' DNA enzyme," *J Biol Chem*, 277(43):40617-40622, (2002).
China Application No. CN200780037345.2,first Office Action mailed Jan. 18, 2012.
European Application No. EP07815323.6, Examination Report mailed Oct. 19, 2011.
Mexico Application No. Mx/a/2009/003193, first Examination Report mailed Mar. 7, 2012.
New Zealand Application No. NZ575802, second Examination Report mailed Nov. 17, 2011.

(56) References Cited

OTHER PUBLICATIONS

Soda et al., "A novel maxizyme vector targeting a *bcr-abl* fusion gene induced specific cell death in Philadelphia chromosome—positive acute lymphoblastic leukemia," *Blood*, 104:356-363, (2004).
Tanabe et al., "Maxizymes, Novel Allosterically Controllable Ribozymes, Can Be Designed to Cleave Various Substrates," *Biomacromolecules*, 1:108-117, (2000).
U.S. Appl. No. 11/544,926, Non-Final Office Action mailed Mar. 22, 2012.
U.S. Appl. No. 11/697,021, Non-Final Office Action mailed Dec. 28, 2011.
U.S. Appl. No. 12/594,656, Requirement for Restriction/Election mailed Mar. 1, 2012.
Warashina et al., "Working at the Cutting Edge: the Creation of Allosteric Ribozymes," Structure, Minireview, 8(1):R207-R212, (2000).
AU Application No. 2008235256, First Examination Report mailed Apr. 2, 2013.
CN Application No. 2008880018552.8, Second Office Action mailed Apr. 9, 2013.
EPO Application No. 08733324.1, Communication under Rule 71(3) EPC mailed Oct. 17, 2012.
JP Application No. 2001-501333, First Office Action mailed Mar. 27, 2013.
NZ Application No. 580129, Notice of Acceptance mailed May 8, 2012.
TW Application No. 097112521, First Office Action mailed Jan. 7, 2013.
U.S. Appl. No. 12/594,656, Final Office Action mailed Mar. 21, 2013.
U.S. Appl. No. 13/741,895, Non-Final Office Action mailed Apr. 17, 2013.
Adams, "Biotin amplification of biotin and horseradish peroxidase signals in histochemical stains," J Histochem Cytochem., 40(10):1457-1463, (1992).
Australian application No. AU2006302729, first Examination Report mailed Jan. 5, 2010.
Australian application No. AU2006302729, second Examination Report mailed Aug. 5, 2010.
Australian application No. AU2011202017, first Examination Report mailed Nov. 14, 2011.
Bobrow, et al., "Catalyzed reporter deposition, a novel method signal amplification. Application to immunoassays," J Immunol Methods, 125:279-285, (1989).
Chehab, et al., "Detection of sickle cell anaemia and thalassaemias," Nature, [letter], [published erratum titled "Sickle cell detection: Erratum," 329(10):678, (1987)], 329(9):293-294, (1987).
Chen, et al., "MicroRNA quantitation by looped RT-PCR," Applied Biosystems, Poster, (2005).
Cheng, et al., "A versatile method for coupling of proteins to DNA: synthesis of α2-macroglobin-DNA conjugates," Nucleic Acid Research, 11(3):659-669, (1983).
China Application No. 200680045926.6, first Office Action mailed Mar. 9, 2011.
China Application No. 200690045926.6, second Office Action mailed May 3, 2012.
Compton, "Nucleic acid sequence-based amplification," Nature, 350(6313):91-92, (1991).
Coppins, et al., "Rational modification of a selection strategy leads to deoxyribozymes that create native 3'-5' RNA linkages," J. Am. Chem Soc., 126(50):16426-16432, (2004).
Eigen, et al., "Sorting single molecules: application to diagnostics and evolutionary biotechnology," Proc Natl Acad Sci U S A, 91:5740-5747, (1994).
European Application No. EP06790343.5, first Examination Report mailed Jan. 20, 2010.
European Application No. EP06790343.5, second Examination Report mailed Aug. 11, 2010.
European Application No. EP06790343.5, Supplementary European Search Report and European Search Opinion dated Sep. 16, 2009.
European Application No. EP08733324.1, first Examination Report mailed Jun. 30, 2011.
European Application No. EP08733324.1, first Office Action mailed Feb. 9, 2010.
European Application No. EP08733324.1, further Examination Report mailed Jan. 31, 2012.
European Application No. EP08733324.1, second Office Action mailed Jun. 23, 2010.
European Application No. EP08733324.1, Supplementary European Search Report and European Search Opinion mailed Sep. 28, 2010.
Fahy, et al., "Self-sustained sequence replication (3SR): an isothermal transcription based amplification system alternative to PCR," Cold Spring Harbor Laboratory Press, PCR Methods and Applications, 1:25-33, (1991).
Flynn-Charlebois, et al., "In vitro evolution of an RNA-cleaving DNA enzyme into an RNA ligase switches the selectivity from 3'-5' to 2'-5'," J. Am. Chem. Soc., 125:5346-5350, (2003).
Fokina et al., "Two-Component 10-23 DNA Enzymes," Nucleosides, Nucleotides & Nucleic Acids, 23(6&7):1031-1035, (2004).
Hall, et al., "Sensitive detection of DNA polymorphisms by the serial invasive signal amplification reaction," Proc Natl Acad Sci USA, 97(15):8272-8277, (2000).
Hayden et al., "Self-Assembly of a Group I Intron from Inactive Oligonucleotide Fragments," Chemistry & Biology, 13:909-918, (2006).
Hendry et al., "Redesigned and chemically-modified hammerhead ribozymes with improved activity and serum stability," BMC Chemical Biology, 4(1):1-11, (2004).
Hobartner, et al., "Recent advances in DNA catalysis," Biopolymers. 87(5-6):279:292, (2007).
Impey, et al., "Factors that influence deoxyribozyme cleavage during polymerase chain reaction," Anal Biochem., 28:300-303, (2000).
Israel Application No. IL 201420, first Office Action dated Feb, 23, 2012.
Israel Application No. IL190501, first Office Action dated May 24, 2010.
Israel Application No. IL190501, second Office Action dated Jan. 31, 2012.
Japanese Application No. JP2008-533829, first Office Action mailed Mar. 1, 2012.
Jonas, et al., "Detection and identification of *Mycobacterium tuberculosis* directly from sputum sediments by amplification of rRNA," Journal of Clinical Microbiology, 31(9):2410-2416, (1993).
Kurata, et al., "MAXIZYMEs: Allosterically controllable ribozymes with biosensor functions," Journal of Biochemistry and Molecular Biology, 33(5):359-365, (2000).
Kuwabara, et al., "tRNAVal-heterodimeric maxizymes with high potential as gene-inactivating agents: Simultaneous cleavage at two sites in HIV-1 tat mRNA in cultured cells," Proc Natl Acad Sci USA, 96:1886-1891, (1999).
Li, et al., "In vitro selection and characterization of a highly efficient Zn(II)-dependent RNA-cleaving deoxyribozyme," Nucl Acids Res, 28(2):481-488, (2000).
Lizardi, et al., "Mutation detection and single-molecule counting using isothermal rolling-circle amplification," Nat Genet, 19:225-232, (1998).
McCall, et al., "Minimal Sequence Requirements for Ribozyme Activity," Proc Natl Acad Sci USA, 89:5710-5714, (1992).
Mexico Application No. MX/a/08/004039, first Office Action (spanish language only).
Nagamine, et al., "Isolation of Single-Stranded DNA from Loop-Mediated Isothermal Amplification Products," Biochemical and Biophysical Research Communications, 290(4):1195-1198, (2002).
New Zealand Application No. NZ567403, first Examination report mailed Mar. 18, 2010.
New Zealand Application No. NZ567403, second Examination report mailed Aug. 18, 2010.
New Zealand Application No. NZ580129, Examination Report mailed Mar. 8, 2012.
New Zealand Application No. NZ580129, Examination Report mailed Oct. 4, 2010.
New Zealand Application No. NZ580129, second Examination Report mailed Dec. 22, 2011.

(56) References Cited

OTHER PUBLICATIONS

Notomi, et al., "Loop-mediated isothermal amplification of DNA," Nucl Acids Res, 28(12):E63(i-vii), (2000).
Oshima, et al., "Maxizymes and Small Hairpin-Type RNAs That Are Driven by a tRNA Promoter Specifically Cleave a Chimeric Gene Associated with Leukemia in Vitro and in Vivo,"Cancer Res. 63:6809-6814, (2003).
PCT Application No. PCT/AU2006/001473, International Search Report mailed Dec. 14, 2006.
PCT Application No. PCT/AU2007/001517, Written Opinion of the International Searching Authority, mailed Jan. 19, 2008.
PCT Application No. PCT/AU2008/000492, International Preliminary Report on Patentability (Chapter 1) dated Oct. 6, 2009.
PCT Application No. PCT/AU2008/000492, International Search Report mailed Jul. 4, 2008.
PCT Application No. PCT/AU2011/001504, International Search Report mailed Feb. 17, 2012.
PCT Application No. PCT/AU2011/001504, Written Opinion mailed Feb. 17, 2012.
Perriman, et al., "Extended target-site specificity for a hammerhead ribozyme," Gene, 113:157-163, (1992).
Raap, et al. "Ultra-sensitive FISH using peroxidase-mediated deposition of biotin- or fluorochrome tyramides," Hum Mol Genet, 4(4):529-534, (1995).
Saiki, et al., "Enzymatic amplification of β-globin genomic sequences and restriction site analysis for diagnosis of sickle cell anemia," Science, 230:1350-1354, (1985).
Silverman, "In vitro selection and application of nucleic acid enzymes (Ribozymes and deoxyribozymes)," Wiley Encyclopedia of Chemical Biology, pp. 1-17, (2008).
Singapore Application No. SG200802640-3, Search and Examination Report mailed Apr. 30, 2010.
Singapore Application No. SG200802640-3, Written Opinion and Search Report mailed May 11, 2009.
Singapore Application No. SG200906638-2, final Examination Report mailed Jun. 16, 2011.
Singapore Application No. SG200906638-2, first Written Opinion mailed Aug. 5, 2010.
Swearingen, et al., "Immobilization of a Catalytic DNA Molecular Beacon on Au for Pb (II) Detection," Anal. Chem., 77(2):442-448, (2005).
Urdea, "Synthesis and characterization of branched DNA (bDNA) for direct and quantitative detection of CMV, HBV, HCV and HIV," Clin Chem, 39(4):725-726, (1993).
U.S. Appl. No. 11/697,021, Final Office Action mailed Sep. 10, 2012.
U.S. Appl. No. 11/697,021, Requirement for Restriction/Election mailed Aug. 23, 2011.
U.S. Appl. No. 12/442,275, Requirement for Restriction/Election mailed May 4, 2011.
U.S. Appl. No. 12/594,656, Non-Final Office Action mailed Jul. 2, 2012.
U.S. Appl. No. 11/544,926, Notice of Allowance mailed Oct. 15, 2012.
U.S. Appl. No. 11/544,926, Requirement for Restriction/Election mailed Mar. 20, 2009.
U.S. Appl. No. 11/544,926, Requirement for Restriction/Election mailed Jun. 30, 2009.
Van Gijlswijk, et al., "Fluorochrome-labeled tyramides: use in immunocytochemistry and and fluorescence in situ hybridization," J Histochem Cytochem, 45(3):375-382, (1997).
Walker, et al., "Strand displacement amplification—an isothermal, in vitro DNA amplification technique," Nucl Acids Res, 20(7):1691-1696, (1992).
Xiao et al., "Lighting Up Biochemiluminescence by the Surface Self-Assembly of DNA-Hemin Complexes," ChemBioChem, 5:374-379 (2004).
Yakimovich, et al., "Influence of DNA aptamer structure on the specificity of binding to Taq DNA polymerase," Biochemistry (Moscow), 68(2):228-235, (2003).
Yang et al., "Minimum Ribonucleotide Requirement for Catalysis by the RNA Hammerhead Domains," Biochemistry, 31:5005-5009, (1992).
Zhang, et al., "Aptamer-based multiplexed amplified real-time biochemical detector," Indiana Biosensor Symposium, Poster, (2002).
U.S. Appl. No. 12/594,656, Final Office Action mailed Jan. 11, 2014.
U.S. Appl. No. 12/594,656, Non-Final Office Action mailed Dec. 10, 2013.
U.S. Appl. No. 12/594,656, Notice of Allowance and Examiner Initiated Interview Summary mailed Oct. 14, 2014.
U.S. Appl. No. 13/741,895, Notice of Allowance mailed Sep. 16, 2014.

* cited by examiner

3 AND Gates:

1 ANDAND Gate:

3 NANDNAND Gates:

Any and only 1 → Blue  Any 2 → Green  All 3 → Blue & Green

MOLECULAR SWITCHES AND METHODS FOR THEIR USE

CROSS REFERENCE TO RELATED APPLICATION

This application claims the benefit of U.S. Provisional Patent Application No. 60/828,451 filed 6 Oct. 2006, which is incorporated herein by reference in its entirety.

REFERENCE TO A SEQUENCE LISTING

This application includes an electronic sequence listing in a file named "402144SEQLIST.TXT", created Jun. 4, 2015 and containing 13,994 bytes, which is incorporated by reference in its entirety for all purposes.

TECHNICAL FIELD

The present invention relates to compositions and methods that allow the manipulation of the catalytic activity of multi-component nucleic acid (MNA) complexes. Further, the invention provides methods which use these compositions and methods to create molecular sensors, molecular switches, and/or modulators or propagators of autocatalytic self-replicating cascades and other iterative processes. More particularly, the invention relates to compositions allowing self-assembly of active and inactive multicomponent nucleic acid complexes, methods of making such compositions, and methods for use.

BACKGROUND OF THE INVENTION

In addition to its evolutionary optimized functions, the extraordinary physical and functional properties of nucleic acids provide the opportunity for a plethora of new bio-molecular devices and methods. Designer nucleic acids have been contemplated for therapeutic entities, biosensors, nano-scale devices and tools for molecular computation. The methods exploit the characteristics of DNA self-assembly, electro-conductivity, information elements, amplification, switching, molecular detection and catalytic activity. Further, since DNA is robust, stable and thermostable it provides an ideal material for molecular engineering of mechanical or computation devices.

Single stranded nucleic acids, such as DNA and RNA, have the ability to fold into complex three-dimensional structures that can function as highly specific receptors (aptamers) and catalysts (ribozymes and DNAzymes). Further, the requirement for complementarity between nucleic acid strands for hybridization forms the basis for a wide range of techniques, which allow target detection (e.g. microarray analysis, Northern blotting or Southern blotting), and/or target amplification (e.g. the polymerase chain reaction). Further, hybridization provides the basis for nucleic acid nano-scale construction and for DNA based computational strategies.

Self-replication is a process by which individuals can duplicate (copy) themselves. In such processes, the products of each reaction direct the formation of the new copies (replicons) of the individual from component parts. A wide variety of techniques have been developed for the self-replication of nucleic acid sequences.

Methods for in vitro replication of target nucleic acid sequences (target amplification) are well known in the art. Many of these methods require oligonucleotide primers, capable of specific hybridization with the target DNA or RNA, which can be extended by DNA or RNA polymerase to create a new copy of the target (an amplicon), using the target as a template to direct synthesis. Such techniques (reviewed Schweitzer and Kingsmore, 2001) include the polymerase chain reaction, strand displacement amplification, rolling circle amplification, and loop-mediated isothermal amplification, transcription-mediated amplification, self-sustained sequence replication and nucleic acid sequence replication based amplification. An alternative approach, known as the ligase chain reaction ("LCR") uses a protein ligase to amplify nucleic acid targets. The reaction depends on the capacity of the ligation products from each round to serve as templates to direct the ligation of new copies of the target (Barany, 1991).

Target amplification technologies, such as those above, have been widely used in research and/or in clinical diagnostics. However, despite their power, each has inherent disadvantages. They all require the use of protein enzymes (e.g. DNA polymerase, RNA polymerase, reverse transcriptase, and or ligase). The inclusion of protein enzymes increases the complexity and cost of reagent manufacture and decreases the shelf life of kits containing reagents. Other associated technical challenges include contamination by replicons (target amplicons) from previous reactions leading to false positive signal, and/or background signal caused by replication of primer sequences (primer-dimers) or background caused by target-independent ligation.

A wide variety of nucleic acid molecules, with enzymatic or catalytic activity, have been discovered in the last 20 years. RNA enzymes ("ribozymes") occur in nature but can be engineered to specifically recognize and modify a target RNA substrate (Haseloff and Gerlach, 1988). In vitro evolution techniques have facilitated the discovery and development of many more catalytic nucleic acids, including deoxyribonucleic acids often referred to as "DNA enzymes" or "DNAzymes" (reviewed Emilsson and Breaker, 2002). In vitro evolved DNAzymes and/or ribozymes have been discovered which have the capacity to catalyse a broad range of reactions including cleavage of nucleic acids (Carmi et al., 1996; Raillard and Joyce, 1996; Breaker, 1997; Santoro and Joyce, 1998), ligation of nucleic acids (Cuenoud and Szostak, 1995, Prior et al., 2004), porphyrin metallation (Li and Sen, 1996), and formation of carbon-carbon bonds (Tarasow et al., 1997), ester bonds (Illangasekare et al., 1995) or amide bonds (Lohse and Szostak, 1996).

In particular, DNAzymes and ribozymes have been characterized which specifically cleave distinct nucleic acid sequences after hybridizing via Watson Crick base pairing. DNAzymes are capable of cleaving either RNA (Breaker and Joyce, 1994; Santoro and Joyce, 1997) or DNA (Carmi et al., 1996) molecules. Ribozymes are also able to cleave both RNA (Haseloff and Gerlach, 1988) and DNA (Raillard and Joyce, 1996) target sequences. The rate of catalytic cleavage of many nucleic acid enzymes is dependent on the presence and concentration of divalent metal ions such as $Ba^{2+}$, $Sr^{2+}$, $Mg^{2+}$, $Ca^{2+}$, $Ni^{2+}$, $Co^{2+}$, $Mn^{2+}$, $Zn^{2+}$, and $Pb^{2+}$ (Santoro and Joyce, 1998; Brown et al., 2003).

The "10:23" and "8:17" DNAzymes are capable of cleaving nucleic acid substrates at specific RNA phosphodiester bonds to create reaction products which have 2',3'-cyclic phosphate and 5'-hydroxyl groups (Santoro and Joyce, 1997; reviewed Emilsson and Breaker, 2002). Examples of deoxyribozymes (DNAzymes), which can ligate 2',3'-cyclic phosphate and 5'-hydroxyl products include the "7Z81" and "7Z48" ligases (Prior, 2004).

Several catalytic nucleic acids, including the hammerhead ribozyme, the 10:23 and 8:17 DNAzymes, and the "7Z81" and "7Z48" ligases have similar basic structures with multiple domains. These nucleic acid enzymes have a conserved catalytic domain (catalytic core) flanked by two non-conserved substrate-binding domains ("arms"), which specifically recognize and hybridise to the substrate. While these nucleic acid enzymes can function as true multiple turnover enzymes, each enzyme only has the capacity to recognise one molecule, namely the substrate which it can then catalytically modify.

Catalytic nucleic acids have been shown to tolerate only certain modifications in the area that forms the catalytic core (Perreault et al., 1990; Perreault et al., 1991; Zaborowska et al., 2002; Cruz et al., 2004; Silverman, 2004)). Depending on the stringency of the reaction conditions, some degree of mismatch may be tolerated within the substrate arms. However, the requirement for Watson Crick base pairing is sufficiently strict so as to have enabled the development of protocols that use catalytic nucleic acids to facilitate the discrimination of closely related sequences (Cairns et al., 2000) (WO 99/50452).

"Aptamers" are DNA, RNA or peptide sequences that have the ability to recognize one or more ligands with great affinity and specificity due to their high level structure, for example, a 3-D binding domain or pocket. Many aptamers have been evolved in vitro for their capacity to bind to ligands, including for example, nucleic acids, proteins, prions, small organic compounds, and/or entire organisms. "Aptazymes" have sequences comprised of both aptamer and catalytic nucleic acid sequences (ribozymes or DNAzymes). Binding of a ligand to the aptamer induces a conformation change in the aptazyme which activates a ribozyme or DNAzyme.

Sando and colleagues (2003) developed a signal amplification strategy that used sensing molecules (target-assisted self cleavage (TASC) probes), which contained multiple domains constituting a target sensing sequence, a DNAzyme domain and a dual labelled, DNA/RNA chimeric substrate for the adjoined DNAzyme. While this method avoids the use of protein enzymes, the TASC probes are complex and expensive molecules which must be custom made for each new target.

Several groups have reported the detection of nucleic acid targets, and other analytes with colourimetric readouts (Elghanian et al., 1997, Mirkin et al, 1996, and Liu and Lu, 2004). The strategy uses nanoscopic gold particles tagged with oligonucleotides. The gold particles can then be aggregated by the addition of a "bridging oligonucleotide", causing a change in colour from red to blue (Mirkin et al, 1996). Liu and Lu (2004) extended this strategy by incorporating a DNAzyme substrate into the bridging oligonucleotide, such that activation of the DNAzyme results in cleavage, dispersal of the gold particles and a change in colour from blue to red. The group used the approach to detect lead using a lead sensitive DNAzyme, and to detect adenosine using an aptazyme.

Several examples of amplification cascades, which use catalytic nucleic acids, are known in the art. The zymogene/ DzyNA approach combines target amplification (e.g. PCR), with DNAzyme replication. The DNAzymes, which are co-amplified with the target, cleave one or more universal reporter substrate (s) permitting generic detection of one or more targets (U.S. Pat. No. 6,140,055; U.S. Pat. No. 6,201, 113; U.S. Pat. No. 6,365,724; WO 99/45146, Todd et al., 2000). Strategies for amplification cascades have been devised which use catalytic nucleic acids, instead of protein enzymes to mediate amplification. In another approach, a signal amplification cascade used two inactive, circularized 10:23 DNAzymes which were capable of activating each other by cross cleavage resulting in linearisation. Paul and Joyce (2004) described a replication cascade mediated by a ribozyme with ligase activity. In this reaction, a first ribozyme ligates two RNA containing oligonucleotides to form a second ribozyme. The second ribozyme then ligates two other RNA containing oligonucleotides to form a new first ribozyme, thus triggering a replication cascade, which produces new copies of both the first and second ribozyme.

Nucleic acid cascades have been considered for a range of biotechnological applications, especially in diagnostics. They could allow detection of proteins and nucleic acids for disease diagnosis by facilitating signal amplification. Catalytic nucleic acids and/or cascade reactions can be used for applications other than diagnostics, for example, within the field of computation analysis and biomolecular engineering of nano-scale devices and switches which may be used in therapeutics.

Devices that can convert information from one form into another, according to a finite procedure, are called automata. A programmable finite automaton, which was capable of solving computational problems was developed using protein enzymes (a restriction endonuclease and a ligase) and double stranded DNA (Benenson et al, 2001). The enzymes serve as the "hardware" and the DNA encodes the "software". The input and automata are programmed by selection of the appropriate DNA software. The automaton proceeds via a cascade of cleavage, hybridization and ligation cycles, producing a detectable output molecule that encodes the automaton's final state and thus the computational result.

Simple molecular-scale programmable computers, which use biological molecules as input data and biologically active molecules as outputs, could be used to create systems for the logical control of biological processes (Benenson et al, 2004). As proof of concept in vitro, Benenson et al developed a bio-molecular computer that was capable of (i) measuring the abundance of specific messenger RNA species, and (ii) responding by releasing a single stranded DNA anti-sense molecule capable of affecting gene expression. Another molecular automaton, which used a network of DNAzymes to create molecular-scale logic gates, was programmed to play "tic-tac-toe" (Stojanovic and Stefanovic, 2003). Recently, a binary DNAzyme with ligase activity was engineered to recognize and hybridize ("read") to one sequence, and to ligate ("write") a separate, distinct sequence, which in turn could be amplified by PCR (Tabor et al, 2006).

Methods where DNA computation interfaces with biology can have broad applications. For example, a simple DNA logic gate could regulate release of insulin based on a combination of physiological signals, for example, high blood sugar and low glucagon (Cox and Ellington 2001). Together, the progress in discovering new functionality for nucleic acids has provided a series of tools, such as aptamers and catalytic nucleic acids, and new structural components which allow the development of components for new nano-scale molecular "machines".

Several processes have been used to operate nanodevices and automata including (i) hybridization processes, which include branch chain migration, inhibition of hybridisation between complementary strands by secondary structure formation, for example hairpin formations, (ii) cleavage using a restriction endonuclease and (iii) induction of conformation changes such as rotation around a central DNA axis, shrinking/extension and translatory movements. A modular DNA signal translator for the controlled release of a protein by an aptamer used an arbitrary DNA sequence as "input" (Beyer and Simmel, 2006).

Thus, there is an ongoing need in the art for simple, fast, and cost effective methods for the detection of targets, and for assembly of nano-scale devices, including programmable devices, which can be performed using stable, nucleic acid components.

SUMMARY OF THE INVENTION

In one aspect of the invention, there is provided a molecular switch comprising at least one oligonucleotide partzyme, wherein said partzyme comprises at least one of a catalytic core portion, a sensor arm portion, and a substrate arm portion, and at least one further oligonucleotide component selected from the group comprising an assembly facilitator oligonucleotide, a substrate oligonucleotide, an activity inhibitor and an assembly inhibitor or any combination thereof wherein said molecular switch is capable of forming a multicomponent nucleic acid (MNA) complex.

In one embodiment the switch may comprise a disassembled complex, a partially assembled complex, a fully assembled MNAzyme, or a fully assembled catalytically inactive MNA complex. Further, the switch may comprise an MNAi.

In another embodiment the activity inhibitor comprises a nucleotide sequence substantially non-complementary to at least one of said oligonucleotides.

In another embodiment one or more of the partzyme sensor arms, the partzyme substrate arms, the assembly facilitator oligonucleotide and the substrate oligonucleotide comprise at least two molecules. Further, one or more of the partzyme sensor arms, the partzyme substrate arms, the assembly facilitator oligonucleotide, the substrate oligonucleotide, the activity inhibitor or assembly inhibitor may comprise at least one region of self-complementarity.

In another embodiment, one or more of the partzyme sensor arms, the partzyme substrate arms, the assembly facilitator oligonucleotide and the substrate oligonucleotide may further comprise at least one aptamer and at least one assembly inhibitor.

In another embodiment, at least one component of said switch is capable of being adapted so as to increase or decrease the sensitivity of the complex to an input event and/or to alter the intensity of an output signal.

In a further embodiment the activity inhibitor may comprise at least one of an assembly facilitator domain, activity inhibitor domain, a reporter domain, a substrate domain, or any combination thereof.

In another embodiment the switch may further comprise at least one stabiliser arm.

In another embodiment at least one component of said switch may comprise a nucleic acid.

In a further embodiment at least one component of said switch may further comprises at least one nanoparticle, microparticle, or combination thereof.

In another aspect of the invention there is provided use of an MNA complex as a molecular switch, wherein said complex transitions from an inactive to an active MNA complex in response to an input event.

In one embodiment the inactive complex may comprise a disassembled complex, a partially assembled complex, or a fully assembled catalytically inactive complex. Further, the catalytically inactive MNA complex may comprise an assembly inhibitor. Still further, the catalytically inactive MNA complex may be an MNAi.

In another embodiment the MNAi may comprise an activity inhibitor which comprises at least one of an activity inhibitor domain, an activator assembly facilitator domain, a reporter domain, a substrate domain, or any combination thereof.

In another embodiment the transition to an active MNAzyme may comprise displacement from said MNAi of at least said activity inhibitor or activity inhibitor domain. Further, the displacement may involve cleavage of a cleavable substrate linking said activity inhibitor domain and said activator assembly facilitator domain.

In another embodiment the input event may comprise removal of an inhibitor or inactivation of an inhibitory function thereof. Further, the input event may result in the assembly of a catalytically active MNAzyme. Still further, the input event may comprise provision of an activator which is (i) provided by exogenous provision or (ii) a product of a reaction in the environment of the MNA complex.

In another aspect of the invention, there is provided the use of an MNA complex as a molecular switch, wherein said complex transitions from an active to an inactive MNA complex in response to an input event.

In one embodiment the active complex may be an MNAzyme.

In another embodiment the transition to an inactive MNA complex may be associated with disassembly of an active MNA complex. Further, transition to an inactive MNA complex may be associated with assembly of an inactive MNA complex.

In another embodiment the input event may be addition of an inhibitor or activation of an inhibitory function thereof. Further, the input event may be binding of an inhibitor. Still further the inhibitor may be an assembly inhibitor. Yet still further, the inhibitor may be an activity inhibitor or activity inhibitor domain.

In another embodiment the inactive MNA complex may be an MNAi.

In another embodiment the activity inhibitor or assembly inhibitor may be (i) provided by exogenous provision or (ii) a product of a reaction in the environment of the MNA complex.

In another embodiment of either of the previous two aspects the transition may result in a change in output signal.

In another embodiment of either of the previous two aspects the input event may be selected from the group comprising change in temperature, salt concentration, ionic strength, pH, divalent cation presence or absence, type or concentration, electric charge, magnetic charge, physical manipulation and change in concentration of an MNA or modulator component or component of the microenvironment, or any combination thereof.

In another embodiment of either of the previous two aspects the change in output signal may comprise the appearance of a signal previously absent, the disappearance of a signal previously present, or an increase or decrease in output signal.

In another embodiment of either of the previous two aspects the output signal may depend on extent of modification of a substrate, wherein the modification is selected to from the group comprising cleavage, ligation, porphyrin metallation, formation of carbon-carbon bonds, ester bonds or amide bonds, or any combination thereof.

In another embodiment of either of the previous two aspects the output signal may be determined by fluorescence spectroscopy, surface plasmon resonance, mass spectroscopy, NMR, electron spin resonance, polarization fluorescence spectroscopy, circular dichroism, immunoassay, chromatography, radiometry, photometry, scintigraphy, electronic methods, UV, visible light or infra red spectroscopy, enzymatic methods or any combination thereof. Further, the determination may be performed in a manner permitting the output signal to be quantified. Still further, the magnitude of the input event may be determined from the quantified output signal. Yet still further, either or both of the input event or the output signal may be amplified. Further still, the output signal amplification may be generated by a signal cascade.

In another aspect of the invention there is provided an MNAi comprising two or more oligonucleotide components and at least one activity inhibitor molecule.

In one embodiment the MNAi may further comprise at least one assembly facilitator.

In another embodiment the activity inhibitor may comprise at least one of an activator assembly facilitator domain, activity inhibitor domain, a reporter domain, a substrate domain, or any combination thereof. Further, at least two of the activity inhibitor domain, the activator assembly facilitator domain and the reporter domain may be located on distinct domains of the activity inhibitor. Still further, at least two of the activity inhibitor domain, the activator assembly facilitator domain and the reporter domain may be linked by a labile linker or cleavable substrate. Yet still further, the substrate may comprise at least one of an activator assembly facilitator domain, an activity inhibitor domain, a reporter domain, or any combination thereof.

In another embodiment the activity inhibitor may comprise a nucleotide sequence substantially non-complementary to at least one of said two or more oligonucleotide components.

In another embodiment the assembly facilitator may be a target. Further, the nucleic acid may be selected from the group consisting of DNA, methylated DNA, alkylated DNA, RNA, methylated RNA, microRNA, siRNA, shRNA, tRNA, mRNA, snoRNA, stRNA, smRNA, pre- and pri-microRNA, other non-coding RNAs, ribosomal RNA, derivatives thereof, amplicons, or any combination thereof.

In another embodiment at least one component of the MNAi may further comprise an aptamer.

In another aspect of the invention there is provided an MNAi composition comprising at least two or more oligonucleotide components wherein at least a first oligonucleotide component and a second oligonucleotide component are capable of self-assembly in the presence of at least one MNA complex activity inhibitor wherein each of said at least first and said second oligonucleotide components comprise a substrate arm portion, a catalytic core portion, and a sensor arm portion; wherein upon self-assembly, the sensor arm portion of said first and second oligonucleotide components act as sensor arms, the substrate arm portion of the first and second oligonucleotide components act as substrate arms, and the catalytic core portion of the first and second oligonucleotide components form the non-functional catalytic core; and wherein upon self-assembly at least one sensor arm interacts with said activity inhibitor and said first and second oligonucleotide components are maintained in proximity for association of their respective catalytic core portions to form a non-functional catalytic core.

In one embodiment the MNAi composition may further comprise at least one assembly facilitator.

In another embodiment the activity inhibitor may comprise at least one of an activator assembly facilitator domain, activity inhibitor domain, a reporter domain, a substrate domain, or any combination thereof.

In another embodiment at least two of the activity inhibitor domain, the activator assembly facilitator domain and the reporter domain may be located on distinct domains of the activity inhibitor. Further, at least two of the activity inhibitor domain, the activator assembly facilitator domain and the reporter domain may be linked by a labile linker or a cleavable substrate.

In another embodiment the activity inhibitor may be a substrate.

In another embodiment the activity inhibitor may comprise a nucleotide sequence substantially non-complementary to at least one of said two or more oligonucleotide components.

In another embodiment at least one component of the complex may contain at least one aptamer or portion thereof wherein said aptamer or portion thereof binds a ligand selected from the group comprising nucleic acids, proteins, glycoproteins, lipids, lipoproteins, cells, viruses, bacteria, archaea, fungi, antibodies, metabolites, pathogens, toxins, contaminants, poisons, small molecules, polymers, metal ions, metal salts, prions or any derivatives, portions or combinations thereof.

In another aspect of the invention there is provided a method for the detection of an assembly facilitator using a signal cascade comprising a first MNAzyme, an MNA complex initially present in a substantially catalytically inactive form (MNAi), an activity inhibitor capable of being modified by said first MNAzyme to provide a detectable effect, wherein said activity inhibitor is both an activity inhibitor and a potential substrate; and wherein association of said assembly facilitator with partzymes for said first MNAzyme under conditions permitting catalytic activity of said first MNAzyme facilitates the catalytic activity of said first MNAzyme thereby providing modification of said activity inhibitor to release an activator assembly facilitator domain and an activity inhibitor domain of said activity inhibitor and wherein said release provides said detectable effect; and wherein said released activator assembly facilitator domain facilitates assembly of a second MNAzyme from components of said MNA complex; and wherein catalytic activity of said second MNAzyme modifies said activity inhibitor to release further activity inhibitor domains and further activator assembly facilitator domains, and wherein said release provides further detectable effect, and;

wherein said further activator assembly facilitator domains facilitate assembly of additional second MNAzymes thereby providing further said catalytically active second MNAzymes thereby providing further detectable effect indicative of the presence of said assembly facilitator.

In one embodiment the activity inhibitor may be a reporter-inhibitor-facilitator.

In another embodiment one or more of said activity inhibitor, said first MNAzyme or said second MNA complex components may be attached to an insoluble support.

In another embodiment one or more of said activity inhibitor, said first MNAzyme or said second MNA complex components may be free in solution.

In another embodiment the activity inhibitor may comprise at least one of an assembly facilitator domain, activity inhibitor domain, a reporter domain, a substrate domain, or any combination thereof. Further, the activity inhibitor may comprise a detectable moiety and a quencher, wherein upon modification of said activity inhibitor by said first or said second MNAzyme, a detectable effect provided by said detectable moiety is increased or decreased. Still further, the detectable effect may be detected by fluorescence spectroscopy, surface plasmon resonance, mass spectroscopy, NMR, electron spin resonance, polarization fluorescence spectroscopy, circular dichroism, immunoassay, chromatography, radiometry, photometry, scintigraphy, electronic methods, UV, visible light or infra red spectroscopy, enzymatic methods or any combination thereof. Yet still further, the detectable effect may be measured and the magnitude of said measurement is indicative of the quantity of an assembly facilitator.

In another embodiment the assembly facilitator may be a target. Further, the target may be a nucleic acid selected from the group comprising DNA, methylated DNA, alkylated DNA, RNA, methylated RNA, microRNA, siRNA, shRNA, tRNA, mRNA, snoRNA, stRNA, smRNA, pre- and pri-microRNA, other non-coding RNAs, ribosomal RNA, derivatives thereof, amplicons, or any combination thereof.

In another embodiment at least one of the components of the first MNAzyme and/or the second MNAcomplex further may comprise an aptamer and wherein said method provides for the detection of a ligand which binds to said aptamer. Further, the ligand may comprise protein, polypeptide, peptide or nucleic acid, glycoproteins, lipids, lipoproteins, cells, viruses, bacteria, archaea, fungi, antibodies, metabolites, pathogens, toxins, contaminants, poisons, entire organisms, small molecules, polymers, metal ions, metal salts, prions or any derivative, portion or combination thereof.

In another embodiment the assembly facilitator may be a synthetic oligonucleotide which acts as an input event.

In another embodiment the assembly of catalytically active MNAzymes may be regulated by an input event selected from the group comprising change in temperature, salt concentration, ionic strength, pH, divalent cation presence or absence, type or concentration, electric charge, magnetic charge, physical manipulation and change in concentration of an MNA or modulator component or component of the microenvironment, or any combination thereof.

In another aspect of the invention there is provided a method of detecting a target using a cascade, wherein said casade comprises an initiating MNAzyme formed in the presence of said target; a first MNAzyme formed in the presence of a product of said initiating MNAzyme; an additional MNAzyme formed in the presence of a product of said first MNAzyme wherein said method comprises the steps of;
  (i) modifying a first substrate with said initiating MNAzyme to generate a first assembly facilitator;
  (ii) assembling said first MNAzyme with said first assembly facilitator;
  (iii) modifying an additional substrate with said first MNAzyme to generate an additional assembly facilitator;
  (iv) assembling said additional MNAzyme with said additional assembly facilitator;
  (v) modifying said first substrate with said additional MNAzyme to generate said first assembly facilitator;
  (vi) assembling said first MNAzyme with said first assembly facilitator released from (v) thereby forming an amplification cascade; and
  wherein said modification of at least one of said first or said additional substrates produces a detectable effect indicative of the presence of said target.

In one embodiment either or both of said first or said additional assembly facilitators may be activator assembly facilitators.

In another embodiment the first substrate may be an activity inhibitor of said first MNAzyme.

In another embodiment the amplification cascade may be a feedback amplification cascade.

In another embodiment the additional substrate may be an activity inhibitor for said additional MNAzyme.

In another embodiment the first and/or said additional MNAzyme may comprise two partzymes which become catalytically active in the presence of at least one assembly facilitator.

In another embodiment the first and/or said additional MNAzyme may comprise two partzymes which become catalytically active in the presence of at least two assembly facilitator components.

In another embodiment the first and/or said additional MNAzyme may comprise two partzymes which become catalytically active in the presence of three or more assembly facilitator components.

In another embodiment the target may be an assembly facilitator molecule to be detected, identified or quantitated. Further, the target may comprise a nucleic acid. Still further, the nucleic acid may be selected from the group comprising DNA, methylated DNA, alkylated DNA, RNA, methylated RNA, microRNA, siRNA, shRNA, tRNA, mRNA, snoRNA, stRNA, smRNA, pre- and pri-microRNA, other non-coding RNAs, ribosomal RNA, derivatives thereof, amplicons, or any combination thereof. Yet still further, the source of said nucleic acid may be selected from the group comprising synthetic, mammalian, human, animal, plant, fungal, bacterial, viral, archael or any combination thereof.

In another embodiment at least one of said MNAzymes may further comprise at least one aptamer. Further, the aptamer may bind at least one ligand. Still further, the ligand may be selected from the group comprising proteins, polypeptides, peptides, nucleic acids, glycoproteins, lipids, lipoproteins, cells, viruses, bacteria, archaea, fungi, antibodies, metabolites, pathogens, toxins, contaminants, poisons, entire organisms, small molecules, polymers, metal ions, metal salts, prions or any derivatives, portions or combinations thereof.

In another embodiment at least one component of said MNAzymes or said substrates may be attached to an insoluble support or free in solution.

In another embodiment the substrate or substrates may comprise a detectable portion and a quencher portion, and wherein upon modification of said substrate by at least one of said MNAzymes, a detectable effect is provided by said detectable portion.

In another embodiment the detectable effect may be detected by at least one of fluorescence spectroscopy, surface plasmon resonance, mass spectroscopy, NMR, electron spin resonance, polarization fluorescence spectroscopy, circular dichroism, immunoassay, chromatography, radiometry, photometry, scintigraphy, electronic methods, UV, visible light or infra red spectroscopy, enzymatic methods or any combination thereof. Further, the detectable effect may be measured, wherein the magnitude of said measurement is indicative of the quantity of a target.

In another aspect of the invention there is provided a method for detecting a target using a signal amplification cascade, said signal amplification cascade comprising partzymes for a first MNAzyme, a first substrate, partzymes for a second MNAzyme, a DNAzyme ligase, a second substrate, an additional partzyme and an assembly facilitator for an additional MNAzyme and an additional substrate, said method comprising the following steps:
  (i) forming said first MNAzyme from said partzymes for a first MNAzyme in the presence of a target molecule to be detected
  (ii) cleaving said first substrate with said first MNAzyme to generate a plurality of cleavage products
  (iii) ligating at least one of said cleavage products with said second substrate by said DNAzyme ligase to create a ligated partzyme for said additional MNAzyme;
  (iv) forming said second MNAzyme from said partzymes for a second MNAzyme by assembly with at least one of said cleavage products;

(v) cleaving said first substrate with said second MNAzyme to generate further said plurality of cleavage products;
(vi) forming further said second MNAzyme by assembly with at least one of said further said plurality of cleavage products wherein assembly of further said second MNAzyme thereby forms an amplification cascade resulting in accumulation of further said plurality of cleavage products wherein at least one of said further said plurality of cleavage products acts as a substrate for said DNAzyme ligase;
(vii) forming said additional MNAzyme with said additional partzyme and with said ligated partzyme, together with said assembly facilitator;
(viii) modifying said additional substrate with said additional MNAzyme resulting in a detectable effect indicative of the presence of said target.

In one embodiment the amplification cascade may be a feedback amplification cascade.

In another embodiment the cleavage product ligated with the second substrate may have a 2',3'-cyclic phosphate at its 3' terminus.

In another embodiment at least one of said cleavage products may be an activator assembly facilitator.

In another embodiment the target may be a molecule to be detected, identified, or quantitated. Further, the target may comprise a nucleic acid. Still further, the nucleic acid may be selected from the group comprising DNA, methylated DNA, alkylated DNA, RNA, methylated RNA, microRNA, siRNA, shRNA, tRNA, mRNA, snoRNA, stRNA, smRNA, pre- and pri-microRNA, other non-coding RNAs, ribosomal RNA, derivatives thereof, amplicons, or any combination thereof. Still further, the source of said nucleic acid may be selected from the group comprising synthetic, mammalian, human, animal, plant, fungal, bacterial, viral, archael or any combination thereof.

In another embodiment at least one of said partzymes for a first MNAzyme, said first substrate, said partzymes for a second MNAzyme, said DNAzyme ligase, said second substrate, said additional partzyme, said assembly facilitator for an additional MNAzyme and said additional substrate may further comprise at least one aptamer. Still further, the aptamer may bind at least one ligand. Yet still further, the ligand may be selected from the group comprising proteins, polypeptides, peptides, nucleic acids, glycoproteins, lipids, lipoproteins, cells, viruses, bacteria, archaea, fungi, antibodies, metabolites, pathogens, toxins, contaminants, poisons, entire organisms, small molecules, polymers, metal ions, metal salts, prions or any derivatives, portions or combinations thereof.

In another embodiment at least one of said partzymes for a first MNAzyme, said first substrate, said partzymes for a second MNAzyme, said DNAzyme ligase, said second substrate, said additional partzyme, said assembly facilitator for an additional MNAzyme and said additional substrate may further comprise at least one nanoparticle, microparticle, or combination thereof.

In another embodiment at least one of said partzymes for a first MNAzyme, said first substrate, said partzymes for a second MNAzyme, said DNAzyme ligase, said second substrate, said additional partzyme, said assembly facilitator for an additional MNAzyme and said additional substrate may be attached to an insoluble support or is free in solution.

In another embodiment at least one of said substrates may comprise a detectable portion and a quencher portion, wherein upon modification of said substrate by said MNAzyme a detectable effect is provided by said detectable portion.

In another embodiment the detectable effect may be detected by at least one of fluorescence spectroscopy, surface plasmon resonance, mass spectroscopy, NMR, electron spin resonance, polarization fluorescence spectroscopy, circular dichroism, immunoassay, chromatography, radiometry, photometry, scintigraphy, electronic methods, UV, visible light or infra red spectroscopy, enzymatic methods or any combination thereof. Further, the detectable effect may be measured and wherein the magnitude of said measurement is indicative of the quantity of said target.

In one embodiment of any of the previous aspects said target is a molecule to be detected, identified, or quantitated. The target may comprise a nucleic acid. The nucleic acid may be selected from the group comprising DNA, methylated DNA, alkylated DNA, RNA, methylated RNA, microRNA, siRNA, shRNA, tRNA, mRNA, snoRNA, stRNA, smRNA, pre- and pri-microRNA, other non-coding RNAs, ribosomal RNA, derivatives thereof, amplicons, or any combination thereof.

The source of the nucleic acid may be selected from the group comprising synthetic, mammalian, human, animal, plant, fungal, bacterial, viral, archael or any combination thereof.

In one embodiment of any of the previous aspects the method or composition may incorporate an aptamer and can detect ligands which bind aptamers, including but not limited to, protein, polypeptide, peptide or nucleic acid, glycoproteins, lipids, lipoproteins, cells, viruses, bacteria, archaea, fungi, antibodies, metabolites, pathogens, toxins, contaminants, poisons, entire organisms, small molecules, polymers, metal ions, metal salts, prions or any derivative, portion or combination thereof, or any other entity.

In one embodiment of any of the previous aspects at least one component of an MNA complex may comprise a nucleic acid or a protein. The nucleic acid may comprise at least one of a labeled nucleic acid, RNA, DNA, nucleic acid analogue, peptide nucleic acid, locked nucleic acid, peptide-nucleic acid chimera, or any combination thereof. The protein may comprise at least one of an antibody, polypeptide, glycoprotein, lipoprotein, or any combination thereof.

At least one component of an MNA complex may further comprise at least one nanoparticle or microparticle, or combination thereof. The component may be attached to an insoluble support or be free in solution. A substrate component may comprise a detectable portion and a quencher portion, wherein upon modification of said substrate by said MNAzyme, a detectable effect provided by said detectable portion is increased or decreased.

In one embodiment of any of the previous aspects the detectable effect may be detected by fluorescence spectroscopy, surface plasmon resonance, mass spectroscopy, NMR, electron spin resonance, polarization fluorescence spectroscopy, circular dichroism, immunoassay, chromatography, radiometry, photometry, scintigraphy, electronic methods, UV, visible light or infra red spectroscopy, enzymatic methods or any combination thereof. The detectable effect may be measured, wherein the magnitude of said measurement is indicative of the quantity of a target.

In another aspect of the invention, there is provided full adder comprising a plurality of MNA complexes wherein said full adder may comprise eight possible combinations of three inputs to generate four possible combinations of two outputs, wherein the four possible combinations are no output, a first output, a second output, or both the first and second output.

In one embodiment the presence of no inputs produces no outputs.

In another embodiment, in response to any and exactly one input, the full adder may generate a first output.

In another embodiment, in response to any and exactly two inputs, the full adder may generate a second output.

In another embodiment, in response to three inputs, the full adder may generate a first and second output.

In another embodiment, at least one of the inputs may be a detectable event.

In another embodiment, at least one of the outputs may be detectable event or a detectable effect determined by at least one of fluorescence spectroscopy, surface plasmon resonance, mass spectroscopy, NMR, electron spin resonance, polarization fluorescence spectroscopy, circular dichroism, immunoassay, chromatography, radiometry, photometry, scintigraphy, electronic methods, UV, visible light or infra red spectroscopy, enzymatic methods or any combination thereof.

In another embodiment the first or second outputs acts as an input to another full adder.

BRIEF DESCRIPTION OF THE DRAWINGS

A preferred embodiment of the present invention will now be described, by way of an example only, with reference to the accompanying drawings wherein.

An increase in fluorescence was observed in reaction (i), which contained all the components of partzymes A and B and an assembly facilitator. This is consistent with the assembly of active MNAzymes and cleavage of the substrate in this reaction. The omission of the stabilizer arm portion of partzyme B (reaction (ii)) resulted in no increase in signal over time indicating that this component is essential for the assembly of active MNAzymes in this system. A control reaction lacking an assembly facilitator (reaction (iii)) also showed no increase in fluorescence over time.

Figure 4:
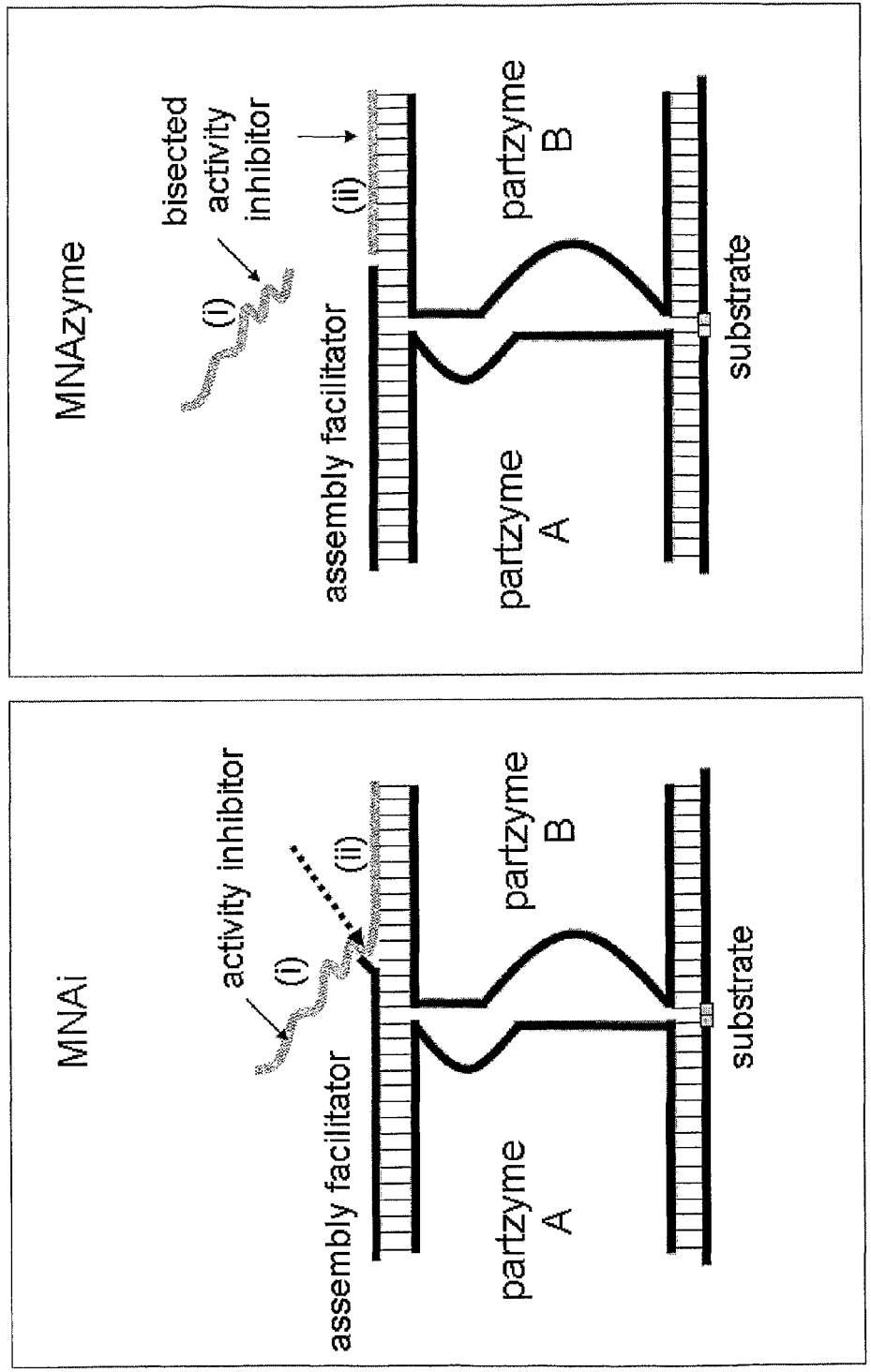

FIG. 4: Depiction of an exemplary design for an MNAi (left hand side) and an active MNAzyme (right hand side): An MNAi is formed when partzymes A and B complex with an assembly facilitator component and an activity inhibitor (left hand side). The MNAi is capable of interacting with, but not catalytically modifying, the substrate. In some embodiments, the activity inhibitor may further include a labile or cleavable linker (indicated by the dotted arrow), which may separate two or more domains within the activity inhibitor. Such domains may include, for example, (i) an activity inhibitor domain which is substantially non-complementary to the partzyme components and which exerts an inhibitory effect by disrupting the secondary structure required for formation of a catalytically active MNAzyme and (ii) an activator assembly facilitator domain, which if separated from the activity inhibitor domain, may function as an assembly facilitator component and direct the assembly of an active MNAzyme.

Figure 5:
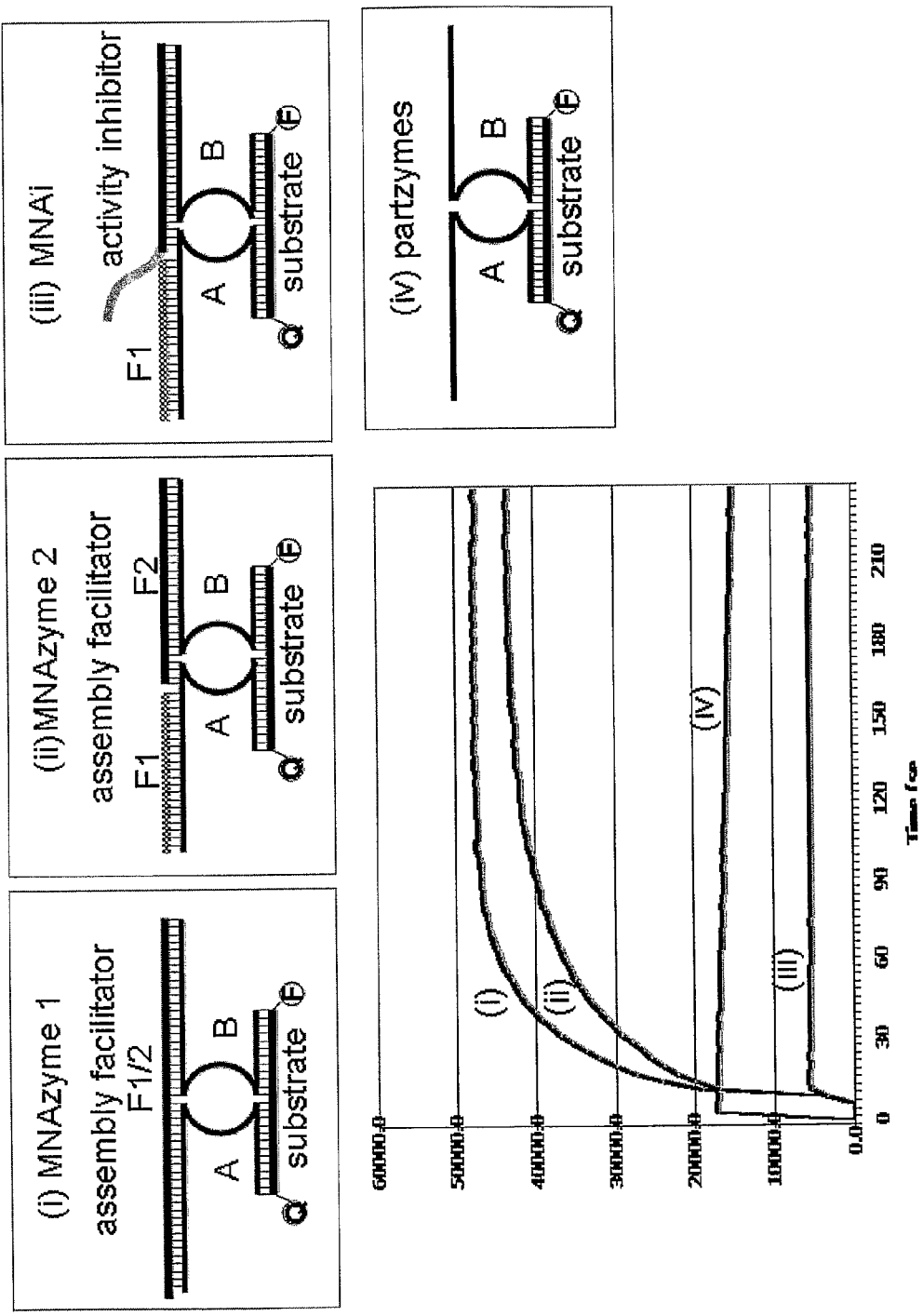

FIG. 5: Demonstration of catalytic activity from various multi-component nucleic acid complexes. All reactions contained partzyme A, partzyme B, and a substrate labelled with a fluorophore quencher dye pair. In addition, reactions contained either (i) an assembly facilitator F1/2, (ii) an assembly facilitator comprising components F1 and F2 (the sequence of which together correspond to that of assembly facilitator F1/2), (iii) assembly facilitator portion F1 and an activity inhibitor containing two joined domains corresponding to an activity inhibitor domain and a domain with the same sequence as F2 or (iv) no assembly facilitator or activity inhibitor.

The change in fluorescence was monitored over time as a measure of catalytic cleavage of the substrate by active MNAzyme complexes (FIG. 5). The fluorescence increased rapidly in reactions containing either assembly facilitator F1/2 or assembly facilitator F1 and F2, indicating the formation of active MNAzymes 1 and 2 respectively, both of which are capable of cleaving the substrate. In contrast, the reaction containing F1 and the activity inhibitor showed no increase in fluorescence over time indicating the formation of MNAi complexes. No increase in fluorescence was seen in the absence of assembly facilitator.

Figure 6:
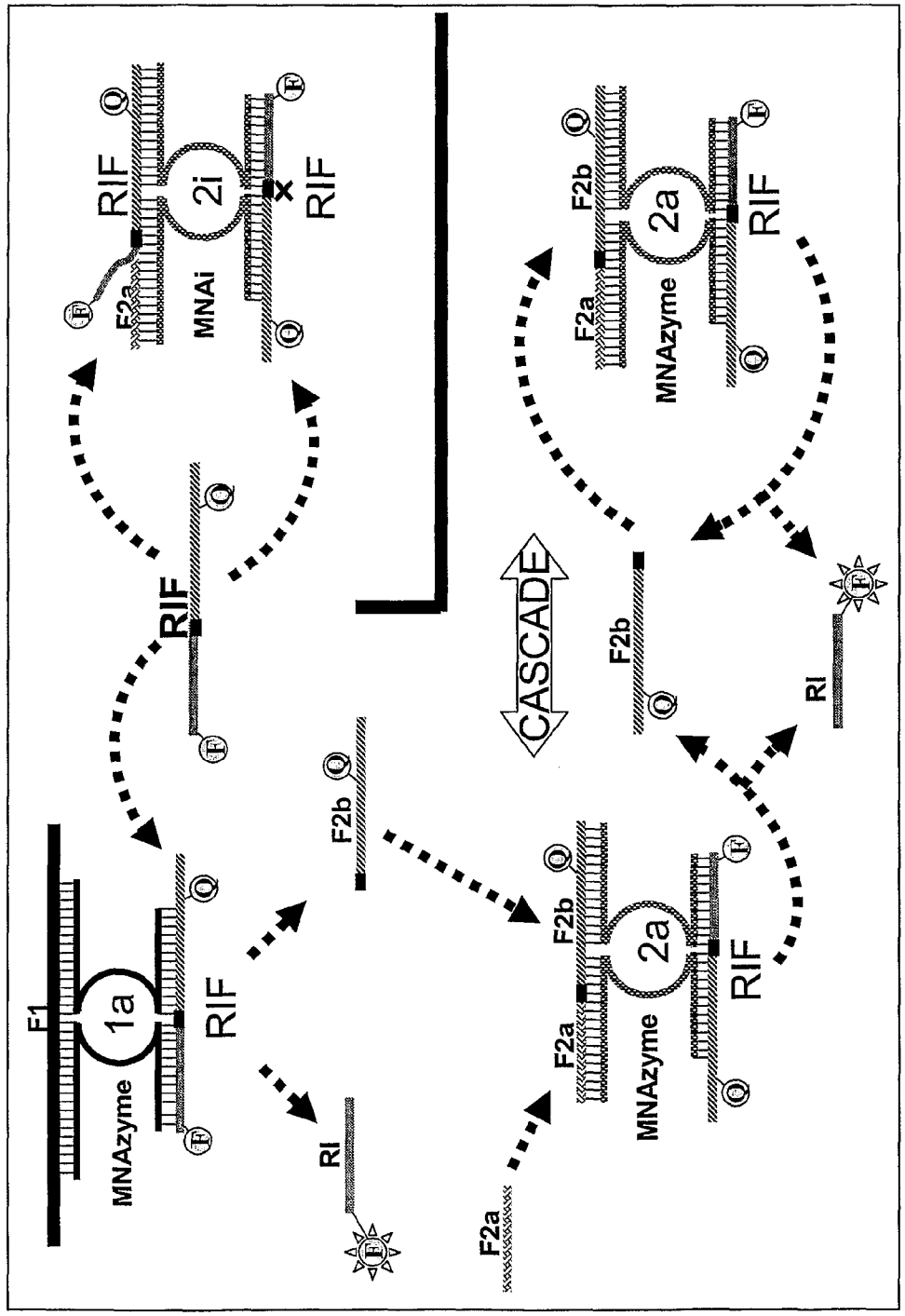

FIG. 6: Schematic representation of Signal Cascade using DNA (SCUD). The illustrated protocol includes the following components: (i) a dual labelled RIF (Reporter-Inhibitor-Facilitator) component containing multiple domains;
  a. the RI domain, comprising an activity inhibitor/reporter domain, which has the dual functions of firstly being an activity inhibitor (when incorporated in RIF) and secondly providing a fluorescent output signal when RIF is cleaved,
  b. an activator assembly facilitator domain F2b which is an essential component for assembly of an active MNAzyme 2a complex, and
  c. a substrate sequence located between the RI and F2b, which when cleaved by either MNAzyme 1a or MNAzyme 2a results in the separation of the RI and F2b domains (ii) an assembly facilitator component F2a (iii) partzyme components capable of forming active MNAzyme 1a structures only in the presence of another assembly facilitator (F1), which by way of example could be a target nucleic acid present in a test sample; the active MNAzyme 1a being capable of cleaving RIF, thus liberating and activating the F2b domain, by removal of the RI domain (which can then fluoresce and generate output signal), (iv) partzymes capable of forming active MNAzyme 2a only when the partzyme arms bind the liberated F2b domain adjacent to a F2a domain. The MNAzyme 2a in turn can cleave more RIF liberating more F2b thus creating a cascade of autocatalytic self-replication of MNAzyme 2a. In the presence of intact RIF, the components of MNAzyme 2a are assembled into an MNAi 21 complex.

In the absence of F1 the partzymes for MNAzyme 2a would form an MNAi 21 complex with intact RIF. In the presence of F1, active MNAzyme 1a would form and cleave RIF, releasing F2b which would then be free to associate and facilitate assembly of an active MNAzyme 2a. Since MNAzyme 2a can further cleave more RIF, this would initiate a signal cascade. SCUD (FIG. 6) could be initiated by either nucleic acid targets (DNA and/or RNA), or other target analytes (proteins, small molecules etc) if the SCUD strategy was linked with an aptamer-MNAzyme system (as shown in FIG. 7).

Figure 7:
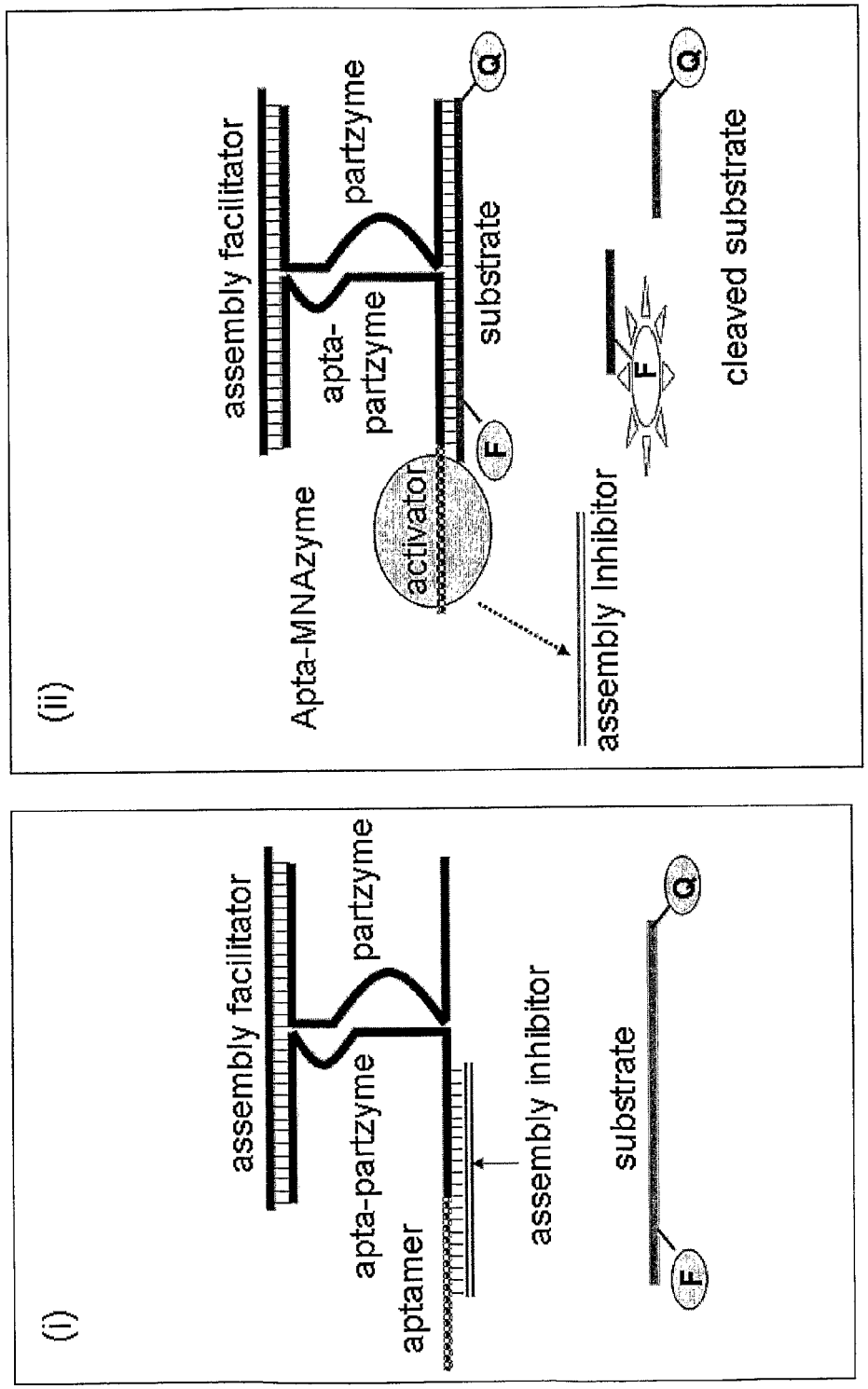

FIG. 7: An exemplary strategy for the modulation of the activity of MNAzymes.

The strategy in this system can be used either as (i) a method to control MNAzyme activity using ligands as activator molecules, and/or (ii) a method of detection of non-nucleic acid targets using apta-MNAzymes.

The nucleic acid oligonucleotides included in this exemplary apta-MNAzyme detection strategy include;
a) a standard partzyme;
b) an apta-partzyme which is a partzyme with an aptamer incorporated into one of its ends;
c) an assembly facilitator which is an oligonucleotide which binds to both the apta-partzyme and the partzyme enabling assembly of an active MNAzyme;
d) a reporter substrate; and
e) an assembly inhibitor oligonucleotide which hybridises to the apta-partzyme in a region which spans at least part of the aptamer sequence and part of the substrate binding arm of the apta-partzyme sequence.

In the absence of an activator ligand (left hand panel), the assembly inhibitor oligonucleotide binds to the apta-partzyme thus competing with and blocking binding of the reporter substrate. When an activator ligand is present (right hand panel), it binds to the aptamer sequence of the apta-partzyme, blocking the binding of the assembly inhibitor oligonucleotide, and thus allowing binding and cleavage of the reporter substrate. As such, MNAzymes can only form and cause fluorescent signal generation in the presence of ligands that can bind aptamers. This approach can be used to develop molecular switches that can turn on and off the catalytic activity of the MNA system. Alternatively it can also be applied to detection of both nucleic acid and non-nucleic acid target ligands.

It will also be appreciated by one skilled in the art that one or more aptamers could be incorporated into any of the oligonucleotide components, including but not limited to the partzymes, the assembly facilitator or the substrate. Further the aptamer could be incorporated into either end of any one of these oligonucleotides. In one embodiment the aptamer is attached to at least one sensor arm of a partzyme. In another embodiment the aptamer is attached to at least one substrate arm of a partzyme.

Figure 8:
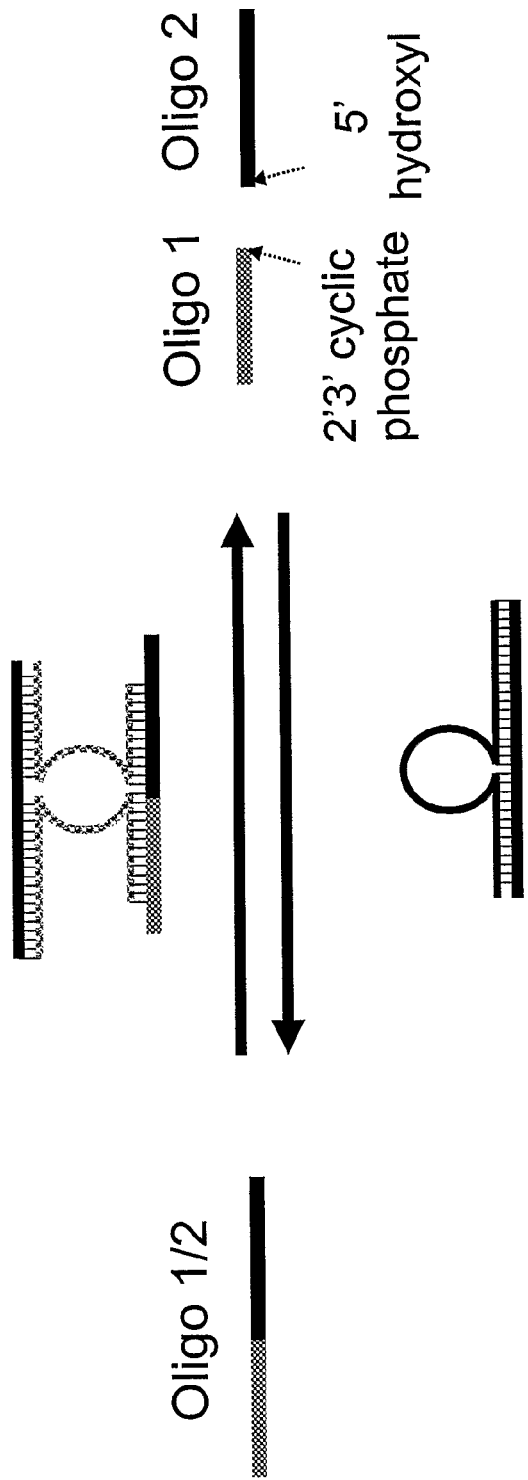

FIG. 8: An example of a cleavage/ligation cascade mediated by a DNAzyme ligase and an MNAzyme: An oligonucleotide such as oligo 1/2 can be cleaved by an MNAzyme into cleavage products oligo 1 and oligo 2, thus generating 2',3'-cyclic phosphate and 5'-hydroxyl products, which can participate in a subsequent ligation reaction. A DNAzyme ligase, for example 7Z81 (Prior et al, 2004) can ligate a first oligonucleotide (oligo 1) to the second oligonucleotide (oligo 2) to create an oligonucleotide ligation product with the same nucleotide sequence of oligo 1/2.

Figure 9:
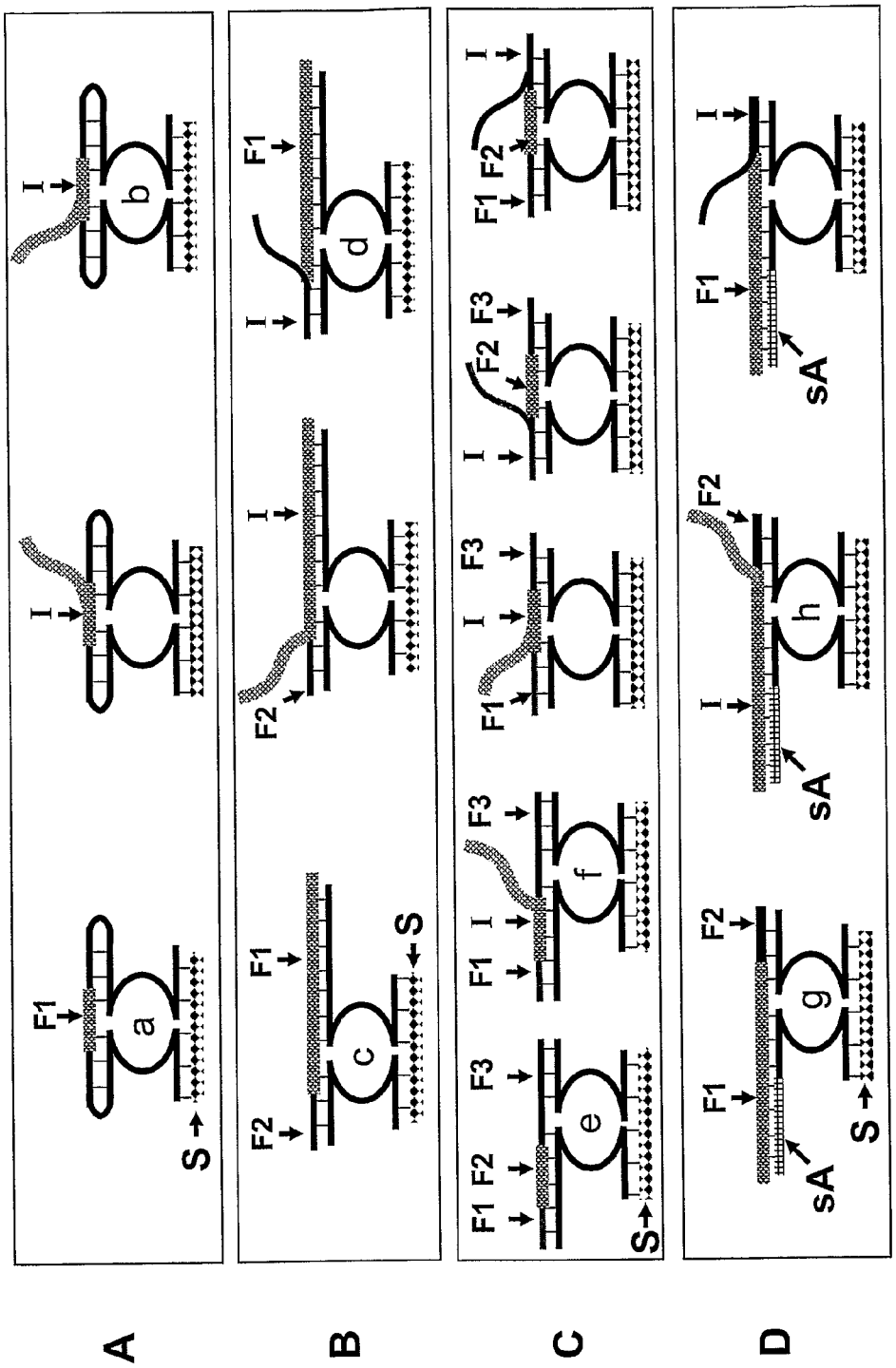

FIG. 9. Exemplary structures for MNAzyme and MNAi designs: Some examples of active MNAzyme structures are shown in Panels A to D (left hand side structures). These structures are all capable of forming catalytically active enzymes, which can cleave the substrate (S). Examples of MNAi structures are shown in Panels A to D (structures to the right of the active MNAzymes). These MNAi structures contain an activity inhibitor (I), which binds to the site which would be occupied by an assembly facilitator (F) in an active MNAzyme. The illustration contains schemes for MNAzymes, which include one assembly facilitator F1 (panel A), two assembly facilitators F1 and F2 (panels B and D) or three assembly facilitators F1, F2 and F3 (panel C). The examples of MNA, which are shown in panel A include sensor arms with self complementary regions within the partzyme sensor arms. MNA structures may also include one or more stabilising arms (sA) as shown in panel D. The specific MNAzyme and MNAi structures labelled a to h may be better understood by reference to examples 7 to 10.

Figure 10:
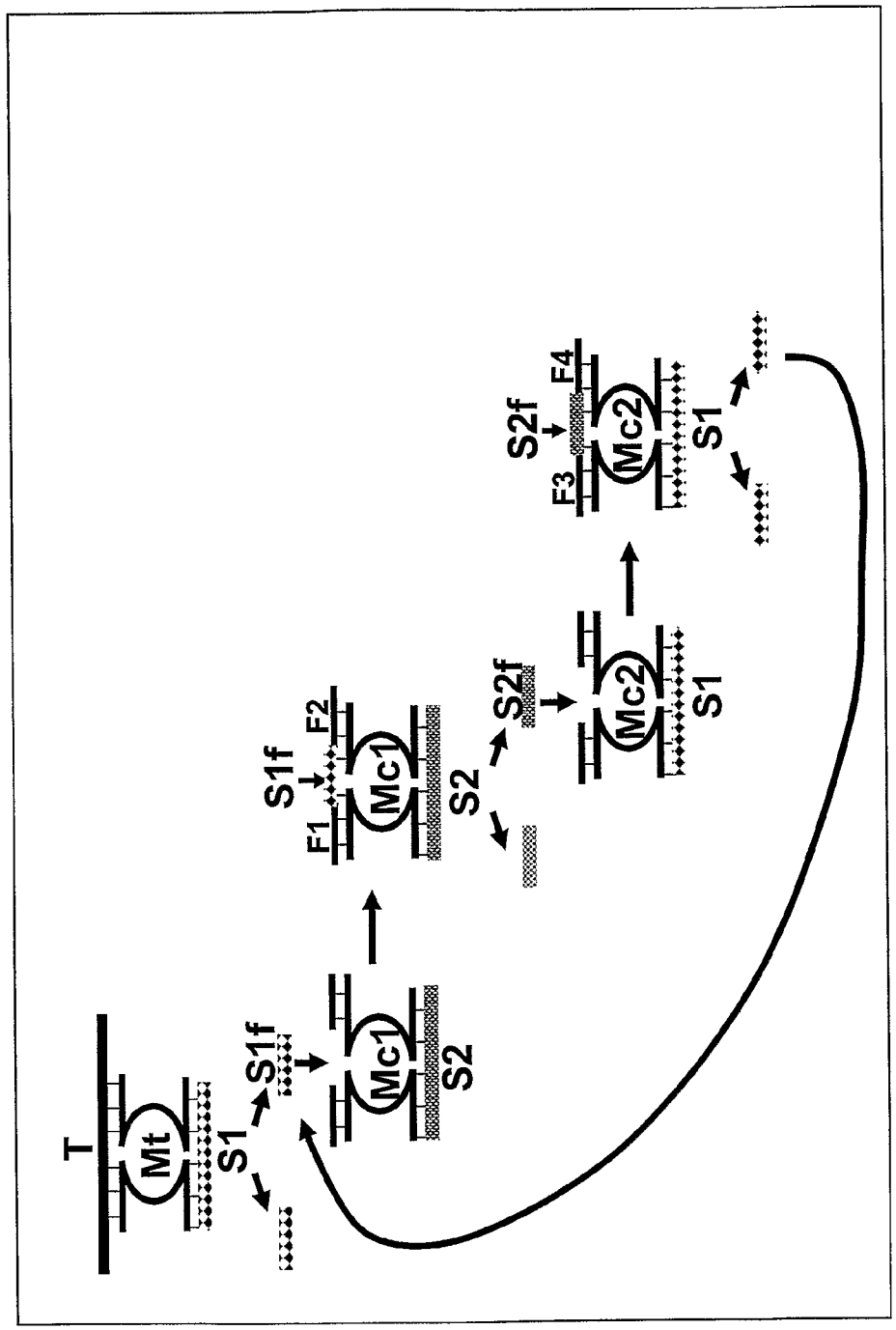

FIG. 10: An exemplary strategy for a cascade using two substrates. In this strategy an initiating MNAzyme (Mt) is formed in the presence of a target (T). The initiating MNAzyme (Mt) cleaves a first substrate (S1) to create a first activator assembly facilitator component (S1f), which directs formation of a first MNAzyme (cascading MNAzyme Mc1). In this example the first MNAzyme (Mc1) comprises two partzymes and three assembly facilitator components designated F1, F2 and S1f. Mc1 can cleave an additional substrate (S2) thus liberating an additional activator assembly facilitator component (S2f), which directs formation of a second MNAzyme (cascading MNAzyme Mc2). In this example the second MNAzyme (Mc2) comprises two partzymes and three assembly facilitator components designated F3, F4 and S2f. Mc2 can then cleave more of the first substrate (S1) thus creating more of the first activator assembly facilitator component (SU). This leads to the formation of further first MNAzyme (Mc1) thereby forming an amplification cascade.

Figure 11:
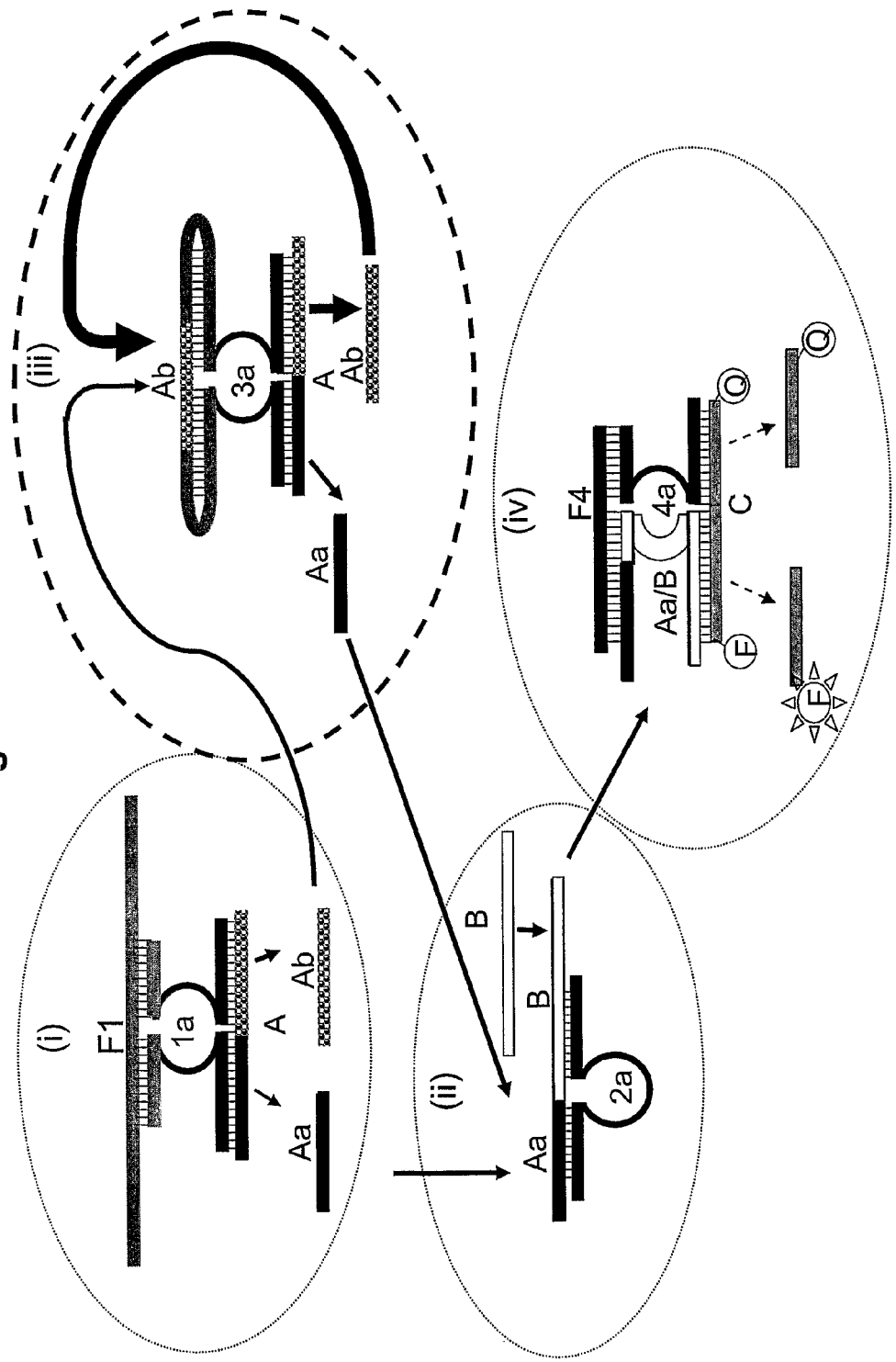

FIG. 11. A signal amplification cascade using an initiating MNAzyme, a SCUD cascade amplification and DNAzyme ligase mediated MNAzyme cleavage readout. The strategy illustrated in this figure has the following features;

(i) A target nucleic acid (F1) facilitates the formation of an initiating MNAzyme (MNAzyme 1a) which cleaves a first substrate (substrate A) and generates a first cleavage product (product Aa) and a second cleavage product (an activator assembly facilitator) (product Ab), the first cleavage product (product Aa) is required as a component in reaction aspect (ii) and the second cleavage product (product Ab) is required as a component in reaction aspect (iii).

(ii) The first cleavage product (product Aa) has a 2',3'-cyclic phosphate at its 3' terminus and is suitable to function as a substrate for DNAzyme 2a, which has ligase activity. DNAzyme ligase 2a ligates the first cleavage product (product Aa) to a second substrate (substrate B) to create a ligated partzyme for an additional MNAzyme (MNAzyme 4a).

(iii) The second cleavage product (product Ab) functions as an activator assembly facilitator component to direct the formation of a second MNAzyme (MNAzyme 3a). The second MNAzyme (MNAzyme 3a) modifies further first substrate (substrate A) generating further first cleavage product (product Aa) and second cleavage product (product Ab). The further second cleavage product (product Ab) then directs the formation of further second MNAzyme (MNAzyme 3a). This results in a SCUD autocatalytic self-replication feedback amplification cascade. This SCUD cascade results in further accumulation of further second cleavage product (product Ab) which functions to assemble more second MNAzyme (MNAzyme 3a), and it results in the accumulation of further first cleavage product (product Aa), which functions as a substrate for DNAzyme 2a in aspect (ii).

(iv) The ligated partzyme for the additional MNAzyme generated in aspect (ii) by ligation of first cleavage product (product Aa) and the second substrate (Substrate B) forms a new partzyme for the additional MNAzyme (MNAzyme 4a). The additional MNAzyme (MNAzyme 4a) forms together with facilitator F4 and modifies substrate C between a fluorophore and quencher dye pair resulting in an increase in fluorescent signal indicative of the presence of target nucleic acid F1.

Figure 12:
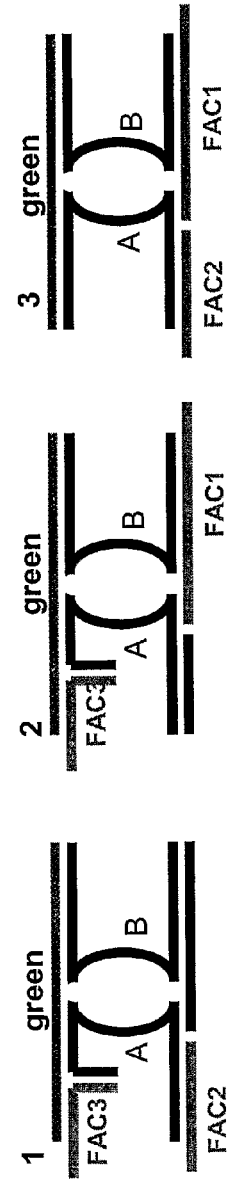
Figure 12:
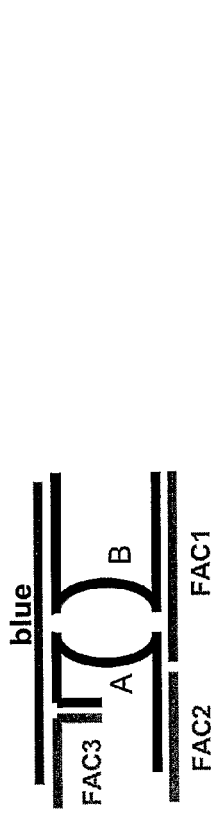
Figure 12:
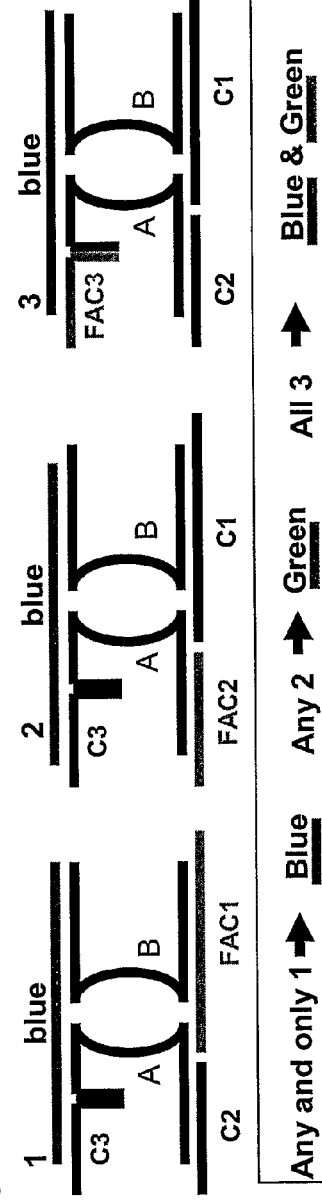

FIG. 12. Molecular Full Adder using MNAzymes. The three inputs, FAC1, FAC2 and FAC3, are shown in grey, the hatched lines designated 'green' and 'blue' represent substrates with different fluorophores, and the C oligonucleotides are displayed in black. The partzymes are also shown in black, and are pre-complexed with the C oligonucleotides and substrate.

DEFINITIONS

Certain terms are used herein which shall have the meanings set forth as follows.

The term "comprising" means "including principally, but not necessarily solely". Further more, variations of the word "comprising", such as "comprise" and "comprises", have correspondingly varied meanings.

The terms "polynucleotide", "nucleic acid" and "oligonucleotide" may be used interchangeably and refer to a single- or double-stranded polymer of deoxyribonucleotide or ribonucleotide bases, or analogues, derivatives, variants, fragments or combinations thereof, including but not limited to DNA, methylated DNA, alkylated DNA, RNA, methylated RNA, microRNA, siRNA, shRNA, mRNA, tRNA, snoRNA, stRNA, smRNA, pre- and pri-microRNA, other non-coding RNAs, ribosomal RNA, derivatives thereof, amplicons thereof or any combination thereof. By way of non-limiting example, the source of a nucleic acid may be selected from the group comprising synthetic, mammalian, human, animal, plant, fungal, bacterial, viral, archael or any combination thereof.

The terms "catalytic nucleic acid molecule", "catalytic nucleic acid", "nucleic acid enzyme" and "catalytic nucleic acid sequence" are used herein interchangeably and shall mean a DNA molecule or DNA-containing molecule (also known in the art as a "DNA enzyme", "deoxyribozyme" or "DNAzyme") or an RNA or RNA-containing molecule (also known in the art as a "RNA enzyme" or "ribozyme") or a combination thereof, being a DNA-RNA hybrid molecule, which may recognize a substrate and catalyse a modification of the substrate. The nucleotide residues in the catalytic nucleic acids may include the bases A, C, G, T, and U, as well as derivatives and analogues thereof.

The terms "multi-component nucleic acid complex", "multi-component nucleic acid", "MNA" or "MNA complex" refer to complexes which comprise two or more components selected from the group comprising but not limited to, partzymes, stabiliser arms, assembly facilitators, substrates, and modulator components including activity inhibitors, assembly inhibitors, and components thereof. In some embodiments the MNA complex is an active MNAzyme. In other embodiments the MNA complex is an inactive complex such as an MNAi may comprise an MNAi which may also be referred to herein as a multi-component nucleic acid inactive proenzyme (MNAi). In yet other embodiments the MNA complex may lack one or more of the components required for assembly and catalysis by an MNAzyme including, but not limited to, a substrate, an assembly facilitator, a stabiliser arm and the partzymes, or components thereof.

Figure 1:
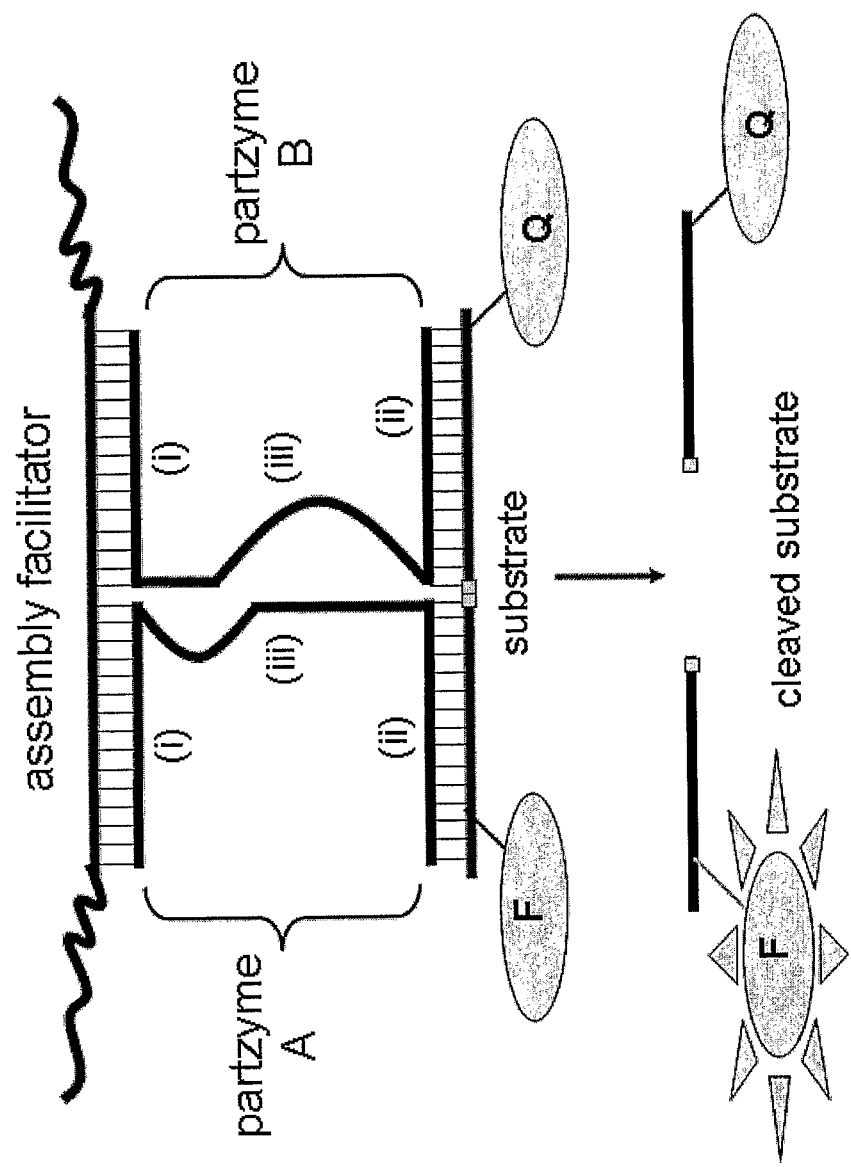
FIG. 1: Depiction of one exemplary design of a Multi-component nucleic acid (MNAzyme). By way of exemplary disclosure, an MNAzyme is composed of two partzymes (A and B), which self assemble in the presence of an assembly facilitator. When the two partzymes assemble in the presence of the assembly facilitator, a catalytically active MNAzyme forms which is capable of modifying, for example cleaving, a substrate. The two component partzymes have (i) sensor arms, which bind to the assembly facilitator, (ii) substrate arms, which bind the substrate, and (iii) partial catalytic core sequences.

The term "MNAzyme" as used herein, refers to two or more oligonucleotide sequences (e.g. partzymes) which, only in the presence of MNAzyme assembly facilitator (for example, a target), form an active nucleic acid enzyme complex that is capable of catalytically modifying a substrate. An exemplary MNAzyme comprising partzyme A and partzyme B is depicted in FIG. 1. With reference to FIG. 1, partzymes A and B each bind to an assembly facilitator (e.g. through Watson-Crick base pairing). The MNAzyme only forms when the sensor arms of partzymes A and B hybridize adjacent to each other on the assembly facilitator. The substrate arms of the MNAzyme engage the substrate, the modification (e.g. cleavage) of which is catalyzed by the catalytic core of the MNAzyme, formed by the interaction of the catalytic domains of partzymes A and B. Cleavage of a DNA/RNA chimeric reporter substrate is exemplified in the drawing. The MNAzyme cleaves the substrate between a fluorophore and a quencher dye pair, thus generating signal. The terms "multi-component nucleic acid enzyme" and "MNAzyme" are used herein interchangeably and comprise bipartite structures, composed of two molecules, or tripartite structures, composed of three nucleic acid molecules, or other multipartite structures, for example those formed by four or more nucleic acid molecules.

Figure 2:
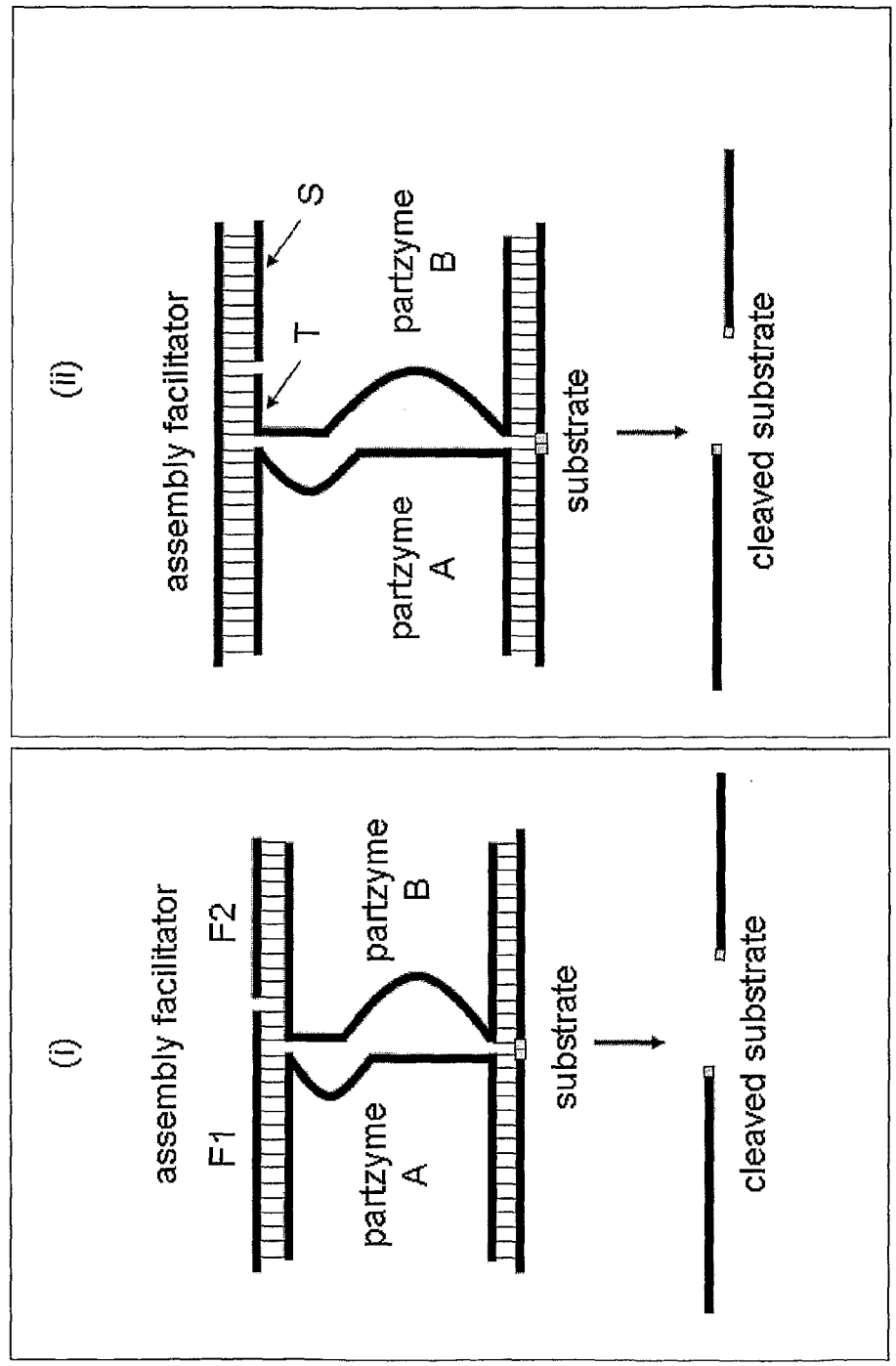
FIG. 2: Additional exemplary designs for active MNAzymes. Panel (i): Depiction of an exemplary design for MNAzymes where multiple assembly facilitator components are required for MNAzyme formation. In this design, one component (F1) of the assembly facilitator is complementary to regions of the sensor arms of both partzyme A and B, whereas a second assembly facilitator component (F2) is complementary to either partzyme B only (as per this illustration), or partzyme A only. The two assembly facilitator components together direct the assembly of an active MNAzyme which can modify (eg cleave) a substrate. Panel (ii): Depiction of an exemplary design where partzyme A component and bi-partite partzyme B components assemble in the presence of assembly facilitator to produce an active MNAzyme capable of modifying (eg cleaving) a substrate. In this diagram, partzyme B has a truncated sensor arm (T), which is insufficient to allow stable MNAzyme assembly in the absence of a second component, referred to as a stabiliser arm component (S). Hybridization of the stabiliser arm to the assembly facilitator in a location adjacent to the truncated sensor arm of the partzyme, allows assembly of an active MNAzyme.

An example of an MNAzyme which is composed of more than two molecules is illustrated in FIG. 2 (ii). A partzyme may comprise multiple components, including but not limited to, a partzyme component with a truncated sensor arm and a stabilizing arm component which stabilises the MNAzyme structure by interacting with either an assembly facilitator (as depicted in FIG. 2 (ii)) or with a substrate.

The term "MNAi" as used herein refers to an MNA complex that is in a catalytically inactive state, wherein catalytic activity is inhibited by an "activity inhibitor" as herein defined. In preferred embodiments, the MNAi may be catalytically inactive due to binding of an activity inhibitor oligonucleotide, for example, as depicted in FIG. 4, which shows an exemplary design for an MNAi. For example, an MNAi may be formed when partzyme A, partzyme B, an assembly facilitator and an activity inhibitor associate to form an inactive complex. Additional examples of MNAi structures are illustrated in FIG. 9.

The terms "catalytically inactive MNA complex", "inactive MNA complex", "catalytically inactive MNA" or "inactive MNA" as used herein refer to multicomponent nucleic acid complexes which are not in a catalytically active state. In one embodiment the "inactive MNA complex" is an MNAi which may be catalytically inactive due to binding of an activity inhibitor oligonucleotide. In another embodiment, the "inactive MNA complex" is a partially assembled or partially disassembled MNA complex where one or more of the components required for catalytic MNAzyme activity are not associated with the MNA complex. In one embodiment the absence of one or more components required for MNAzyme activity from the reaction milieu may result in formation of an "inactive MNA complex". In another embodiment the microenvironment, for example, the temperature may not be compatible with association of all the components required for an active MNAzyme. In another embodiment an "inactive MNA complex" may contain all components necessary for structural formation of an active MNAzyme but the "inactive MNA complex" lacks activity due to the absence of one or more essential ingredients that are required for catalysis such as, for example, a divalent cation. In another embodiment, the inactive MNA complex may be inactive because of the presence of an assembly inhibitor.

The terms "molecular switch" or "switch" as used herein refer to any MNA complex that can transition from an inactive to an active complex, or vice versa, in response to an input event. In preferred embodiments the inactive complex is a catalytically inactive complex. Catalytically inactive complexes may comprise a disassembled complex, a partially assembled complex, or complexes such as an MNAi or a complex with an associated assembly facilitator. Catalytically active complexes may be MNAzymes.

The terms "assembly facilitator molecule", "assembly facilitator", "MNAzyme assembly facilitator molecule", "facilitator", "MNAzyme assembly facilitator" and "activator assembly facilitator" as used herein refer to entities that can facilitate the self-assembly of partzyme components to form a catalytically active MNAzyme by interaction with the sensor arms of the MNAzyme. In preferred embodiments an assembly facilitator is required for the self-assembly of an MNAzyme. In one embodiment, an assembly facilitator may be comprised of one (FIG. 1) or more molecules or components (FIG. 2 (i), FIGS. 4-6 and 9-10) that may pair with, or bind to, the sensor arms of one or more oligonucleotide "partzymes". Assembly facilitators may also associate with MNA complexes which are not catalytically active including, but not limited to, MNAi and partially assembled or disassembled MNA complexes.

Components of an MNA complex may comprise domains which have separate functions to the component as a whole. For example, activator assembly facilitator domains may be contained within other components, e.g. within an activity inhibitor molecule, where they are present in a state whereby they can not contribute to active MNAzyme assembly until liberated from the component by, for example, cleavage. "Activator assembly facilitator" or "activator assembly facilitator components" as used herein refer to entities that, once liberated from within another component, or provided exogenously, can facilitate the self-assembly of partzyme components to form a catalytically active MNAzyme by interaction with the sensor arms of the MNAzyme.

Assembly facilitators, such as activator assembly facilitators, can be used to control the assembly of active MNAzymes or facilitate the transition from inactive multi-component nucleic acid complexes to active MNAzymes. The said multicomponent nucleic acid complexes may be catalytically inactive due to the presence, for example, of an activity inhibitor such as in MNAi.

An "activator" as used herein is any MNA structural or modulator oligonucleotide component, any "molecular effector", "ligand", "target", or "event" that results in activation of MNAzymes. Activator oligonucleotides include, but are not limited to, oligonucleotides that act as assembly facilitators, a partzyme or component thereof, for example those with truncations of the sensor or substrate arm, and partzyme stabiliser arm components.

In other embodiments activators may activate MNAzymes by removing oligonucleotides that exert an inhibitory effect. Examples of oligonucleotides which can activate through such a mechanism include modulator oligonucleotides which can displace (remove) inhibitory components, including but not limited to, an "activity inhibitor" or an "assembly inhibitor".

In other embodiments an "activator" may be a ligand which interacts with an aptamer domain of an MNA complex component wherein the result of the interaction is activation of the MNA complex.

As used herein the term "stabiliser arm" refers to entities that can interact with at least one assembly facilitator in a location adjacent to a sensor arm of a partzyme to allow assembly of an MNA complex including but not limited to an active MNAzyme.

The term "target" as used herein includes any natural or synthetic entity, constituent or analyte which is sought to be detected, identified or quantified by a particular MNA zyme(s), with or without an additional amplification step including but not limited to an MNAzyme amplification protocol, for example, the "Signal Cascade Using DNA" or "SCUD" reaction. Targets therefore encompass the broadest range of detectable entities, constituents or analytes for which methods of sensitive detection, identification and/or quantification are desirable. Some exemplary targets include, but are not limited to, protein, polypeptide, peptide or nucleic acid, glycoproteins, lipids, lipoproteins, entire organisms, cells, viruses, bacteria, archaea, yeast, fungi, antibodies, metabolites, pathogens, toxins, contaminants, poisons, small molecules, polymers, metal ions, metal salts, prions or any derivatives, portions or combinations thereof. Other targets are also contemplated for use herein. It will be understood that the target may also be an assembly facilitator or activator.

As used herein a "detectable event", or "input" or "input event" includes a change in the microenvironment of the MNA complex, including but not limited to, MNAzymes and/or inactive MNA complexes. The change may be, for example, change in temperature, salt concentration, ionic strength, pH, divalent cation presence or absence, type or concentration, electric charge, magnetic charge, physical manipulation and change in concentration of an MNA or modulator component or component of the microenvironment, or any combination thereof. It will also be understood that reference to a "change in the concentration of" includes an increase or a decrease in concentration and also includes the appearance of an entity previously absent or at undetectable concentration in the microenvironment of the MNA complex, including MNAzymes and/or inactive MNA complexes such as MNAi.

Entities which represent detectable events may also be used as "activators" or "inhibitors" of the catalytic activity of MNAzymes since changes in the microenvironment can be used to manipulate catalytic activity of MNA complexes. As such, these entities allow the catalytic activity of MNAzymes to be switched "on" or "off", for example by promoting transition from inactive MNA complexes to active MNAzymes, or vice versa. In some embodiments the entity promotes assembly and activation of MNAzymes. In some embodiments the event or entity promotes disassembly and inactivation of MNAzymes. In other embodiments the event or entity may direct the assembly or disassembly of MNAi or other MNA complexes. In preferred embodiments the process of activation and inactivation of MNAzyme catalytic activity is reversible.

The term "activity inhibitor" refers to any entity that can bind to one or more components of an MNA complex and direct assembly of catalytically inactive "MNAi" (e.g. FIGS. 4-6 and 9-11). The inhibition of catalytic activity by the activity inhibitor may be mediated by an "activity inhibitor domain", also called an "activity inhibitor component", "inhibitor domain", or an "activity inhibitor domain" which is substantially non-complementary to the partzymes. In preferred embodiments, an activity inhibitor may comprise several distinct functional domains, for example, including but not limited to, functional domains in any combination selected from an activity inhibitor domain, an activator assembly facilitator domain, a substrate domain, and/or a reporter domain. Such distinct functional domains may or may not coincide with several distinct structural domains in an activity inhibitor. Accordingly, in some embodiments, an activity inhibitor may comprise an activity inhibitor domain which is substantially non-complementary to the partzyme components and which exerts an inhibitory effect by disrupting the secondary structure required for formation of a catalytically active MNAzyme. The presence of an activity inhibitor drives the assembly of MNAi complexes that are capable of interacting with, but not catalytically modifying, a substrate. In some embodiments, an activity inhibitor may comprise an assembly facilitator domain.

In some embodiments, the activity inhibitor may further include a labile or cleavable linker or substrate, which may for example be located between two or more domains within the activity inhibitor, for example an activity inhibitor domain and an activator assembly facilitator domain. Cleavage at the substrate or linker site may allow separation of an activity inhibitor domain from an activator assembly facilitator domain, which may then function as an assembly facilitator component and direct the assembly of an active MNAzyme.

In some embodiments the activity inhibitor may be conjugated to other entities. In some embodiments the activity inhibitor is conjugated to a gold nanoparticle coupled to a radio-frequency magnetic field to allow remote electronic control of hybridisation. In this approach radio-frequency magnetic fields function as antennas enabling reversible thermal denaturation of specific oligonucleotides, while leaving the surrounding molecules relatively unaffected. In some embodiments the activity inhibitor can be labelled with biotin to facilitate capture and physical isolation of the activity inhibitor.

As used herein, an "assembly inhibitor" is a component which inhibits the assembly of the MNAzyme complex by complementary binding to an essential component of an active MNAzyme complex, for example by binding to a partzyme component or an assembly facilitator or a substrate. The binding of the assembly inhibitor sequence to a first MNAzyme complex component leads to competition between the assembly inhibitor and the said first component for binding to a second MNAzyme complex component. For example, the assembly inhibitor may bind to either a partzyme substrate arm (that binds the substrate) or a partzyme sensor arm (that binds the assembly facilitator). When the assembly inhibitor is complementary to (and bound to) the substrate arm, it competes (and blocks) binding of the substrate to the partzyme (FIG. 7). When the assembly inhibitor is complementary to (and bound to) the sensor arm, it competes (and blocks) binding of the assembly facilitator to the partzyme. In this manner an assembly inhibitor blocks the assembly of MNAzyme complexes. The assembly inhibitor molecule can be used to control the assembly of MNAzymes, and further allows the development of strategies for the detection of both non-nucleic acid and nucleic acid target analytes.

The terms "substrate", "substrate molecule" and "chemical substrate" as used herein include any molecule which is capable of being recognized, acted upon or chemically modified by a molecule such as an MNA complex. The modification of the substrate provides the "output" signal or "detectable effect" for monitoring the activity of the MNA systems. In particular embodiments, a substrate may be recognized and modified by an enzyme. In other embodiments, a substrate may be recognized and modified by a catalytic nucleic acid molecule. In preferred embodiments, a substrate may be recognized and modified by an MNAzyme. The chemical modification of a substrate can be measured by the appearance of, or increase in, a product of the modification reaction, or by the disappearance of, or decrease in, a substrate of the modification reaction(s).

A "reporter substrate", "reporter probe" or "reporter oligonucleotide" as used herein is a substrate that is particularly adapted to facilitate measurement of either the disappearance of a substrate or the appearance of a product in connection with a catalyzed reaction. Reporter substrates can be free in solution or bound (or "tethered"), for example, to a surface, or to another molecule. A reporter substrate can be labelled by any of a large variety of means including, for example, fluorophores (with or without one or more additional components, such as quenchers), radioactive labels, biotin (e.g. biotinylation) or chemiluminescent labels.

As used herein, "generic" or "universal" substrates are substrates, for example reporter substrates, that are recognized by and acted on catalytically by a plurality of MNAzymes, each of which can recognize a different assembly facilitator. The use of such substrates facilitates development of separate assays for detection, identification or quantification of a wide variety of assembly facilitators using structurally related MNAzymes all of which recognize a universal substrate. These universal substrates can each be independently labelled with one or more labels. In preferred embodiments, independently detectable labels are used to label one or more generic substrates to allow the creation of a convenient system for independently or simultaneously detecting a variety of assembly facilitators using MNAzymes. In some embodiments, substrates cleaved by MNAzymes can be reconstituted, and hence recycled, using a DNAzyme ligase.

The term "modulator" as used herein is an entity which can increase or decrease the catalytic activity of an MNA system. Modulators may be "activators", which activate or switch on the activity of an MNAzyme. In some embodiments modulators are "inhibitors", including but not limited to, "assembly inhibitors" or "activity inhibitors".

As used herein an "aptamer" may comprise a structure that has the ability to recognize one or more ligands. For example, the recognition may have a high degree of specificity due to higher level structure of the aptamer, such as a 3-dimensional binding domain or pocket. Aptamers may therefore bind protein, polypeptide, peptide or nucleic acid, glycoproteins, lipids, lipoproteins, cells, viruses, bacteria, archaea, fungi, antibodies, metabolites, pathogens, toxins, contaminants, poisons, entire organisms, small molecules, polymers, metal ions, metal salts, prions or any derivative, portion or combination thereof, or any other entity. Preferred aptamers herein may comprise short single-stranded DNA or RNA oligomers that can be isolated from complex libraries of synthetic nucleic acid by an iterative process of adsorption, recovery, and reamplification. Aptamers may therefore be generated against almost any target, ranging from small molecules such as amino acids, or antibiotics to protein and nucleic acid structures. In the present invention aptamers are used to build molecular switches into MNA systems containing assembly inhibitors. The presence of an activator ligand can switch on the MNAzyme activity (FIG. 7 right hand side) and the removal or absence of an activator ligand can switch off the activity of an MNAzyme (FIG. 7 left hand side). Further, in the present invention aptamers are also used to facilitate detection of nucleic acid and non-nucleic acid ligands. Detection of a ligand can further be used to trigger an amplification cascade, including but not limited to a SCUD amplification cascade.

As used herein, the terms "partzyme", "component partzyme" "partzyme component" and "component oligonucleotide" refer to a DNA-containing or RNA-containing or DNA-RNA-containing oligonucleotide, two or more of which, only in the presence of an MNAzyme assembly facilitator as herein defined, can together form an "MNAzyme." In certain preferred embodiments, one or more component partzymes, and preferably at least two, may comprise three regions or domains: a "catalytic" domain, which forms part of the catalytic core that catalyzes a chemical modification; a "sensor arm" domain, which may associate with and/or bind to an assembly facilitator; and a "substrate arm" domain, which may associate with and/or bind to a substrate. An example depiction of these regions or domains is shown in FIG. 1. Partzymes may comprise at least one additional component including but not limited to an aptamer, referred to herein as an "apta-partzyme".

As used herein the term "full adder" refers to a logical element that performs an operation on three binary inputs, to produce two unique binary outputs. The full adder operations obey the following rules: i) The presence of any and exactly one input produces only a first output; ii) the presence of any and exactly two inputs produces only a second output; iii) the presence of exactly all three inputs produces both the first and second outputs, and; iv) the absence of all three inputs produces no outputs.

As used herein, the term "cascade" refers to any succession of processes or operations that occur in successive stages, wherein the occurrence of each stage is typically dependent on the occurrence of a preceding stage. A cascade may therefore include, but is not limited to, an enzymatic cascade or any other signal transduction cascade. In some embodiments, a cascade may comprise amplification of a signal resulting from catalytic activity of an MNAzyme. In preferred embodiments, such an amplification cascade may involve repeated and therefore cyclic amplification of a signal, wherein catalytic activity of a first MNAzyme makes available a required molecule for catalytic activity of a second MNAzyme, which in turn makes available a required activator for catalytic activity of an additional second MNAzyme. In some embodiments, the required activator may comprise a partzyme, an enzyme, an assembly facilitator, a substrate, a target, a portion or fragment thereof or a combination thereof. In some embodiments, a cascade may therefore involve production of a cumulative effect, and thus detect a target of low abundance by generating a signal to a level at which it may be detected. In other embodiments, more than two catalytic stages may be employed. The cascade may be linear. In a preferred embodiment, the cascade may be exponential. In preferred embodiments, the cascade may involve activation of an MNAi via removal of the influence of an activity inhibitor. In some embodiments, MNA complex components may be created by cleavage of other MNA complex components. In some embodiments, MNA complex components may be created by ligation of other MNA complex components, for example, by using a DNAzyme ligase.

The term "oligonucleotide" typically denotes a segment of DNA or a DNA-containing nucleic acid molecule, or RNA or RNA-containing molecule, or a combination thereof. Examples of oligonucleotides include nucleic acid targets; substrates, for example, those which can be modified by an MNAzyme or DNAzyme; primers such as those used for in vitro target amplification by methods such as PCR; and components of MNA complexes. MNA complex components including, but not limited to assembly facilitators, assembly inhibitors, activity inhibitors, arm stabilisers and/or substrates, in certain embodiments, may comprise oligonucleotides as defined herein. Partzymes as used herein may also comprise oligonucleotides.

The terms "polynucleotide", "nucleic acid" and "oligonucleotide" include reference to any specified sequence as well as to the sequence complementary thereto, unless otherwise indicated. Oligonucleotides may comprise at least one addition or substitution, including but not limited to the group comprising 4-acetylcytidine, 5-(carboxyhydroxylmethyl) uridine, 2'-O-methylcytidine, 5-carboxymethylaminomethyl thiouridine, dihydrouridine, 2'-O-methylpseudouridine, beta D-galactosylqueosine, 2'-O-methylguanosine, inosine, N6-isopentenyladenosine, 1-methyladenosine, 1-methylpseudouridine, 1-methylguanosine, 1-methylinosine, 2,2-dimethylguanosine, 2-methyladenosine, 2-methylguanosine, 3-methylcytidine, 5-methylcytidine, N6-methyladenosine, 7-methylguanosine, 5-methylaminomethyluridine, 5-methoxyaminomethyl-2-thiouridine, beta D-mannosylmethyluridine, 5-methoxycarbonylmethyluridine, 5-methoxyuridine, 2-methylthio-N6-isopentenyladenosine, N-((9-beta-ribofuranosyl-2-methylthiopurine-6-yl)carbamoyl)threonine, N-((9-beta-ribofuranosylpurine-6-yl)N-methyl-carbamoyl) threonine, uridine-5-oxyacetic acid methylester, uridine-5-oxyacetic acid (v), wybutoxosine, pseudouridine, queosine, 2-thiocytidine, 5-methyl-2-thiouridine, 2-thiouridine, 4-thiouridine, 5-methyluridine, N-((9-beta-D-ribofuranosylpurine-6-yl)carbamoyl)threonine, 2'-O-methyl-5-methyluridine, 2'-O-methyluridine, wybutosine, 3-(3-amino-3-carboxypropyl)uridine, beta D-arabinosyl uridine, beta D-arabinosyl thymidine.

The term "derivative" when used in relation to a nucleic acid or nucleotide of the present invention includes any functionally equivalent nucleic acids or nucleotides, including any fusion molecules produced integrally (e.g., by recombinant means) or added post-synthesis (e.g., by chemical means). Such fusions may comprise oligonucleotides of the invention with RNA or DNA added thereto or conjugated to a polypeptide (e.g., puromycin or other polypeptide), a small molecule (e.g., psoralen) or an antibody.

The term "analogue" when used in relation to a nucleic acid or nucleotide includes a compound having a physical structure that is related to a DNA or RNA molecule or residue, and may be capable of forming a hydrogen bond with a DNA or RNA residue or an analogue thereof (i.e., it is able to anneal with a DNA or RNA residue or an analogue thereof to form a base-pair), but such bonding is not so required for said compound to be encompassed within the term "analogue". Such analogues may possess different chemical and biological properties to the ribonucleotide or deoxyribonucleotide residue to which they are structurally related. Methylated, iodinated, brominated or biotinylated residues are examples of analogues. Active DNAzymes have been described which contain nucleotide analogues, including deoxyinosine, C-5-immidazole deoxyuridine, 3-(aminopropynyl)-7-deaza-dATP, 2'-O-methyl RNA, 2' O-methyl cap (Warashina et al., 1999; Cairns et al., 2003; Schubert et al., 2004; Sidorov et al., 2004). Other analogues are compatible with catalytic activity of DNAzymes. Alteration of a catalytic nucleic acid sequence, for example by substitution of one base for another, by substitution of an analogue for a base, or alteration of the sugar component or phosphodiester backbone, can be straight forward for the skilled artisan. For example, alterations can be made during synthesis, or by modification of specific bases after synthesis. Empirical testing of catalytic nucleic acids incorporating alterations such as base changes or base analogues allows for assessment of the impact of the altered sequences, or specific analogues, on catalytic activity. Analogues of the bases A, C, G, T and U are known in the art, and a subset is listed in Table 1.

TABLE 1

Examples of nucleotide analogues useful herein

| Abbreviation | Name |
| --- | --- |
| ac4c | 4-acetylcytidine |
| chm5u | 5-(carboxyhydroxylmethyl)uridine |
| Cm | 2'-O-methylcytidine |
| Cmnm5s2u | 5-carboxymethylaminomethyl thiouridine |
| D | Dihydrouridine |
| Fm | 2'-O-methylpseudouridine |
| Galq | beta, D-galactosylqueosine |
| Gm | 2'-O-methylguanosine |
| I | Inosine |
| i6a | N6-isopentenyladenosine |
| m1a | 1-methyladenosine |
| m1f | 1-methylpseudouridine |
| m1g | 1-methylguanosine |
| Ml1 | 1-methylinosine |
| m22g | 2,2-dimethylguanosine |
| m2a | 2-methyladenosine |
| m2g | 2-methylguanosine |
| m3c | 3-methylcytidine |
| m5c | 5-methylcytidine |
| m6a | N6-methyladenosine |
| m7g | 7-methylguanosine |
| mam5u | 5-methylaminomethyluridine |
| mam5s2u | 5-methoxyaminomethyl-2-thiouridine |
| Manq | beta, D-mannosylmethyluridine |
| mcm5s2u | 5-methoxycarbonylmethyluridine |
| Mo5u | 5-methoxyuridine |
| Ms2i6a | 2-methylthio-N6-isopentenyladenosine |
| Ms2t6a | N-((9-beta-ribofuranosyl-2-methylthiopurine-6-yl)carbamoyl)threonine |
| Mt6a | N-((9-beta-ribofuranosylpurine-6-yl)N-methyl-carbamoyl)threonine |
| Mv | Uridine-5-oxyacetic acid methylester |
| o5u | Uridine-5-oxyacetic acid (v) |
| Osyw | Wybutoxosine |
| P | Pseudouridine |
| Q | Queosine |
| s2c | 2-thiocytidine |
| s2t | 5-methyl-2-thiouridine |
| s2u | 2-thiouridine |
| s4u | 4-thiouridine |
| T | 5-methyluridine |
| t6a | N-((9-beta-D-ribofuranosylpurine-6-yl)carbamoyl)threonine |
| tm | 2'-O-methyl-5-methyluridine |
| Um | 2'-O-methyluridine |
| Yw | Wybutosine |
| X | 3-(3-amino-3-carboxypropyl)uridine, (acp3)u |
| AraU | beta D-arabinosyluridine |
| AraT | beta D-arabinosylthymidine |

The term "stringency" as used herein refers to the conditions under which two nucleic acids may be hybridized, and may include, for example, the concentration of salts and/or detergents in a solution, the temperature of a solution that is used during the hybridization of the two nucleic acids and time period of the hybridization. Accordingly, the term "high stringency" as used herein refers to conditions in a solution that are conducive to hybridization of two nucleic acids only where such nucleic acids share a high degree of complementarity. The degree of complementarity may include, but not be limited to, a range of from about 50% to 100% Thus, "high stringency" conditions may involve, but are not limited to, the use of a varying temperature and a buffer comprising various concentrations of detergents, salts, and divalent cations.

The following abbreviations are used herein and throughout the specification:
MNA: multi-component nucleic acid, or multipartite nucleic acid;
MNA complex: multi-component nucleic acid complex, or multipartite nucleic acid complex;
MNAzyme: multi-component nucleic acid enzyme, or multipartite nucleic acid enzyme;
MNAi: multi-component nucleic acid inactive pro-enzyme complex, or multipartite nucleic acid inactive pro-enzyme complex;
DNAzyme: deoxyribonucleic acid enzyme;
PCR: polymerase chain reaction;
LCR: ligase chain reaction;
LNA: locked nucleic acid;
PNA: peptide nucleic acid;
An: analyte or target;
F: fluorophore;
Q: quencher;
FAM or 6-FAM: 6-Carboxyfluorescein.
BHQ1: Black Hole Quencher 1
BHQ2: Black Hole Quencher 2
shRNA: short hairpin RNA
siRNA: short interfering RNA
mRNA: messenger RNA
tRNA: transfer RNA
snoRNA: small nucleolar RNA
stRNA: small temporal RNA
smRNA: small modulatory RNA
pre-microRNA: precursor microRNA
pri-microRNA: primary microRNA
SCUD: Signal Cascade using DNA
TASC: target-assisted self cleavage
RIF: Reporter-Inhibitor-Facilitator
RI: Reporter-Inhibitor domain
GTP: guanosine 5'-triphosphate
CTP: cytosine 5'-triphosphate
dATP: deoxyadenosine 5'-triphosphate
ATP: adenosine 5'-triphosphate
LP: ligation product
CP: cleavage product
oligo: oligonucleotide

DETAILED DESCRIPTION OF ILLUSTRATIVE EMBODIMENTS

It is to be understood at the outset, that the figures and examples provided herein are to exemplify, and not to limit the invention and its various embodiments.

In accordance with the present invention, compositions, methods and kits are provided for the modulation of MNA complexes. The methods generally comprise the use of compositions comprising multi-component or multipartite nucleic acid complexes which are preferably formed by multiple nucleic acid components that self assemble to form catalytically active or inactive nucleic acid complexes in the presence of an assembly facilitator.

In accordance with the present invention an alternative to linking MNAzyme detection to target amplification (eg PCR) is to combine it with signal amplification, preferably using only nucleic acid enzymes. Such signal cascade reactions could replace target amplification technologies such as PCR. Further, diagnostic protocols can be developed which do not require any protein enzymes and hence are cheaper and have longer shelf lives.

In accordance with the present invention several strategies for signal cascades, which use MNAzymes, plus or minus DNAzymes, have been conceived.

1. Compositions—MNAzymes and Inactive MNA Complexes

The Multi-component Nucleic Acid enzymes (also referred to herein as multipartite nucleic acid enzymes or "MNAzymes") are described in detail in U.S. application Ser. Nos. 60/726,291 filed Oct. 13, 2005 and 60/724,567 filed Oct. 7, 2005 and in international application PCT/AU2006/001473, the contents of which are all incorporated herein by reference. As defined herein MNAzymes are a class of MNA complexes. MNAzymes are capable of self-assembling from two or more oligonucleotide components, also referred to herein as partzymes. The partzyme oligonucleotides self-assemble in the presence of an assembly facilitator to form an MNA complex. MNAzymes are catalytically active MNA complexes. In some embodiments, the presence of an MNAzyme can be detected, and is indicative of the presence of a target, because the MNAzyme forms only in the presence of the target, wherein the target comprises the assembly facilitator. A wide variety of assays based on the basic principles outlined above are provided herein. Compositions comprising oligonucleotides capable of forming MNAzymes, and MNAzymes of various sequences are also provided herein. In some embodiments at least one of the oligonucleotide components, assembly facilitator or substrate may comprise an aptamer which is capable of binding to an activator or target.

An exemplary design of an MNAzyme is shown in FIG. 1. The assembly facilitator molecule provides the "input" signal which directs the assembly of partzyme components in a highly specific fashion which is amenable to modulation. In some embodiments, the assembly facilitator may be, for example, a target nucleic acid sequence present in a test sample. In other embodiments, the assembly facilitator may be, for example a synthetic oligonucleotide included in the milieu to direct the self-assembly of the partzyme components in the presence of a detectable entity or event. Modification of the substrate by the assembled MNAzyme can provide an "output" signal which may be detected and/or quantified. By way of example only, when the substrate is dual labelled with a fluorophore (F) and a quencher (Q), cleavage of the substrate by an active MNAzyme separates the fluorophore and the quencher resulting in a concomitant increase in fluorescence.

MNAzymes as previously disclosed were contemplated for the detection, identification and quantification of target analytes. The present invention describes new methods, compositions and applications for MNA complexes. The invention describes new compositions which provide oligonucleotide components that can be used to manipulate the activity of MNAzymes by forming alternative structures which lack catalytic activity such as disassembled or partially assembled complexes. The present invention also discloses inactive MNA complexes such as MNAi's, which comprise oligonucleotide components, which would be capable of being assembled into active MNAzymes under appropriate conditions, but which when assembled with an "activity inhibitor" result in the formation of complexes which are catalytically inactive. Such inactive MNA complexes are defined herein as "MNAi", and such inactivity may result from the exertion of an inhibitory influence by an activity inhibitor. MNAi can interact with the substrate via the substrate arms of the partzyme components, but cannot catalytically modify the substrate.

The activity inhibitor may further comprise at least one of an assembly facilitator domain, an activity inhibitor domain, a reporter domain, a substrate domain or any combination thereof. The activity inhibitor may comprise an activator assembly facilitator domain and an activity inhibitor domain. The activity inhibitor may comprise an activator assembly facilitator domain, an activity inhibitor domain and a reporter domain. At least two of the activity inhibitor domain, the activator assembly facilitator domain, substrate domain and the reporter domain may be located on distinct domains of the activity inhibitor. At least two of the activity inhibitor domain, the activator assembly facilitator domain and the reporter domain of the activity inhibitor may be linked by a labile linker or cleavable substrate.

The activity inhibitor domain may comprise a nucleotide sequence substantially non-complementary to at least one MNA component, including partzymes.

The substrate may comprise at least one activator assembly facilitator domain, an activity inhibitor domain and a reporter domain, or any combination thereof.

The activity inhibitor may further comprise at least one assembly inhibitor.

The assembly facilitator domain may be an activator assembly facilitator domain. The activity inhibitor may also comprise an activator assembly facilitator domain and an activity inhibitor domain. This scenario is illustrated by the activity inhibitor depicted in FIG. 4. The activity inhibitor may comprise an activator assembly facilitator domain, an activity inhibitor domain and a reporter domain, for example, the RIF molecule illustrated in FIG. 6. In the case of the RIF molecule at least two of the activity inhibitor domain, the activator assembly facilitator domain and the reporter domain may be located on distinct domains of the activity inhibitor.

With reference to the RIF molecule depicted in FIG. 6 at least two of the activity inhibitor domain, the activator assembly facilitator domain and the reporter domain are linked by a labile linker or cleavable substrate.

The invention also discloses that the inhibition of catalytic activity may be removed upon the occurrence of a particular event, for example, including but not limited to the presence of an activator such as an assembly facilitator as herein defined, or a change in parameter including but not limited to a change in temperature, wavelength, pressure, concentration of salt, detergent, cations or any other parameter. Further, the MNA components, including for example an activity inhibitor, may incorporate additional entities to facilitate removal by physical means which may include, but are not limited to, attached nucleic acids, nanoparticles, microparticles, proteins, antibodies, RNA, DNA, nucleic acid analogues, biotin groups, glycoproteins, lipoproteins, peptide nucleic acids, locked nucleic acids, peptide-nucleic acid chimeras, radiofrequency moieties, or any combination thereof. A catalytically inactive MNA complex represents an "off" state, whereas the catalytically active MNAzyme represents an "on" state.

An activator may directly or indirectly induce the active state. For example, direct induction of the active state may occur when an assembly facilitator component (activator) interacts with the partzymes. For example, indirect induction of the active MNAzyme state may occur through the action(s) of one or more intermediates, such as where an activator comprises or consists of an agent which acts upon an inhibitor to cause removal of an activity inhibitor, such as by release of an inhibitor domain of an activity inhibitor consisting of an inhibitor domain and an assembly facilitator domain. In other embodiments the activator removes the assembly inhibitor.

In preferred embodiments, the MNA complexes, including MNAzymes and inactive MNA complexes are based on one or more DNAzymes and/or ribozymes. More preferred partzyme components for MNAzyme and inactive MNA complexes are based on a particular DNAzyme structure. Presently preferred structures are based on DNAzymes including the 10:23 and 8:17 DNAzymes. In various embodiments the MNAzymes and inactive MNA complexes comprise either or both ribonucleotide bases and deoxyribonucleotide bases. In more preferred embodiments, MNA complexes, including an MNAzyme and inactive MNA complexes are based at least in part on the structure of a DNAzyme. In other preferred embodiments, MNA complexes, including MNAzymes and inactive MNA complexes comprise at least some deoxyribonucleotide bases or analogues thereof. In more preferred embodiments, the catalytic core portions of partzymes assembled into an MNAzyme and/or inactive MNA complexes comprise one or more deoxyribonucleotide bases or analogues thereof. In still more preferred embodiments, one or more deoxyribonucleotide bases or analogues thereof are involved in the catalysis of a substrate by an MNAzyme. In other embodiments, at least one deoxyribonucleotide base, or its analogue, in the catalytic core improves catalytic activity of an MNAzyme. In yet other embodiments, there is a strict requirement for at least one deoxyribonucleotide base, or its analogue, in the catalytic core of the MNAzyme for catalysis to occur at a measurable rate, relative to that of a comparable MNAzyme without the deoxyribonucleotide base present, once the inhibitory influence of an activity inhibitor has been removed.

As provided herein, MNA complexes, including MNAzymes and inactive MNA complexes may contain one or more substitutions such as analogues, derivatives, modified or altered bases, ribonucleotides, alterations of the sugar or phosphate backbone, various deletions, insertions, substitutions, duplications or other modifications, or any combination of these, well known to those skilled in the art. Such modifications, substitutions, deletions, insertions, etc may be made in the sensor and/or substrate arms and/or in the catalytic core portions, as demonstrated herein, such that the molecule retains catalytic activity. Substitutions and modifications to arms that bind the substrate or assembly facilitator may be well tolerated and in fact are the basis of allowing tailoring of the molecules to different substrates/assembly facilitators. For example, modification of the sensor arms will allow tailoring to different assembly facilitators, while modification of the substrate arms will allow tailoring to different substrates. Analysis of multiple generic substrates allows the simultaneous monitoring of multiple "output" signals.

In certain preferred embodiments, the invention envisages MNAzymes with catalytic activity that are comprised of deoxyribonucleotides or which are derived from such molecules by certain modifications/substitutions etc. As a general rule, replacement of the whole molecule with, for example, ribonucleotides, will render the molecule inactive because it relies for its activity on certain key deoxyribonucleotides. In a corresponding fashion, some ribonucleotides in a ribozyme may be substituted with deoxyribonucleotides but replacement of the whole molecule with, for example, deoxyribonucleotides, will render the molecule inactive.

The skilled artisan will appreciate that MNA complexes, including MNAzymes and inactive MNA complexes comprise either deoxyribonucleotides or ribonucleotides, or even both. Those MNAzymes and inactive MNA complexes comprising at least one and more preferably, all, deoxyribonucleotide component oligonucleotides are presently preferred. Also preferred are those MNAzymes and inactive MNAs comprising at least one deoxyribonucleotide base, or its analogue, within at least one of partial catalytic cores of the partzymes comprising the MNAzyme and/or inactive MNA complexes. Even more preferred are those embodiments where such a base is required for catalytic activity of an MNAzyme.

In certain preferred embodiments at least one component of an MNA complex may comprise a region of self-complementarity that may under some conditions form a hairpin structure. In one embodiment a region of self complementarity may be located in one or both of the partzyme sensor arms. In another embodiment the region of self complementarity may be located in one or both of the partzyme substrate arms. In another embodiment a region or regions of self complementarity may be present in an assembly facilitator, an assembly inhibitor or an activity inhibitor component, or any combination thereof. In other embodiments MNA complexes may bind substrates which contain regions of self complementarity.

The skilled artisan will also appreciate that multipartite DNAzymes have advantages over multipartite ribozymes, for example with respect to stability and ease of use. It is also to be appreciated that in certain embodiments, MNAzymes offer advantages over uni-molecular nucleic acid enzymes, for example DNAzymes, which can only recognize one substrate, whereas a single MNAzyme (and/or inactive MNA complex) can recognize two molecules, namely an assembly facilitator and a substrate. For example, these properties of MNAzymes make them adaptable for systems that require the components to be able to "read" an "input" signal and "write" an "output" signal, for example in systems employing logic gates. This property of MNAzymes provides the ability to transduce information, for example, to receive an input signal and respond with an appropriate output response.

2. Methods for Regulating the Catalytic Activity of MNA Complexes and Applications for their Use.

MNA complex assembly and disassembly may be controlled by changing the microenvironment. Examples of such changes include, but are not limited to, temperature, divalent cation type and concentration, salt concentration, pH, additives, and the presence or absence of critical components essential for assembly and/or activity of an active MNAzyme.

The assembled MNAzyme represents an "on" state, whereas its disassembled or partially assembled components represent an "off" state. The assembly and disassembly can be controlled by temperature. The "on" state can be induced by switching the temperature to one within the range that is compatible with both assembly and catalytic activity of an MNAzyme. Conversely, the "off" states can be induced by switching the temperature to outside the range that is compatible with either assembly and/or catalytic activity of an MNAzyme. The melting temperatures of the components of MNA complexes can be adjusted to only allow assembly within a restricted temperature range. Oligonucleotides, which are particularly useful in this aspect of the invention, include but are not restricted to, stabilizer arm components, partzyme components with truncated sensor arms and components of assembly facilitator and/or modulator oligonucleotides. Great flexibility is afforded by MNA complexes in which the components of the basic design (FIG. 1) have been further split into smaller component subunits or portions such as the truncated sensor arm or stabiliser arm portion depicted in FIG. 2, the sequences of which can be tailored with respect to the melting temperature, the sequence composition and complementarity, or lack thereof, with other component oligonucleotides. With reference to FIG. 2 it would be appreciated by one skilled in the art that the partzyme arm, which is truncated, could be any of the following; the partzyme A sensor arm, the partzyme B sensor arm (as illustrated in FIG.

2), the partzyme A substrate arm or the partzyme B substrate arm, or a combination thereof.

The sensitivity of an MNAzyme to temperature can be exploited to build thermo-sensors and rheostats. If the temperature were either too high, or too low, for the assembly (hybridization) of the component oligonucleotides, and/or for catalytic activity, then the MNAzyme substrate would not be modified (eg cleaved). If the temperature were permissive for MNAzyme activity then the substrate would be modified and a signal would be generated. A rise or fall in temperature from one that is incompatible with MNAzyme activity, to another which is compatible with MNAzyme activity, would be detected by a signal generated following substrate modification by the MNAzyme. MNAzymes can thus provide a device capable of detecting temperature changes. One skilled in the art would appreciate that the invention of simple devices using MNAzymes for temperature sensing could be applied in many industries including, for example, the pharmaceutical, food and agricultural industries In other embodiments, a magnetic force can regulate cation concentration and hence provide a switch for modulating MNAzyme activity on and off. Positively charged cations are required for the catalytic activity of some MNAzymes. A magnetic force could alternatively switch the MNAzyme activity off by physically separating the negatively charged partzyme components from the positively charged cations, for example $Mg^{2+}$. The MNAzyme could then be switched back on by allowing the partzymes and cations to come back in contact.

In some embodiments the active "on" states (MNAzyme) can be induced using a pH within the range that is compatible with activity. Conversely, an "off" state can be induced using a pH outside the range that is compatible with activity. pH may further be used to control activity of MNA complexes by inducing hydrolysis of labile sequences, and thus either creating or destroying a new component for an MNAzyme and/or inactive MNA complex.

The presence or absence of any component of the MNA complexes can provide either an "on" or "off" switch. Changing, for example, the oligonucleotide sequence, the melting temperature and or concentration can achieve finer regulation. The broad scope for designs of components which can assemble into MNA complexes, for example two-part assembly facilitators and/or two-part partzyme components (with truncated sensor domains and stabilizer arms), introduces flexibility into systems which can allow tailoring (fine tuning) of conditions compatible with hybridization and hence MNA complex assembly. Further, the hybridization strength and stringency of binding of specific oligonucleotides within an MNA complex is affected by many factors, including but not limited to, salt concentration, cation concentration, temperature and the presence or absence of additives (eg DMSO). As such, entities that affect hybridization can provide a tool for controlling the assembly and disassembly of MNA complexes including active MNAzymes and inactive MNAs.

Physical manipulation of components can be achieved, for example, by exploiting either physical properties of attached moieties as molecular "hooks", and/or by exploiting inherent properties of the oligonucleotides, for example, negative charge, or sequence complementarity. In another embodiment, the attached moiety allows oligonucleotides to be selectively captured, for example using a biotin group. In another embodiment the moiety contains a radio-frequency magnetic field radio to facilitate remote electronic control of hybridisation. This approach is designed to allow the selective removal of component molecules by targeted thermal denaturation of specific oligonucleotides within an MNA complex, thus allowing activation, or inhibition, of enzymatic activity depending on whether the component molecule is itself an activator or an inhibitor sequence. For example, the activity inhibitor can be selectively denatured from an MNAi complex, allowing transition to the active MNAzyme state.

Other strategies can be used to remove the influence of an activator or inhibitor molecule and thus promote assembly or disassembly of active MNAzymes and inactive MNA complexes. For example, hybridization between two oligonucleotides at single stranded termini can cause DNA branch migration and unzipping of regions of double stranded nucleic acid. In one embodiment, an activity inhibitor can be removed from an MNAi complex by modulator oligonucleotide which functions by branch chain migration.

In other embodiments, complementary oligonucleotides can be used to out-compete and hence switch "off" or shut down oligonucleotide components, which in themselves may comprise either activated (MNAzyme) or inactive MNA complexes, such as MNAi. The components which are inhibited by this approach may comprise activator or inhibitor components of either MNAzyme or inactive MNA complexes.

Removal or inhibition of an activator assembly facilitator domain may permit transition of a catalytically active MNAzyme to an inactive MNA complex, such as an MNAi. Removal of an activator assembly facilitator domain may comprise displacement of an activator assembly facilitator domain from an MNAzyme by an activity inhibitor.

The skilled artisan will recognize that the various methods provided herein can generally be used to modulate the assembly or activity of single MNA complexes or of multiple MNA complexes in a single reaction or assay.

3. Use of the Compositions as Molecular Switches

Persons skilled in the art will recognize and understand that the present invention may be equated with a molecular or biological "switch", the applications of which are herein contemplated. Exemplary examples of mechanism for switching on and off MNAzyme activity are listed in Table 2 below.

TABLE 2

Active and inactive MNA states and mechanisms for switching between the two states.

| Type | "On" active state | "Off" inactive state | Example of a mechanism, which can induce transition between active and inactive states. |
|---|---|---|---|
| MNAzyme complex assembly and disassembly | Fully assembled | Fully or partially disassembled | Temperature may be compatible or incompatible with assembly Physical removal or addition of components |

TABLE 2-continued

Active and inactive MNA states and mechanisms for switching between the two states.

| Type | "On" active state | "Off" inactive state | Example of a mechanism, which can induce transition between active and inactive states. |
|---|---|---|---|
| Apta-MNAzyme complex (with assembly inhibitor) | Activator ligand present | Activator ligand absent | Activator ligand provides a switch by removing an assembly inhibitor |
| | Assembly inhibitor removed | Assembly inhibitor provided | Removal, displacement or modification of the assembly inhibitor e.g. by branch chain migration |
| Alternate MNA complex structures | MNAzyme | MNAi | Removal, displacement or modification of the activity inhibitor e.g. by branch chain migration or cleavage |
| Catalysis Inhibition | MNAzyme plus cation e.g. $Mg^{2+}$ | MNAzyme minus cations e.g. $Mg^{2+}$ | Separation of positive cations from negative charged DNA MNA components using for example, magnetic force |

In this regard, the presence or absence of any component of the multi-component nucleic acid complexes can provide either an "activator" or "on" switch or it may provide an inhibitory "off" switch.

In some embodiments, the presence or addition of a stabilizer arm can provide an "on" switch. In one embodiment, new stabilizer arms can be generated in the system during a reaction, for example by cleavage of an activity inhibitor, or any other MNA component. In other embodiments the absence, modification or removal of a stabilizer arm can provide an "off" switch.

In some embodiments, the presence of an assembly facilitator, or a component thereof, can provide an "on" switch. In some embodiments, new assembly facilitators can be generated by MNAzyme cleavage of MNA complex components, for example, by cleavage of activity inhibitors during SCUD or by modification of other components provided in the reaction milieu. In some embodiments, the assembly facilitators can provide specific "input" signal systems, encoded within the sequence. In some embodiments the assembly facilitator can be recognized or "read". In some embodiments, the partzyme sensor arm can "read" assembly facilitator sequences including those differing by one or more single bases. In other embodiments, the absence or removal of an assembly facilitator, or a component thereof, can provide an "off" switch.

In some embodiments components for MNA complexes may be generated by ligation of components present in the reaction milieu. In some embodiments a partzyme is created by ligation of oligonucleotides thereby generating a new partzyme component which can associate to form, for example, an active MNAzyme. In some embodiments an assembly facilitator is created by ligation of oligonucleotides thereby generating a new assembly facilitator component which can facilitate assembly of an MNA complex.

Transition between states of activation (MNAzyme) and inactivation (inactive MNA) can provide a mechanism for creating a molecular switch, which can be regulated by alternating between the active and inactive conformations. Such molecular switches may, for example, be applied to the control of nucleic acid replication cascades, or to the regulation of autonomous therapeutic, diagnostic and computational molecular scale devices.

The present invention provides compositions comprising the components for self-assembling MNAi complexes that self-assemble in the presence of one or more MNAzyme assembly facilitator molecules to form MNAi, wherein at least one assembly facilitator molecule comprises an activity inhibitor.

The invention may be better understood by reference to the figures. FIG. 1 depicts an example of a basic method for assembling an MNAzyme using an assembly facilitator. More specifically, partzyme A and partzyme B are shown in FIG. 1, each comprising a (i) sensor arm portion, (ii) a substrate arm portion, and (iii) a catalytic core portion. In the presence of an assembly facilitator, the sensor arm portions of partzyme A and partzyme B can hybridize to, and base pair with complementary portions of the assembly facilitator, for example a DNA or RNA sequence. Upon contacting the assembly facilitator in this fashion, the MNAzyme self-assembles forming a catalytic core which can modify a substrate which is bound by the substrate arms. Preferably the presence of the MNAzyme is detected through the detection or measurement of its catalytic activity. The substrate arms of the thus assembled MNAzyme can engage a substrate, for example the reporter substrate shown in FIG. 1, through the interaction of the complementary sequences on the substrate arms and the substrate. Once the substrate is so engaged with the substrate arms, the catalytic core can promote the modification (eg. cleavage) of the substrate, which can in turn be measured or detected, directly or indirectly. The MNAzyme can be alternatively assembled (switched on) and dissembled (switched off) using various methods.

With reference to FIG. 2, additional exemplary designs for active MNAzymes are shown. The exemplary structure for one MNAzyme is depicted in panel (i) where multiple assembly facilitator components are required for formation of an MNAzyme. In this design, one assembly facilitator component (F1) is complementary to regions of the sensor arms of both partzyme A and B, whereas a second assembly facilitator component (F2) has complementarity with either partzyme B only (as per FIG. 2 (i)), or partzyme A only. The two assembly facilitator components together direct the assembly of an active MNAzyme which can modify (eg cleave) a substrate. FIG. 9 (left hand structures) illustrates other designs for facilitators for assembly of MNAzymes.

Panel (ii) of FIG. 2 depicts an exemplary design where the assembly of partzyme A with a bi-partite partzyme B component in the presence of assembly facilitator produces an active MNAzyme capable of modifying (eg cleaving) a substrate. In this design, partzyme B has a truncated sensor arm (T), which is insufficient to allow stable MNAzyme assembly in the absence of a second component, referred to herein as a stabiliser arm component (S). However, when a stabiliser arm component hybridises to the assembly facilitator in a location adjacent to that where the truncated sensor arm of the partzyme binds, this allows assembly into an active MNAzyme.

The active MNAzyme formed by the assembly of a partzyme A, a partzyme B component with a truncated sensor arm, and stabiliser arm component in the presence of an assembly facilitator represents an "on" state. Omission, removal or modification of either the partzyme stabiliser arm component, or an assembly facilitator component, results in catalytically active "off" state. As such, the MNAzyme catalytic activity can be regulated by the presence or absence of various oligonucleotides and/or by the ability of such oligonucleotide components to be functionally active, for example to be capable of hybridizing with other oligonucleotide components to form stable MNAzyme complexes. The truncated arm is designed to be insufficient to allow stable MNAzyme assembly under the reaction conditions, unless accompanied by a stabiliser arm component. The stabiliser arm component, and the assembly facilitator, can thus function as "on" switches for MNAzyme activity.

Figure 3:
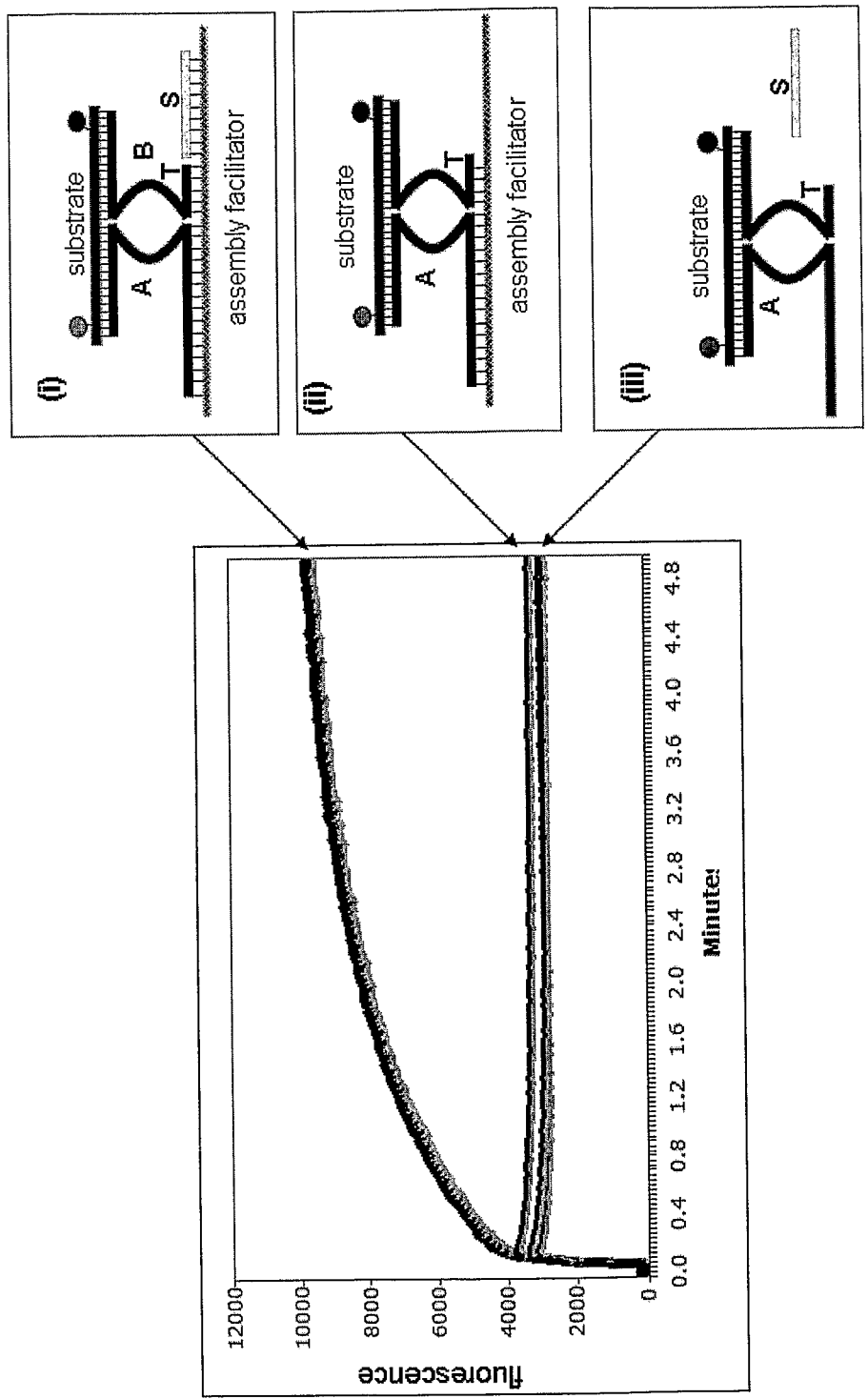
FIG. 3: Changes in output signal (fluorescence) over time in the presence of active and inactive multicomponent nucleic acid complexes. In this example, the first partzyme (A) is of standard design. The second partzyme (B) has one component containing a substrate arm, a partial catalytic core and a truncated sensor arm (T), and a second component which serves as a stabiliser arm (S).

The reactions illustrated in FIG. 3 represent two alternate states for the MNA complexes. The active MNAzyme (reaction (i)) represents the "on" state. Those reactions where either a partzyme stabiliser arm component (reaction (ii)), or an assembly facilitator component (reaction (iii)) is omitted, are inactive MNA complexes representative of "off" states. As such, the MNAzyme catalytic activity can be regulated by the presence or absence of various oligonucleotides and/or by the ability of such oligonucleotide components to be functionally active, for example to be capable of hybridizing with other oligonucleotide components to form stable MNAzymes. The truncated arm is designed to be insufficient to allow stable MNAzyme assembly under the reaction conditions, unless accompanied by a stabiliser arm component. The stabiliser arm, and the assembly facilitator, can function as "on" switches for MNAzyme activity.

It would be appreciated by one skilled in the art that the partzyme arm, which is truncated, could be any of the following; the partzyme A sensor arm, the partzyme B sensor arm (as illustrated), the partzyme A substrate arm or the partzyme B substrate arm.

One skilled in the art would recognise that MNAzymes can be used in strategies for creating molecular sensors, molecular switches, and/or modulators or propagators of autocatalytic self-replicating cascades and other iterative processes. Potential areas of use include, but are not limited to, medical, veterinary, agricultural, food technology, imaging and bioterrorism applications.

With reference to FIG. 4, an MNAi is formed when partzymes A and B complex with an assembly facilitator and an activity inhibitor (left hand panel). The MNAi is capable of interacting with, but not catalytically modifying, the substrate. In some embodiments, the activity inhibitor may further include a labile or cleavable linker, which may separate two or more domains within the activity inhibitor. Such domains may include, for example, (i) an activity inhibitor domain which is substantially non-complementary to the partzyme components and which exerts an inhibitory effect by disrupting the secondary structure required for formation of a catalytically active MNAzyme and (ii) an activator assembly facilitator domain which, if separated from the inhibitor domain, may function as an additional assembly facilitator component and direct the assembly of an active MNAzyme.

An active MNAzyme (FIG. 4, right hand side) can be derived from the components of the MNAi, following modification of the activity inhibitor such as to bisect the molecule and separate the (i) inhibitor domain and the (ii) activator assembly facilitator domain. The released activator assembly facilitator domain is then able to function as a second assembly facilitator component, which in concert with the first assembly facilitator component, can direct the assembly of partzyme components A and B into an active MNAzyme capable of catalytically modifying a substrate.

Other exemplary structures for MNAi are demonstrated in FIG. 9.

The MNAi and the catalytically active MNAzyme represent two alternate states for the assembled components, namely an "off" state and the "on" state respectively.

4. Use of the Compositions as Logic Gates

One skilled in the art would recognise that the MNA complexes as described herein may be used as a logic gate. "On" states include assembled, catalytically active MNA complexes, including but not limited to, MNAzymes or apta-MNAzymes in the presence of their activator ligand. "Off" states include catalytically inactive MNA complexes including but not limited to fully or partially disassembled MNA complexes, apta-MNA complexes where the activator ligand is not present, and MNAis. Accordingly in one aspect of the invention, an MNA complex logic gate is provided comprising at least one inactive MNA complex, at least one input and at least one output, wherein the presence of said input activates said inactive MNA complex logic gate and wherein said activation provides said output. The gate is capable of at least two different output states, wherein said states depend on the activation of said inactive MNA complex logic gate.

In a further aspect of the present invention the MNA complex gate has at least two inputs, and a first output state wherein the MNA complex is inactive and a second output state wherein said MNA complex is activated. The first output state, wherein the MNA complex is not activated corresponds to a logical off and the second output state, wherein said MNA complex is activated, corresponds to a logical on. Alternatively, the first output state may correspond to a logical on and the second output state may correspond to a logical off.

In a further preferred aspect of the invention, the output of the MNA complex logic gate may be detected by any one or any combination of fluorescence spectroscopy, surface plasmon resonance, mass spectroscopy, NMR, electron spin resonance, polarization fluorescence spectroscopy, circular dichroism, immunoassay, chromatography, radiometric methods, electronic methods, UV, visible light or infra red spectroscopy, enzymatic methods.

In a still further embodiment of the invention, the MNA complex logic gate may comprise two inputs and be a logical AND gate wherein the MNA complex is activated, thereby providing an output corresponding to logical on, only if the first and second inputs are present. In the presence of either input alone or in the absence of input the MNA complex remains inactive, corresponding to a logical off.

In a still further embodiment of the invention the MNA complex logic gate may comprise one input and be a logical sensor gate, wherein said input activates the inactive MNA complex logic gate thereby providing an output corresponding to logical on and in the absence of said input the inactive MNA complex logic gate remains inactive corresponding to logical off.

In an additional embodiment of the invention the MNA complex logic gate may comprise two inputs and be a logical OR gate wherein either or both of said inputs activates the MNA complex logic gate, thereby providing an output corresponding to logical on and wherein if no input is present the MNA complex logic gate remains inactive, corresponding to a logical off.

In a further embodiment of the invention the MNA complex logic gate may comprise two inputs and be a logical EX-OR (Exclusive-OR) gate wherein either but not both of said inputs activates the MNA complex logic gate, thereby providing an output corresponding to logical on and wherein if no input is present or if both inputs are present the MNA complex logic gate remains inactive, corresponding to a logical off.

Further one skilled in the art will realise that disassembly and assembly of MNAzymes can equally provide two states, an on state and off state and transition between the two states can be modulated by many entities and events. These states can also be applied to logic gate systems in a similar manner as that described above.

An example of the use of logic gates in a full adder is exemplified in FIG. 12 and described in Example 12.

5. Methods Using Insoluble and Solid Supports

It is also to be understood that generally the methods, whether multiplexed or not, are applicable in solution, or combined with an insoluble support or solid support on which one or more of substrate, MNA complex components or portion thereof, may be attached. Accordingly, at least one of partzyme components, a substrate, an assembly facilitator, assembly inhibitor and/or an activity inhibitor may be bound, attached or tethered. Again the features of such assay systems will be generally understood by the skilled artisan provided with the methods and variations exemplified herein and the working examples. Thus, the invention is not to be considered limited to the literal teachings herein, but is capable of being modified and varied consistent with the principles and scope of the teachings provided herein and the knowledge in the art.

Embodiments of the present invention encompassing an insoluble support in the form of a "chip", otherwise known as an array or microarray, typically comprise a plurality of substrates coupled, tethered or otherwise attached to the chip. In particular embodiments, the substrates comprise a nucleic acid. A plurality of nucleic acids may be positioned upon the chip by any suitable method known in the art, for example, by pipette, ink-jet printing, contact printing or photolithography. The chip may be comprised of at least one element, with each element comprising at least one nucleic acid. The at least one element may be comprised of a plurality of nucleic acids of the same sequence. The number of elements comprising a chip may be any number, and where a plurality of elements is positioned on a chip, the elements may be spaced apart at a uniform or a variable distance, or a combination thereof. In some embodiments, the elements may be positioned randomly, with the respective location of each element then determined. The size and shape of the elements will depend upon the particular application of the present invention, and different sized and shaped elements may be combined into a single chip. The surface of the chip may be substantially planar or may have features such as depressions or protuberances, and the elements may be positioned either into the depressions or onto the protuberances. Such depressions may provide a reservoir for solutions into which the elements are immersed, or such protuberances may facilitate drying of the elements. For example, elements may be placed in each well of a 96 well plate. In some embodiments, the chip may include unique identifiers such as indicia, radio frequency tags, integrated devices such as microprocessors, barcodes or other markings in order to identify each of the elements. The unique identifiers may additionally or alternatively comprise the depressions or protuberances on the surface of the array. Furthermore, the unique identifiers can provide for correct orientation or identification of the chip. The unique identifiers may be read directly by a data capture device or by an optical scanner or detector.

6. Reporter Substrate Systems Used in the Methods

Also provided in accordance with the present invention are generic reporter substrate systems, which allow rapid system development by allowing facile design changes to create new MNAzymes and inactive MNA complexes which recognize different assembly facilitators. As discussed herein, the substrate arm portion and the catalytic core portion of the partzymes may remain unchanged, with changes only to the sensor arm portion of one or more partzymes required for new assembly facilitators. A generic substrate sequence is provided and the same substrate can therefore be incorporated in systems for various diverse applications. Further, the same substrate can be incorporated into the methods in various embodiments herein, including assays where the substrate is free in solution or is tethered or attached to a support. A series of generic substrates can be used in a multiplex reaction allowing simultaneous detection of multiple assembly facilitators.

Substrates which have been cleaved can be reconstituted and hence recycled using a DNAzyme ligase.

7. Substrates Used in the Methods

As described in more detail below, MNA complexes such as MNAzymes and inactive MNA complexes have an advantageous property in certain embodiments of being able to utilize a universal or generic substrate. Such a substrate is shown in FIG. 1 in a presently preferred configuration wherein the substrate comprises both a detectable portion and a quencher portion. The quencher portion is adapted to diminish or eliminate a detectable signal from the detectable portion of the substrate until the substrate is cleaved by an MNAzyme. For example, the quencher portion may comprise "Black Hole Quencher 1" (BHQ1) or "Black Hole Quencher 2" (BHQ2).

Thus, the MNAzyme cleaves the substrate between the detectable portion and the quencher portion allowing the two portions to separate in solution, thereby allowing the detectable signal to appear or increase as the quencher portion is distanced from, or effectively removed from the local environment of the detectable portion.

The use of the generic or universal substrate is enabled through the design of the MNAzyme's component partzymes. By altering only the sensor arms of the partzymes, but by leaving the substrate arms unchanged, a large variety of MNAzymes and inactive MNA complexes specific for each of a plurality of assembly facilitators can be designed all of which utilize a universal substrate to produce an output signal. The skilled artisan will appreciate the advantages that this offers in terms of eliminating the need for customized or unique substrates to respond to each input event. Detection of each new assembly facilitator requires only one or more changes in one or more of the sensor arm portions; the substrate arm portion and the catalytic core portion can remain constant. Thus, a single reporter substrate can be used for a single assembly facilitator or other input event using an MNA complex, such as an MNAzyme, and multiple assembly facilitators in a series of systems using altered MNA complexes such as MNAzymes. A plurality of reporter substrates allows multiplexed monitoring of multiple MNA complexes and MNAzymes within one system.

Further, the substrates may incorporate additional entities such as labelled nucleic acids, nanoparticles, microparticles, proteins, antibodies, RNA, DNA, nucleic acid analogues, biotin group, glycoproteins, lipoproteins, peptide nucleic acids, locked nucleic acids, peptide-nucleic acid chimeras, moiety for radio-frequency magnetic field, or any combination thereof.

Substrates can be modified by an MNAzyme thereby providing a "detectable effect" or "output" signal. In the detection process, the substrate modification by an MNAzyme may involve, for example, cleavage, ligation, porphyrin metallation, and formation of carbon-carbon bonds, ester bonds or amide bonds. As a consequence of substrate modification by an MNAzyme, a detectable effect is generated and the magnitude of the effect may therefore be indicative of the quantity of the input signal. The detectable effect may be detected by a variety of methods, including fluorescence spectroscopy, surface plasmon resonance, mass spectroscopy, NMR, electron spin resonance, polarization fluorescence spectroscopy, circular dichroism, immunoassay, chromatography, radiometry, photometry, scintigraphy, electronic methods, UV, visible light or infra red spectroscopy, enzymatic methods or any combination UV, visible light or infra red spectroscopy, enzymatic methods or any combination thereof.

Several groups have reported detection of nucleic acid targets, and other analytes with colourimetric readouts (Elghanian et al., 1997, Mirkin et al, 1996, and Liu and Lu, 2004). The strategy involves preparation of batches of gold nanoparticles, each of which has a distinct DNA oligonucleotide sequence attached to its surface. Gold particles can then be aggregated by the addition of a "bridging oligonucleotide", which has complementarity with the sequences that are attached to the gold particles. Particle aggregation results in a concomitant change in colour from red to blue (Mirkin et al, 1996). Inclusion of a DNAzyme substrate sequence within the bridging oligonucleotide can provide a mechanism for reversing the aggregation of the gold particles (Liu and Lu, 2004). Activation of the lead-dependent DNAzyme by the addition of lead, caused cleavage of the bridging oligonucleotide, dissociation of the gold particles and a change in colour from blue to red.

Simple detectors for monitoring changes could be developed using this principle and an MNA complex, such as an MNAzyme. Changes in temperature or other entities or events could activate MNA complex(es) to form MNA zyme(s) which could cleave bridging oligonucleotides causing the dissociation of nanoparticles and a change in colour.

8. Optimization of the Methods

The skilled artisan will readily understand that the methods described herein may be optimized using a variety of experimental parameters. The particular experimental parameters that are optimized, and the level of such optimization, will depend upon the particular method being employed and/or the particular event to be detected. Such parameters include, but are not limited to, time, temperature, concentration of salts, detergents, cations and other reagents including but not limited to dimethylsulfoxide (DMSO), and length, complementarity, GC content and melting point (Tm) of nucleic acids. The temperature at which such methods may be performed may be in the range of about 20° C. to about 96° C., about 20° C. to about 75° C., 20° C. to about 60° C. or about 20 to about 55° C. The temperature may be constant or may be cycled between one temperature which is compatible with assembly and catalytic activity of an MNAzyme and one temperature which is incompatible with catalytic activity.

Additionally or alternatively, a variation in a parameter, and/or the microenvironment, may be used to switch the MNA complex from an inactive to an active state. Thus, a parameter in the microenvironment may comprise an "activator" as herein defined, including but not limited to events such as change in temperature, wavelength, concentration of salts, detergents, cations, and concentration of structural and modulator components which include but are not limited to assembly facilitators or assembly facilitator components, partzymes or partzyme components, substrates, assembly inhibitors, activity inhibitors and activator oligonucleotide components. Accordingly, such optimization of parameters and/or microenvironment may be undertaken in order to achieve use of the MNA complexes as molecular switches.

In one preferred embodiment, optimized reactions for practicing the methods of using MNA complexes are provided herein. In such optimized reactions, activation of catalytic activity may be increased by up to 10, 20, or 30% above unoptimized reactions. More preferred reaction conditions may improve catalytic activity by at least 35%, or 40%, and preferably up to 50% or more. In still more preferred embodiments, optimized reactions may have an increase in activation of catalytic activity of more than 50%, and up to 66%, 75% or even 100%. In yet more preferred embodiments, a fully optimized reaction method may offer 100, 200 or even 300% or more increase in activation of catalytic activity. Other preferred reaction conditions may improve the activation of catalytic activity by up to 1000% or more over methods practiced with unoptimized reaction conditions. A highly preferred reaction condition for optimizing the methods provided herein is the inclusion of certain divalent cations. The catalytic activity of most nucleic acid enzymes may be influenced in a concentration-dependent fashion by the concentration of divalent cations. Preferred optimized reactions may be optimized for one or more of $Ba^{2+}$, $Sr^{2+}$, $Mg^{2+}$, $Ca^{2+}$, $Ni^{2+}$, $Co^{2+}$, $Mn^{2+}$, $Zn^{2+}$, and $Pb^{2+}$.

9. Methods Using Aptamers

With reference to FIG. 7, a method is illustrated whereby an activator ligand can be used to switch "on" or "off" the activity of the apta-MNAzyme. The method using an assembly inhibitor to block activity of apta-MNAzymes in the absence of an activator is illustrated. These methods use aptamers which may comprise a nucleic acid or protein, polypeptide, or peptide or combination thereof that has the ability to recognize one or more ligands. Aptamers may bind, for example, proteins, polypeptides, peptides or nucleic acids, glycoproteins, lipids, lipoproteins, cells, viruses, bacteria, archaea, fungi, antibodies, metabolites, pathogens, toxins, contaminants, poisons, entire organisms, small molecules, polymers, metal ions, metal salts, prions or any derivatives, portions or combinations thereof, or any other entity (Lee et al., 2004).

Preferred aptamers herein may comprise short single-stranded DNA or RNA oligomers that can be isolated from complex libraries of synthetic nucleic acids by an iterative process of adsorption, recovery, and reamplification. Aptamers may therefore be generated against almost any target, ranging from small molecules such as amino acids or antibiotics, to protein and nucleic acid structures. In preferred embodiments, aptamers include, for example, nucleic acid binding molecules which are preferably generated by evolution and selection techniques. Preferably, aptamers may comprise DNA or RNA molecules, or a combination of both, including but not limited to the nucleotide analogues as per, for example, Table 1 above.

One skilled in the art will appreciate that the aptamer may be incorporated into either end of the assembly facilitator molecule or molecules, and or the activity inhibitor. Further it will be appreciated that an aptamer or multiple aptamers could be incorporated into one or more of the partzyme oligonucleotide components. Still further it will be appreciated that an aptamer or multiple aptamers could also be incorporated into at least one of the partzyme oligonucleotide components. The assembly facilitator in the strategies illustrated in FIG. 7 may comprise, for example, DNA, RNA, LNA, PNA or a sequence containing one or more nucleotide base analogues.

In the strategy shown in FIG. 7, an aptamer sequence is incorporated at the end of a partzyme (apta-partzyme) in a configuration whereby an active MNAzyme is only formed in the presence of the activator.

It will also be appreciated by one skilled in the art that one or more aptamers could be incorporated into any of the oligonucleotide components, including the partzymes, the assembly facilitator or the substrate. Further the aptamer could be incorporated into either end of any one of these oligonucleotides.

The strategy illustrated in FIG. 7 can be used either (i) to provide a method to control MNA complex activity using ligands as activator molecules, and/or (ii) to provide a method for detection of non-nucleic acid, and nucleic acid targets using apta-MNA complexes which form MNAzymes when contacted with a ligand activator. The nucleic acid oligonucleotides required for this apta-MNAzyme detection strategy include;

a) standard partzyme;
b) an apta-partzyme which is a partzyme with an aptamer incorporated into one of its ends;
c) an assembly facilitator which is an oligonucleotide which binds to both the apta-partzyme and the partzyme enabling assembly of an active MNAzyme;
d) a reporter substrate; and
e) an assembly inhibitor oligonucleotide which hybridises to the apta-partzyme in a region which spans at least part of the aptamer sequence and part of the substrate binding arm of the apta-partzyme sequence.

In the absence of an activator ligand (left hand panel), the assembly inhibitor oligonucleotide binds to the apta-partzyme thus competing with and blocking binding of the reporter substrate. This structure represents an inactive MNA complex. When an activator ligand is present (right hand panel), it binds to the aptamer sequence of the apta-partzyme, blocking the binding of the assembly inhibitor oligonucleotide, and thus allowing binding of the substrate and formation of a catalytically active MNAzyme which then, in this scenario, cleaves the substrate. As such, catalytically active MNAzymes can form and cause fluorescent signal generation only in the presence of activators that can bind aptamers.

In some embodiments, modulation of MNAzyme activity can be achieved using either a nucleic acid or a non-nucleic acid target activator ligand as a switch mechanism. In other embodiments, the assembly inhibitor molecule is manipulated by other means so as to modulate activity. For example, the assembly inhibitor could be removed by several strategies including selective thermal denaturation or method that use oligonucleotides to compete for binding and/or that use branch chain migration to displace fragments.

10. Methods Using Cascades

Persons skilled in the art will appreciate that the methods described herein may be used to perform a cascade as herein defined. Particular embodiments of performing such methods as disclosed herein include, but are not limited to (1) activation of an inactive MNA complex to form an MNAzyme to modify a substrate only in the presence of a target or event, wherein said substrate is then made available for involvement in a second event such as generation of a detectable signal, or (2) activation of an inactive MNA complex to form an MNAzyme to modify a substrate only in the presence of a target or event, wherein said substrate is then made available for involvement in a second event, wherein performance of said second event in turn makes available a further substrate for involvement in any number of subsequent events, such that a subsequent event makes available a substrate for involvement in the performance of an earlier event, thereby creating a cyclic cascade, such as depicted in FIG. 6, FIG. 10 and FIG. 11 (iii), wherein such cyclic cascades may be employed to amplify a signal, for example, in applications where an input event is of low intensity, for example when a target is in low abundance and may not otherwise provide for a output signal that is detectable.

One mechanism for generating an MNAzyme replication cascade designed for target analyte detection uses the SCUD cascade strategy. The SCUD strategy can be incorporated into cascades in a variety of designs as illustrated, by way of example, in FIG. 6, where two MNA complexes are incorporated; in FIG. 10, where three MNA complexes are incorporated; and in FIG. 11 where both MNA complexes and a DNAzyme ligase are incorporated in a cascade reaction.

The SCUD method relies on the ability to control the assembly of active MNAzymes and MNAi from component oligonucleotides present in the mix. One format of SCUD is depicted in FIG. 6. This SCUD example describes a general method for signal amplification.

One embodiment of the method, known as SCUD (Signal Cascade using DNA), as illustrated in FIG. 6, contains the following components:
(i) an activity inhibitor (such as the dual labelled RIF (Reporter-Inhibitor-Facilitator) as depicted in FIG. 6) containing three regions;
  a. an activity inhibitor/reporter (RI) domain which has the dual functions of firstly being an activity inhibitor when incorporated into RIF and secondly providing a fluorescent signal when RIF is cleaved, and
  b. an activator assembly facilitator component F2b which forms an essential component of MNAzyme 2a,
  c. a substrate domain located between the RI and F2b domains, which may be cleaved by either MNAzyme 1a or MNAzyme 2a,
(ii) an assembly facilitator component F2a
(iii) partzymes capable of forming active MNAzyme 1a structures only in the presence of assembly facilitator F1, which by way of example may be a target nucleic acid present in a test sample; the active MNAzyme 1a being capable of cleaving RIF into RI and F2b components, thus generating fluorescence, negating the MNAzyme activity inhibitory effect and concomitantly generating a new activator assembly facilitator component F2b.
(iv) partzymes capable of forming active MNAzyme 2a complexes only when the partzyme arms bind assembly facilitator component F2a adjacent to the liberated activator assembly facilitator component F2b. The MNAzyme 2a in turn could cleave more RIF liberating more RI and F2b thus creating a cascade of MNAzyme 2a self-replication and concomitant fluorescent signal amplification.

In the absence of F1, which by way of example could be a target nucleic acid, the partzymes for MNAzyme 2a would form an inactive complex, MNAi 21, with intact RIF. Intact RIF functions as an activity inhibitor in the formation of MNAi 21. In the presence of target analyte, active MNAzyme 1a would form, thus cleaving RIF and liberating an activator assembly facilitator component F2b which would then be free to associate and become a component of an active MNAzyme 2a. Since MNAzyme 2a can further cleave more RIF, this would initiate the replication/signal amplification cascade.

Each time an MNAzyme 2a cleaves a RIF molecule, more components (activator F2b assembly facilitators) required for formation of new MNAzymes 2a would be generated. The MNAzyme cascade results in the assembly of MNAzyme 2a complexes that are identical to the parent MNAzyme using components which are the products generated by MNAzyme 2a catalytic activity. As such, the product of the MNAzyme cleavage (F2b) is able to direct the assembly of new (parent) MNAzyme molecules in a self-replicating system which is autocatalytic.

The structures described herein and other molecular switches can form components of cascades including self replicating cascades.

With reference to FIG. 10, such a cascade may comprise an MNA complex which functions in the detection of a target, for example by interacting with the target. In this way, the target acts as an assembly facilitator and initiates the cascade by facilitating the formation of an initiating MNAzyme. This initiating MNAzyme (Mt in FIG. 10) may modify a substrate. The modification may be, for example, cleavage. In this case the modification results in the generation of a first assembly facilitator for the formation of a cascading first MNAzyme (Mc1 in FIG. 10). The cascading first MNAzyme may then modify a additional substrate to generate an additional assembly facilitator to direct the formation of an additional MNAzyme (Mc2 in FIG. 10). The additional MNAzyme may then modify the first substrate to generate further first assembly facilitators for the cascading first MNAzyme, and thus feedback into an earlier stage of the cascade is generated. In some embodiments the assembly facilitators may be activator assembly facilitators.

One skilled in the art would recognise that in this cascade the first substrate, in its uncleaved state may act as an activity inhibitor of the cascading first MNAzyme. That is the cascading first MNAzyme is, in fact, an MNAi until such time as the first substrate is cleaved by the initiating MNAzyme to generate an first activator assembly facilitator which then functions to switch the cascading first MNAi from the "off" state to the catalytically active "on" state of the cascading first MNAzyme.

Similarly one skilled in the art would recognise that the additional substrate in its uncleaved state may act as an activity inhibitor of the additional MNAzyme. That is the additional MNAzyme is, in fact, an MNAi until such time as the additional substrate is cleaved by the cascading first MNAzyme to generate an additional activator assembly facilitator which then functions to switch on the additional MNAzyme.

One of skill in the art would recognise that FIG. 10 shows three assembly facilitator components are required to facilitate active MNAzyme assembly. More or less assembly facilitator components could be utilised in a similar schema.

With reference to FIG. 11 the structures described herein and other molecular switches can form a signal amplification cascade in which a target molecule facilitates the formation of a first MNAzyme resulting in the cleavage of a first substrate to generate two cleavage products (designated Aa and Ab). Aa functions as a component in a ligation step (indicated by box ii in FIG. 11) and Ab functions as a component in a SCUD amplification (indicated by box iii in FIG. 11). Aa typically has a 2',3'-cyclic phosphate at its 3' terminus in order to allow it to function as a substrate for a DNAzyme ligase.

In the ligation step the DNAzyme ligase ligates Aa to a second substrate to create a partzyme for an additional MNAzyme (the additional MNAzyme is indicated in box iv in FIG. 11).

In the SCUD amplification step (indicated by box iii in the Figure), Ab functions as an assembly facilitator of a second MNAzyme which modifies the first substrate to generate further Aa and Ab. The further Aa and Ab are utilised in the ligation and SCUD amplification steps respectively thereby forming a feedback amplification cascade resulting in accumulation of Aa and Ab.

The ligation product of the ligation step is a partzyme for an additional MNAzyme which modifies an additional substrate resulting in a detectable effect indicative of the presence of the target.

In a preferred embodiment of the invention, the modification of one or more of the substrates may be detected by any one or any combination of fluorescence spectroscopy, surface plasmon resonance, mass spectroscopy, NMR, electron spin resonance, polarization fluorescence spectroscopy, circular dichroism, immunoassay, chromatography, radiometric methods, electronic methods, UV, visible light or infra red spectroscopy, enzymatic methods.

One skilled in the art would recognise that in this cascade the first substrate, in its uncleaved state may act as an activity inhibitor of the second MNAzyme. That is the second MNAzyme is, in fact, an MNAi until such time as the first substrate is cleaved by the first MNAzyme to generate an assembly facilitator which then functions to switch on the second MNAi.

MNAzyme mediated amplification cascades could be initiated by either nucleic acid targets (DNA/RNA), or other target ligands (proteins, small molecules etc) if the strategy was linked with an apta-MNAzyme system. Since the reaction is only initiated in the presence of ligands or other input events, it provides a technique for detection and/or identification of target analytes. MNAzyme mediated amplification cascades are based on the activation of multicomponent nucleic acid complexes. Unlike target amplification techniques such as the polymerase chain reaction, or the ligase chain reaction, MNAzyme mediated replication and signal amplification requires no protein enzymes to facilitate the process. This provides a major advantage over these commonly used protocols. Further, the ability to control and regulate the catalytic activity of MNAzymes using several oligonucleotide components, such as stabiliser arm components or assembly facilitator components allows the assembly of MNAzymes to be tightly regulated by conditions and components in the microenvironment.

MNAzyme mediated amplification cascades could be applied to a range of biotechnological applications, especially in diagnostics. They could allow detection of proteins and nucleic acids for disease diagnosis by facilitating signal amplification. Catalytic nucleic acids and/or cascade reactions can be used for applications other than diagnostics, for example, within the field of computation analysis and biomolecular engineering of nano-scale devices and switches which may be used in therapeutics.

11. Methods which Allow Switching Between Active and Inactive States of MNA Complexes by Removal of Components Such as the Activity Inhibitor or the Assembly Facilitator.

A transition between active MNAzymes and inactive MNA complexes, or visa versa, can be achieved by the provision or removal of MNA complex components including but not limited to one or more activity inhibitors, assembly facilitators, assembly inhibitors, partzymes, or stabiliser arms or parts thereof. In some embodiments, the activity inhibitor may include a labile or cleavable linker or substrate, which may be located between two or more domains within the activity inhibitor, for example an activity inhibitor domain and an activator assembly facilitator domain. Cleavage at the linker site may allow separation of an activity inhibitor domain from an activator assembly inhibitor domain, which may then function as an assembly facilitator component and direct the assembly of an active MNAzyme. Cleavage of the linker could be achieved by several methods, including but not limited, MNAzyme cleavage, protein enzyme cleavage, or hydrolysis induced by changes in the pH and or temperature.

Alternatively the assembly inhibitor and/or assembly facilitator could be selectively removed using a process involving branch migration and/or complementarity to component oligonucleotides. Modulator oligonucleotides which function through complementarity may do so by altering the secondary structure of oligonucleotides to which they bind. In some embodiments this may result in an alternate conformation where an activator sequence is now able to assemble with other components to form active MNAzymes. By way of example, such a modulator oligonucleotide may cause the disruption of intramolecular structures such as hairpins which constrain activator molecules in non-functional conformations.

In some embodiments an MNA component such as an inhibitor, including but not limited to an activity inhibitor or assembly inhibitor, may be conjugated to other entities. In some embodiments the component is conjugated to a gold nanoparticle coupled to a radio-frequency magnetic field. This allows remote electronic control of hybridisation, with the radio-frequency magnetic field functioning as an antenna enabling reversible thermal denaturation of specific oligonucleotides, while leaving the surrounding molecules relatively unaffected. In some embodiments the component can be labelled with biotin to facilitate capture and physical isolation of the component.

12. Kits

The present invention also provides kits for practising the methods disclosed herein. Typically, kits for carrying out the methods of the present invention contain all the necessary reagents to carry out the method. For example, in one embodiment a kit may comprise a first container containing an inactive MNA complex, such as an MNAi, wherein activation of said inactive MNA complex to form an MNAzyme requires abrogation of inhibition of catalytic activity through exposure of the inactive MNA complex to an activator, wherein said activator abrogates the inhibitory influence of an inhibitor. For example, in one embodiment a kit may comprise one or more components for the formation of the inactive MNA complex in separate containers.

In one embodiment a kit may comprise a first container containing components for an inactive MNA complex, wherein activation of said MNA complex to form an MNAzyme requires activation of catalytic activity through exposure of the MNA complex to an activator by methods disclosed herein.

Typically, the kits of the present invention will also comprise one or more other containers, containing for example, wash reagents, and/or other reagents as required in the performance of the methods of the invention.

In the context of the present invention, a compartmentalised kit includes any kit in which reagents are contained in separate containers, and may include small glass containers, plastic containers or strips of plastic or paper. Such containers may allow the efficient transfer of reagents from one compartment to another compartment whilst avoiding cross-contamination of the samples and reagents, and the addition of agents or solutions of each container from one compartment to another in a quantitative fashion. Such kits may also include a container which will accept the test sample, a container which contains the reagents used in the assay, containers which contain wash reagents, and containers which contain a detection reagent. Typically, a kit of the present invention will also include instructions for using the kit components to conduct the appropriate methods. Kits and methods of the invention may be used in conjunction with automated analysis equipment and systems, for example, including but not limited to, real time PCR machines.

For application to detection, identification or quantitation of different targets or events, a single kit of the invention may be applicable, or alternatively different kits, for example containing reagents specific for each target, may be required. Methods and kits of the present invention find application in any circumstance in which it is desirable to detect, identify or quantitate any entity or event.

The present invention will now be further described in greater detail by reference to the following specific examples, which should not be construed as in any way limiting the scope of the invention.

EXAMPLES

Example 1

Example of an MNAzyme where Partzyme B Comprises Two Molecules

Many variations on the basic design of an MNAzyme are contemplated in the present invention. In this example, MNAzymes were assembled in the presence of an assembly facilitator from partzyme A, and partzyme B which contained two components, namely one partzyme component with a truncated sensor arm, and one component that functions as a stabiliser arm. MNAzyme assembly occurs via Watson-Crick base recognition of the partzyme sensor arms and the assembly facilitator sequence. In the following example, the use of a truncated partzyme arm and a stabiliser arm was demonstrated.

The MNAzyme detection strategy used in this example is illustrated in FIG. 2 (panel (ii)) and in FIG. 3.

The oligonucleotides required are described below:
a) a standard partzyme A;
b) a partzyme B comprising a first component which contains a substrate arm, a partial catalytic core and truncated sensor arm; and a second stabiliser arm component, which hybridizes to the assembly facilitator, adjacent to the truncated sensor arm of the partzyme. This stabiliser arm is designed to facilitate MNAzyme assembly when the truncated sensor arm of the partzyme is hybridized to the assembly facilitator; and
c) a substrate, for example a reporter probe substrate.

Active MNAzyme assembly also requires the presence of an assembly facilitator.

1.1. Partzyme Oligonucleotides and Stabiliser Arm

In this example, the truncated sensor arm of partzyme B was only 5 nucleotides in length. The sequences of partzyme A and the two partzyme B components are shown below (5' to 3'). In the following sequences the bases in bold hybridize with the assembly facilitator, bases underlined form part of the catalytic core of the assembled MNAzyme, and bases in italics hybridize to the substrate. The "-P" indicates 3' phosphorylation of the oligonucleotide.

SEQ ID NO: 1 Partzyme A4 Xd-P:
ACTGGATGTCCATCTGTCTGACAACGAGAGGAAACCTT-P

SEQ ID NO: 2 Partzyme B5 Xd-P component 1:
TGCCCAGGGAGGCTAGCTTATAC-P

SEQ ID NO: 3 Partzyme B stabiliser arm component XdS-P:
CTTCGTGAGGGTGAG-P

1.2. Reporter Substrate

The reporter substrate used in this example was SubBi-2 end-labelled with a 6-FAM moiety at the 5' end, a BHQ1 moiety at the 3' end and designated SubBi-2-FB. Cleavage of SubBi-2-FB was monitored at 520 nm (FAM emission wavelength) with excitation at 490 nm (FAM excitation wavelength). The sequence of SubBi-2-FB is listed below (5' to 3'); the lower case bases represent RNA and the upper case bases represent DNA.

SEQ ID NO: 4 SubBi-2-FB:
AAGGTTTCCTCguCCCTGGGCA

1.3. Assembly Facilitator Molecule

The sequence of the synthetic oligonucleotide used as the assembly facilitator is below (5' to 3'). This assembly facilitator was fully matched with the partzyme B sensor arm. Nuclease-free water was used in place of target assembly facilitator as a "no target" control.

SEQ ID NO: 5 Assembly facilitator Xd-T:
TGCCCCCTCACCCTCACGAAGGTATACAGACAGATGGACATCCAGTTGGT
GA

1.4 Reaction Conditions

Detection of the assembly facilitator was measured by an increase in fluorescent signal caused by cleavage of the reporter substrate by the catalytically active MNAzyme. Reactions were initiated by the addition of substrate and the total volume of all reactions was 50 µL. Reactions were conducted at 55° C. on a FLUOstar OPTIMA (BMG Biotech). Fluorescence for each reaction was read every 2 seconds for a total of 5 minutes. All reactions contained 200 nM A4Xd-P, 200 nM B5Xd-P, 1×PCR Buffer II (Applied Biosystem) and 25 mM MgCl₂. In addition, reactions contained oligonucleotides as listed in Table 3.

TABLE 3

Additional reagents in MNAzyme reactions.

| Reaction | Assembly Facilitator | Stabiliser arm |
|---|---|---|
| (i) | 200 nM of Xd-T | 200 nM of XdS-P |
| (ii) | 200 nm of Xd-T | No stabilizer arm |
| (iii) | No assembly facilitator (water control) | 200 nM of XdS-P |

1.5 Results: Assembly of Active MNAzymes in the Presence of the Partzymes, and an Assembly Facilitator When both the assembly facilitator, and a partzyme stabiliser arm component were included in the reaction (Reaction (i): FIG. 3), active MNAzymes assembled and cleaved the substrate, resulting in an increase in fluorescence over time. In contrast, there was no increase in fluorescence in the absence of the assembly facilitator (Reaction (iii): FIG. 3). Further, the presence of the stabiliser arm was shown to be essential for formation of active MNAzymes. A reaction containing all reaction components including the assembly facilitator, but which lacked the stabiliser arm component, gave no increase in fluorescence over time (Reaction (ii): FIG. 3). As such, the 5 bases of the sensor arm of partzyme B were insufficient to form a stable MNAzyme complex but the presence of a stabiliser arm component was shown to be capable of compensating for the short length (truncation) of the partzyme sensor arm and allowing stable MNAzyme formation under stringent temperature conditions (55° C. in this example). The stabiliser arm component is thus an essential oligonucleotide for assembly of active MNAzymes in this system, which uses a partzyme with a truncated sensor arm.

Further, when an alternative assembly facilitator, which had a single nucleotide mismatch with the partzyme sensor arm was included in a reaction containing partzyme A and the two components of partzyme B, the fluorescent signal did not increase over time (data not shown).

This example demonstrates that MNAzymes could only form in the presence of a fully matched assembly facilitator under the conditions of the experiment. One skilled in the art will appreciate that transition between an active MNAzyme and an inactive MNA complex can be regulated by providing fully matched or mismatched assembly facilitators. Further, the example demonstrates the use of two-component partzymes, which comprise a first molecule that contains a truncated sensor arm, and a second stabiliser arm molecule. The requirement for the presence of a stabiliser arm molecule in such systems, provides another tool with which one can regulate the assembly of MNAzymes.

Great flexibility is afforded by MNA systems which contain multiple oligonucleotide components, the sequence of which can be tailored with respect to the melting temperature, the sequence composition and complementarity or lack thereof with other component oligonucleotides. Shorter sequences, including but not limited to, partzyme components with truncated arms, stabilizer arms, and assembly facilitator components are particularly useful in this aspect of the invention.

Example 2

Regulation of the Assembly and Disassembly of MNA Complexes Using Temperature and its Application to the Construction of a DNA Nano-Scale Device for Temperature Sensing MNAzyme assembly and disassembly can also be controlled by temperature. A rise or fall in temperature can provide a mechanism with which to switch the catalytic activity of the MNAzyme "on" and "off". The sensitivity of an MNAzyme to temperature could be exploited to build thermo-sensors and rheostats.

If the temperature were either too high, or too low, for the assembly (hybridization) of the component oligonucleotides, and/or for catalytic activity, of an MNAzyme then an active complex capable of modifying (eg cleaving) a substrate would not be formed. If the temperature were permissive for MNAzyme assembly and/or activity then a substrate would be modified and a signal would be generated.

The ability to change the melting temperature of the component oligonucleotides (for example, the partzymes, including stabiliser arm components and/or assembly facilitators,) by altering base composition and/or oligonucleotide length, allows systems to be built that allow finer tuning of MNAzyme systems. This allows MNAzymes to not only be in a fully "on" or fully "off" state but rather it allows for a gradation of activity suitable for use in rheostat systems. It also allows modulation of the temperature range over which the MNAzyme response occurs.

A rise or fall in temperature from one that is incompatible with MNAzyme activity, to another that is compatible with MNAzyme activity, would be detected by a signal generated following substrate modification by the MNAzyme. The readout could, for example, be fluorescent or colourimetric.

The MNAzyme complexes could respond to temperature changes by cleaving bridging oligonucleotides, responsible for causing the aggregation of gold nanoparticles. This would allow development of a simple colourimetric device capable of detecting temperature changes. One skilled in the art would appreciate that the invention of simple devices using MNAzymes for temperature sensing could be applied in many industries including, for example the pharmaceutical, food and agricultural industries.

One application could involve co-packaging an MNAzyme temperature-sensor with temperature sensitive drugs or other compounds. If the package were not stored under appropriate temperature conditions (e.g. under refrigeration) then MNAzymes could form and generate a signal, thus identifying the compounds as spoilt. Similarly, food that needs to remain within set temperature limits, for example, frozen food, could be monitored by an MNAzyme temperature-sensor, capable of identifying food that had been thawed at some stage during storage.

This example of using temperature to control the catalytic activity of MNAzymes demonstrates a general strategy of switching the catalytic activity of MNAzymes on and off. As such, MNAzyme assembly and disassembly could be controlled by many of the factors which can impact on the catalytic rate. Such examples include, but are not limited to, the presence or absence of component partzymes or assembly facilitators, salt concentration, pH, divalent cation type and concentration, the presence or absence of additives, and temperature.

Example 3

Mechanisms for Facilitating and Inhibiting the Assembly of Active MNAzymes or MNAi An MNAzyme is composed of partzymes, which assemble in the presence of one or more assembly facilitator components, to form an active enzyme (e.g. FIGS. 1, 2, 4 (right hand panel), FIG. 5 (i) and (ii) and FIG. 9 (left hand structures). The assembly facilitator(s), which binds to partzyme sensor arms, can be a target analyte, or can be a synthetic nucleic acid molecule(s) added to the reaction mix to drive MNAzyme assembly. In addition to their capacity to contribute to active MNAzyme assembly, partzymes can assemble into an inactive, non-catalytic, MNAi complex when they hybridise with an "activity inhibitor" molecule (FIG. 4 (left hand panel), FIG. 5 and FIG. 9 (structures to the right of MNAzyme structures)). Various alternative oligonucleotide sequences were tested for their capacity to regulate the assembly of either active MNAzyme complexes or MNAi.

In this example (depicted in FIGS. 4 and 5), MNAzyme assembly was examined in the presence of (i) a single molecule (assembly facilitator F1/2), or (ii) two molecules (assembly facilitator component F1 and assembly facilitator component F2), whose sequences together comprise that present in facilitator F1/2. Facilitator F2 binds to the whole sensor arm of one partzyme and overlaps to bind 4 base pairs of the sensor arm of the second partzyme. In another reaction, an "activity inhibitor" molecule, which has a sequence that includes that of facilitator F2 plus an additional activity inhibitor domain, was tested for its ability to drive the reaction towards assembly of MNAi complexes.

3.1 Partzyme Oligonucleotides

In the following sequences the bases in bold hybridize with the assembly facilitator, bases underlined form part of the catalytic core of the assembled MNAzyme, and bases in italics hybridize to the substrate. The "-P" indicates 3' phosphorylation of the oligonucleotide.

SEQ ID NO 6: Partzyme A RO5A4/2-P:
CAAACGAGTCCTGGCCTTGTCT<u>ACAACGA</u>*GAGGAAACCTT*-P SEQ ID NO 7: Partzyme B RO5B5/2-P:
*TGCCCAGGGA*<u>GGCTAGCT</u>GTGGAGACGGATTACACCTTCCCACTTGC-P 3.2 Reporter Substrate The reporter substrate for this example is SubBi-2-FB with the sequence, 5' to 3', as below. SubBi-2-FB was end-labelled with a 6-FAM moiety at the 5' end and a BHQ1 moiety at the 3' end. Cleavage of SubBi-2-FB was monitored at 530 nm (FAM emission wavelength) with excitation at 485 nm (FAM excitation wavelength). The lower case bases represent RNA and the upper case bases represent DNA.

SEQ ID NO: 4 SubBi-2-FB: AAGGTTTCCTCguCCCTGGGCA 3.3 Regulator Oligonucleotides.

Several molecules were tested in this example for their ability to regulate the assembly of MNAzymes and/or MNAi. The sequence, which constitutes assembly facilitator F2, is also contained within the sequences of facilitator F1/2 and the activity inhibitor and is in bold and underlined.

SEQ ID NO 8: Assembly Facilitator F 1/2:
GCAAGTGGGAAGGTGTAATCCGTCT<u>CCACAGACAAGGCCAGGACTCGTTT</u>

<u>G</u>

SEQ ID NO: 9 Assembly Facilitator F1:
GCAAGTGGGAAGGTGTAATCCGTCT

SEQ ID NO: 10 Assembly Facilitator F2:
<u>CCACAGACAAGGCCAGGACTCGTTTG</u>

SEQ ID NO: 11 Activity inhibitor molecule:
AAGGTTTCCTCGTCCCTGGGCA<u>CCACAGACAAGGCCAGGACTCGTTTG</u>

3.4 Reaction Components and Monitoring of MNAzyme Activity.

Real time monitoring of MNAzyme activity was performed on a BMG LabTech FluoStar fluorometer in a total reaction volume of 50 μL. Reactions were monitored isothermally at 55° C. for 4 minutes. The reaction was initiated by injection of the fluorescent substrate SubBi-2-FB (10 μl of 1 μM solution) into reaction mixture containing 1×PCR Buffer II (Applied Biosystems), 25 mM $MgCl_2$, 200 nM of Partzyme A RO5A4/2-P, 200 nM of Partzyme B RO5B5/2-P and either (i) 400 nM of Assembly Facilitator F1/2, or (ii) 400 nM of Assembly Facilitator component F1 and 400 nM of Assembly Facilitator component F2, or (iii) 400 nM of Activity inhibitor and 400 nM of Assembly Facilitator component F1, or (iv) no Assembly facilitator.

3.5 Results:

The results using the combinations of various regulatory or structural component oligonucleotides are shown in FIG. 5. A rapid increase in fluorescent signal, indicative of high level of MNAzyme cleavage activity, was seen in reactions containing either assembly facilitator F1/2 (FIG. 5 (i)), or assembly facilitator components F1 and F2 (FIG. 5 (ii)). No increase in fluorescence over time was observed in the absence of a facilitator (FIG. 5 (iv)). This demonstrates that an assembly facilitator need not always be an unbroken oligonucleotide, but rather can be split into multiple shorter facilitator components, which align adjacent to each other on one of the sensor arms of a partzyme.

No increase in fluorescent signal was observed over time in reactions containing the activity inhibitor and facilitator F1 (FIG. 5 (iii)). Since the activity inhibitor molecule includes the sequence of facilitator F2, then the additional non-complementary inhibitory sequence adjoined to facilitator F2 is the element driving the assembly of MNAi complexes. The MNAi can bind to a substrate but cannot catalytically modify it. As a result, the substrate was not cleaved and fluorescence did not increase over time in the presence of MNAi complexes (FIG. 5 (iii)). Comparison between reactions containing the assembly facilitator components F1 and F2 (FIG. 5 (ii)), with those containing the assembly facilitator F1 and the activity inhibitor (which incorporates the F2 sequence) (FIG. 5 (iii)), demonstrates that the presence of an inhibitory domain within an activity inhibitor can provide a tool with which to regulate enzymatic activity by driving the assembly of MNAi complexes and preventing the formation of active MNAzymes.

Thus an MNAzyme, designed to form in the presence of an assembly facilitator F1/2, generated fluorescence. The example demonstrated that the assembly facilitator F1/2 could be split into two parts (assembly facilitator components F1 and F2) and retain the capacity to direct the assembly of catalytically active MNAzymes. Together the two assembly facilitator components can stabilise active MNAzyme formation and cause fluorescence, provided they bind adjacent to each other on the partzyme sensor arm. Subsequent experiments, performed under identical reaction conditions, demonstrated that no increase in fluorescence over time was observed in the presence of assembly facilitator component F2 only (data not shown). As such, this example demonstrates the assembly of partzymes into active MNAzymes can require the presence of multiple component assembly facilitators. When multi-component assembly facilitators are required, the presence or absence of one or more of these components can be used to control the assembly of active MNAzymes and as such switch them on and off.

It was further discovered that an activity inhibitor molecule could prevent MNAzyme assembly by hybridising to a partzyme and disrupting the secondary structure at the junction of the two assembly facilitator component on a partzyme sensor arm which is required for enzymatic activity (see FIGS. 4 and 5 as examples). It would be appreciated by one skilled in the art, that an inhibitory molecule could be designed to hybridise to either partzyme A or B, and to either the sensor or substrate arm of partzyme.

Molecules including activity inhibitors, partzyme stabilizer arm components and assembly facilitators or components thereof, can be used to regulate the assembly of active MNAzymes and inactive states such as an MNAi. Transition between states of activation (MNAzyme) and inactivation (such as MNAi) can provide a mechanism for creating a molecular switch, which can be regulated by alternating between the active and inactive conformations. Such molecular switches could be applied to the control of nucleic acid replication cascades (FIG. 6, Example 4), or to the regulation of autonomous therapeutic, diagnostic and computational molecular scale devices. Various protocols which can be employed to induce the dissociation of a specific oligonucleotide component are discussed throughout this document.

Example 4

Signal Cascade Using DNA (SCUD)

One mechanism for generating an MNAzyme replication cascade designed for target analyte detection uses the SCUD cascade strategy. The SCUD strategy can be incorporated into cascades in a variety of designs as illustrated, by way of example, in FIG. 6, where two MNA complexes are incorporated; in FIG. 10, where three MNA complexes are incorporated; and in FIG. 11 where both MNA complexes and a DNAzyme are incorporated in a cascade reaction.

The SCUD method relies on the ability to control the assembly of active MNAzymes and MNAi from component oligonucleotides present in the mix. One format of SCUD is depicted in FIG. 6. This SCUD example describes a general method for signal amplification.

One schema of the method, known as SCUD (Signal Cascade using DNA), as illustrated in FIG. 6 contains the following components:
(i) a dual labelled RIF (Reporter-Inhibitor-Facilitator) containing three regions;
   a. an activity inhibitor/reporter (RI) domain which has the dual functions of firstly being an activity inhibitor when incorporated into RIF and secondly providing a fluorescent signal when RIF is cleaved, and
   b. an activator assembly facilitator component F2b which forms an essential component of MNAzyme 2a,
   c. a substrate domain located between the RI and F2b domains, which may be cleaved by either MNAzyme 1a or MNAzyme 2a,
(ii) an assembly facilitator component F2a
(iii) partzymes capable of forming active MNAzyme 1a structures only in the presence of assembly facilitator F1, which by way of example may be a target nucleic acid present in a test sample; the active MNAzyme 1a being capable of cleaving RIF into RI and F2b components, thus generating fluorescence, negating the MNAzyme activity inhibitory effect and concomitantly generating a new activator assembly facilitator component F2b.
(iv) partzymes capable of forming active MNAzyme 2a complexes only when the partzyme arms bind assembly facilitator component F2a adjacent to the liberated activator assembly facilitator component F2b. The MNAzyme 2a in turn could cleave more RIF liberating more RI and F2b thus creating a cascade of MNAzyme 2a self replication and concomitant fluorescent signal amplification.

In the absence of F1, which by way of example could be a target nucleic acid, the partzymes for MNAzyme 2a would form an inactive complex, MNAi 21, with intact RIF. In the presence of target analyte, active MNAzyme 1a would form, thus cleaving RIF and liberating an activator assembly facilitator component F2b which would then be free to associate and become a component of an active MNAzyme 2a. Since MNAzyme 2a can further cleave more RIF, this would initiate the replication/signal amplification cascade.

Each time an MNAzyme 2a cleaves a RIF molecule, more components (activator F2b assembly facilitators) required for formation of new MNAzymes 2a would be generated. The MNAzyme cascade results in the assembly of MNAzyme 2a complexes that are identical to the parent MNAzyme using components which are the products generated by MNAzyme 2a catalytic activity. As such, the product of the MNAzyme cleavage (F2b) is able to direct the assembly of new (parent) MNAzyme molecules in a self-replicating system which is autocatalytic.

SCUD could be initiated by either nucleic acid targets (DNA/RNA), or other target analytes (proteins, small molecules etc), if the SCUD strategy was linked with an apta-MNAzyme system. Since the reaction is only initiated in the presence of target analytes, it provides a technique for detection and/or identification of target analytes. The method is based on the transition between states of inactivation and activation of multicomponent nucleic acid complexes. Unlike target amplification techniques such as the polymerase chain reaction, or the ligase chain reaction, MNAzyme replication and signal amplification by SCUD requires no protein enzymes to facilitate the process. Further, the ability to control and regulate the catalytic activity of MNAzyme using several oligonucleotide components, such as stabiliser arm components or assembly facilitator components allows the assembly of MNAzymes to be tightly regulated by conditions and components in the microenvironment.

Example 5

Application of MNAzymes to Detect Non-Nucleic Acid Analytes Including Small Molecules Such as Adenosine 5'-Triphosphate Aptamers are single-stranded DNA or RNA molecules evolved in vitro from large pools of random-sequence oligonucleotides for their capacity to bind target analytes with high affinity and specificity. Aptamers have been selected for their ability to bind specifically to many types of analytes including proteins, carbohydrates, lipids, nucleotides, whole cells and viruses. In this example, an aptamer sequence was incorporated at the end of a partzyme (apta-partzyme) in a configuration whereby an active apta-MNAzyme was only formed in the presence of the activator ligand. There are several ways of achieving this goal, including the strategy used in the following example, which is illustrated in FIG. 7.

The nucleic acid oligonucleotides included in this exemplary apta-MNAzyme detection strategy are illustrated in FIG. 7 and include;

a) a standard partzyme;
b) an apta-partzyme which is a partzyme with an aptamer incorporated into one of its ends;
c) an assembly facilitator which binds to both the apta-partzyme and the partzyme enabling assembly of an active MNAzyme;
d) a reporter substrate; and
e) an assembly inhibitor oligonucleotide which hybridises to the apta-partzyme in a region which spans at least part of the aptamer sequence and part of the substrate binding arm of the partzyme sequence.

In the absence of an activator ligand (FIG. 7, panel (i)), the assembly inhibitor oligonucleotide binds to the apta-partzyme thus preventing it from binding to the substrate. In the presence of an activator ligand (FIG. 7, panel (ii)), the activator ligand can interact with the aptamer sequence of the apta-partzyme, thus preventing binding of the assembly inhibitor and allowing an active apta-MNAzyme to assemble, then bind to and cleave the substrate. As such, apta-MNAzymes can only form and cause fluorescent signal generation in the presence of an activator ligand.

The strategy was demonstrated using detection of a small molecule, ATP. The 27 nucleotide long aptamer sequence used in this example has been previously reported as being highly specific for binding of ATP and dATP (Achenbach, 2005, Huizenga and Szostak, 1995).

5.1 Partzyme Oligonucleotides, Assembly Facilitator and Inhibitory Oligonucleotides In this example the ATP aptamer sequence was adjoined to the substrate arm of a partzyme, to produce an apta-partzyme molecule (FIG. 7). The sensor arms of the apta-partzyme and the standard partzyme were designed to bind to a synthetic assembly facilitator, included in the reaction to drive the assembly of MNAzymes when targets or regulatory analytes are present. The sequences of apta-partzyme AtpA2/1 and partzyme AtpB3/1 are shown below (5' to 3'). In the following sequences the bases in bold hybridize with the assembly facilitator, bases underlined form part of the catalytic core of the assembled MNAzyme, and bases in italics hybridize to the substrate. In addition, bases in plain text in partzyme AtpA2/1 indicate a DNA aptamer sequence that can bind to ATP or dATP.

SEQ ID NO: 12 Apta-Partzyme A2 AtpA2/1:
AACGTACACTGCACGCGGTCGAAA*TAGTGAGTACCTGGGGGAGTATTGCG*

*GAGGAAGGT*

SEQ ID NO: 13 Partzyme B3 AtpB3/1:
*CATCTCTTCT*CCGAGCGTCTGTACCGTGTAC

The sequence of the assembly facilitator is shown below (5' to 3')

SEQ ID NO: 14 Assembly facilitator AtpC/1:
GTACACGGTACAGACCGTGCAGTGTACGTT

The sequence of the "assembly inhibitor" oligonucleotide is shown below (5' to 3').

SEQ ID NO: 15 Assembly Inhibitor AtpR/1:
CCAGGTACTCACTATT 5.2 Reporter Substrate Apta-MNAzyme activity was monitored by cleavage of a dual-labelled nucleic acid reporter substrate. The reporter substrate for this example is SubBi-1-FB with the sequence, 5' to 3', as below. The lower case base represents RNA and the upper case bases represent DNA. The underlined bases indicate the position of a 6-FAM moiety at the 5' end and a BHQ1 moiety at the 3' end. Changes in fluorescence due to cleavage of SubBi-1-FB at the ribonucleotide between the FAM and BHQ1 were monitored at 520 nm (FAM emission wavelength) with excitation at 490 nm (FAM excitation wavelength).

SEQ ED NO: 16 SubBi-1-FB: ACTCAC<u>T</u>ATaGGAAGAGA<u>T</u>G 5.3 Target or Regulatory Analytes and Control Molecules The activator ligands used for this example were adenosine 5'-triphosphate (ATP) and deoxyadenosine 5'-triphosphate (dATP). Guanosine 5'-triphosphate (GTP) and cytosine 5'-triphosphate (CTP) were used as negative control molecules. All molecules were purchased from Bioline. Nuclease-free water was used as a no analyte control.

5.4 Reaction Conditions

The presence of the activator ligand was measured by an increase in fluorescent signal caused by cleavage of the reporter substrate by the catalytically active apta-MNAzyme. Reactions were initiated by the addition of substrate and the total volume of all reactions was 50 µL. Prior to substrate injection, all reactions were pre-incubated at 60° C. for 5 minutes (to reduce secondary structure). Reactions were conducted at 47° C. on a FLUOstar OPTIMA (BMG Biotech). Fluorescence for each reaction was read every 3 seconds for a total of 10 minutes. Each reaction contained a final concentration of 200 nM AtpA2/1, 200 nM AtpB3/1, 200 nM AtpC/1, 200 nM AtpR/1, 200 nM SubBi-1-FB, 25 mM $MgCl_2$, 50 mM Tris HCl pH 7.5 and 2 mM of either ATP, or dATP, or GTP, or CTP or no analyte (water control).

5.5 Results: Detection and Cleavage of SubBi-1-FB Reporter Substrate

In the absence of ATP or dATP a low level of fluorescence was seen which did not increase over time, demonstrating that in the absence of ATP, the assembly inhibitor prevented the assembly of active apta-MNAzyme/substrate complexes. In the presence of ATP or dATP, the fluorescent signal was higher and it increased over time. This indicates that the inhibitor oligonucleotide was displaced by dATP and ATP and an active apta-MNAzyme was formed. Assembly of the apta-MNAzyme was ligand-dependent. In the presence of GTP or CTP a low level of fluorescence was seen which did not increase over time. The fluorescence observed in the presence of GTP or CTP was similar to that observed in the absence of ATP or dATP i.e. in the no ligand water control. This example demonstrates that MNAzymes can be coupled to aptamers for the detection of analytes in an approach that is highly specific for the target analyte. This example further demonstrates that an assembly inhibitor molecule can be used to control the assembly of apta-MNAzymes, and that ATP can serve as a activator ligand or molecular regulator in this system.

One skilled in the art will recognise that the design of this strategy can be flexible. The aptamer can be incorporated into either end (5' or 3') of either of the two partzymes containing partial catalytic core sequences. As such, the assembly inhibitor can bind to the aptamer region and to either the substrate arm (that binds the substrate) or the sensor arm (that binds the assembly facilitator). In the former design (FIG. 7 and this example), the inhibitor blocks binding of the substrate. In the latter design, the inhibitor would prevent binding of the assembly facilitator with the apta-partzyme and therefore would prevent assembly of active MNAzymes.

The literature contains sequences for a large number of aptamers capable of detecting many types of analytes. These include proteins, carbohydrates, lipids, prions, nucleotides, whole cells and viruses. Aptamers to all these types of analytes could be linked to partzymes to detect a very diverse range of molecules. Reaction conditions (buffer, temperature, divalent cation concentration etc), which are compatible with both binding of analytes to aptamers (or apta-partzymes) and cleavage of a reporter substrate by an MNAzyme, can be determined by empirical testing.

MNAzyme activity can be modulated by the removal or addition of the assembly inhibitor. Changing the oligonucleotide sequence, the melting temperature and or concentration can achieve finer regulation. The hybridization of the assembly inhibitor within an MNAis affected by many factors, including but not limited to, salt concentration, cation concentration, temperature and the presence or absence of additives (eg DMSO). As such, entities that affect hybridization can provide a tool for controlling the assembly and disassembly of MNA complexes, The assembly facilitator, assembly inhibitor or other MNA components can be removed by physical manipulation, for example, by exploiting either physical properties of attached moieties as molecular "hooks", and/or by exploiting inherent properties of the oligonucleotides, for example, negative charge, or sequence complementarity.

Example 6

A Molecular Switch, which Uses a DNAzyme with Ligase Activity and an MNAzyme with Cleavage Activity A molecular switch exploiting the catalytic activities of two DNA enzymes is outlined in FIG. 8. The first reaction is mediated by an MNAzyme which can cleave an RNA containing oligonucleotide into 2',3'-cyclic phosphate and 5'-hydroxyl products. The second reaction is mediated by a DNAzyme ligase, which can ligate 2',3'-cyclic phosphate and 5'-hydroxyl products. Examples of such DNAzymes are known in the art and include, by way of example the "7Z81" and "7Z48" ligases (Prior et al, 2004).

In the simplest format, oligo 1/2 can be cleaved by an MNAzyme into cleavage products oligo 1 and oligo 2, thus regenerating 2',3'-cyclic phosphate and 5'-hydroxyl products, which can participate in a subsequent round of ligation. A DNAzyme ligase can then use the cleavage products as substrates for ligation. A DNAzyme can ligate the first oligonucleotide product (oligo 1) to a second oligonucleotide product (oligo 2) to create a ligation product which has the same sequence as oligo 1/2.

In a multiplex format, several oligonucleotides, for example four oligonucleotides, could be cleaved by an MNAzyme into products with 2',3'-cyclic phosphate and a 5'-hydroxyl termini. These could be ligated by a set of 16 DNAzyme ligases into 16 new unique ligation products (i.e. each combination of oligonucleotides 1, 2, 3 and 4).

Additional MNAzymes could cleave one or more of the 16 ligation products oligos at site(s) other than the original junction between oligonucleotides 1, 2, 3 and/or 4, provided the minimal sequence requirements for MNAzyme cleavage are met. For example, the MNAzyme in example 1 requires the presence of a purine pyrimidine ribonucleotide at the cleavage site within the substrate.

A set of MNAzymes may use a common assembly facilitator and/or the MNAzyme can use the ligation products from previous ligation rounds as its assembly facilitator. As such, new information (input) data produced by the ligation of oligonucleotides can be recognized "read" by the MNAzyme. The MNAzyme can then cleave "write" to produce a new output product, and/or information. Systems where MNAzymes can read the input ligation products, and then cleave into product oligos, other than those originally in the pool of starting molecules, can be used to rewrite or recode new output sequences.

In some embodiments ligation by a DNAzyme can "write" input data, for example, by making new assembly facilitators, or components thereof. An MNAzyme can "read" the data, by interrogating the information encoded within the assembly facilitator using the partzyme sensor arms. The MNAzyme can then "write" data, for example, a new sequence (a cleavage product) thus creating new output data which can then be "read" by a DNAzyme ligase (by ascertaining the suitability of MNAzyme cleavage products to serve as substrates for the DNAzyme ligase).

As such, this MNAzyme/DNAzyme ligase cascade can form an automaton. Such devices are capable of converting information from one form into another, according to a defined procedure. In this case the procedures are encoded and directed by the substrate arms and/or the sensor arms of the MNAzymes and DNAzyme ligases.

An automaton, which was capable of solving computational problems was developed by Benenson et al, 2001, using DNA and protein enzymes (a restriction endonuclease and a ligase). The restriction endonuclease cleaved the double stranded DNA and the protein ligase ligated the cleavage products in a cascade reaction. The protein enzymes served as the "hardware" and the DNA encoded the "software". The input and automaton were programmed by selection of the appropriate DNA software sequences. The automaton proceeded via a cascade of restriction endonuclease cleavage, hybridization and ligation cycles, producing a detectable output molecule that encoded the automaton's final state and thus the computational result (Benenson et al, 2001).

The MNAzyme/DNAzyme ligase cascade could be used in a similar manner to the cascade used by Benenson et al (2001) and thus provide a device capable of solving computational problems. Unlike Benenson's device, a MNAzyme/DNAzyme ligase cascade, requires no protein enzymes to achieve the same results. While Benenson's device was programmed by double stranded DNA, a MNAzyme/DNAzyme ligase cascade would be encoded by the various sequences, including for example, the initial input oligonucleotide(s), the substrate arms and/or the sensor arms of the MNAzymes and the substrate arms of DNAzyme ligases.

In another embodiment, the MNAzyme/DNAzyme ligase cascade could also be used to "shuffle" oligonucleotide sequences as a method of constructing, and/or increasing the diversity of, molecular libraries.

In one embodiment, DNAzyme ligases can be used to create or destroy components of MNAzyme and or inactive MNAs. By way of example a DNA ligase could attach an "activity inhibitor" to an "assembly facilitator component" resulting in the assembly of MNAi ("off" state). Alternatively a DNAzyme ligase could attach a sensor or substrate arm to a partzyme component to create an "on" switch for MNAzymes by promoting assembly as illustrated in FIG. 11 aspects (ii) and (iv). In another embodiment, the DNAzyme ligase can attach a sequence labeled with a moiety that allow oligonucleotides to be selectively captured, for example using a biotin group or the moiety could contain a radio-frequency magnetic field radio to facilitate remote electronic control of hybridisation. This approach would allow selective removal of component molecules allowing activation or inhibition of enzymatic activity. For example, the activity inhibitor can be selectively denatured from an MNAi complex allowing transition to the active MNAzyme state.

In some embodiments ligation by a DNAzyme can "write" input data, for example, by making new assembly facilitators, or components thereof. An MNAzyme can "read" the data, by interrogating the information encoded within the assembly facilitator using the partzyme sensor arms. The MNAzyme can then "write" data, for example, a new sequence (a cleavage product) thus creating new output data which can then be "read" by additional DNAzyme ligases by ascertaining the suitability of MNAzyme cleavage products to serve as a substrate.

Example 7

One Exemplary Structure for an MNAzyme and MNAi Molecular Switch

The assembly facilitator required for active MNAzyme formation can comprise two or more component oligonucleotides. The presence or absence of an activity inhibitor oligonucleotide can promote the formation of MNAi structures. One skilled in the art will recognise that there are many designs for such MNAzymes and MNAis. Some examples of active MNAzyme structures are shown in FIG. 9 (Panels A to D; left hand side structures). Examples of MNAi structures are shown in FIG. 9 (Panels A to D; structures to the right of the active MNAzymes). This example demonstrates those structures illustrated in FIG. 9 panel B structures c (MNAzyme) and d (MNAi).

The MNAzyme used in this experiment was made up of the partzymes RO5A4/2 and 5FAC2B5(6)/2(16), which are designed to cleave the reporter substrate SubBi-2-FB following assembly directed by two oligonucleotides called Assembly Facilitator 1 (FAC2) and Assembly Facilitator 2 (d6p-1). This experiment also shows that the formation of complexes comprising an activity inhibitor produces MNAi complexes.

7.1 Partzyme Oligonucleotides

In the following sequences the bases in bold hybridize with the target nucleic acid (or assembly facilitator) sequence(s), bases underlined form part of the catalytic core of the assembled MNAzyme, and bases in italics hybridize to the substrate.

SEQ ID NO: 17 Partzyme A RO5A4/2:
CAAACGAGTCCTGGCCTTGTCTACAACGAGAGGAAACCTT

SEQ ID NO: 18 Partzyme B 5FAC2B5(6)/2(16):
*TGCCCAGGGA*GGCTAGCTCTGTCCGAGGCGTGAT

7.2 Reporter Substrate

The reporter substrate for this example was SubBi-2-FB with the sequence 5' to 3', as below. SubBi-2-FB was end-labelled with a 6-FAM moiety at the 5' end and a BHQ1 moiety at the 3' end. Cleavage of SubBi-2-FB was monitored at 530 nm (FAM emission wavelength) with excitation at 485 nm (FAM excitation wavelength). The lower case bases represent RNA and the upper case bases represent DNA.

SEQ ID NO: 4 SubBi-2-FB: AAGGTTTCCTCguCCCTGGGCA 7.3 Facilitator and Activity Inhibitor Oligonucleotides.

The sequences of the assembly facilitators used are written below 5' to 3'. The lower case bases represent RNA and the upper case bases represent DNA. The sequence in common between Assembly Facilitator 2 and the Activity Inhibitor are in bold.

Activity Inhibitor SubBi-6-TRB was end-labelled with a Texas Red moiety at the 5' end and with a BHQ2 moiety at the 3' end.

SEQ ID NO: 19 Assembly Facilitator 2 (F2) d6p-1:
ATCACGCCTCg

SEQ ID NO: 20 Assembly Facilitator 1 (F1) FAC2:
GACAGAGACAAGGCCAGGACTCGTTTG

SEQ ID NO: 21 Activity Inhibitor SubBi-6-TRB:
ATCACGCCTCguTCCTCCCAG 7.4 Reaction Components and Monitoring of MNAzyme Activity.

Real time monitoring of MNAzyme activity was performed on the SmartCycler (Cepheid) in a total reaction volume of 25 µL. Reactions were monitored isothermally at 52° C. for 30 minutes. The reactions were initiated by injection of the fluorescent substrate SubBi-2-FB (5 µl of 1 µM solution) into the reaction mixture. The reaction mixture contained 1×PCR Buffer II (Applied Biosystems), 50 mM MgCl₂, 200 nM of each Partzyme RO5A4/2 and 5FAC2B5(6)/2(16), 200 nM of facilitator FAC2 and either 200 nM of the assembly facilitator 2 (d6p-1) or 200 nM of the activity inhibitor (SubBi-6-TRB).

7.5 Results:

In this example, the assembly facilitator is made up of two oligonucleotide components. FIG. 9 shows schematic representation of the structure formed by the MNA, namely the active MNAzyme (panel B structure c) and MNAi (panel B structure d). The MNAzyme requires two assembly facilitators (F1 and F2) and two partzymes for assembly. Alternatively the activity inhibitor (I) can bind to the partzymes and form an MNAi structure.

In this experiment incubation of the partzymes and two assembly facilitators F1 and F2 resulted in the formation of active MNAzymes, which cleaved a reporter substrate and resulted in an increase in fluorescence over time of approximately 500 units (from 400 to 900 units). In contrast, incubation of the partzymes with one assembly facilitator (F1) and one activity inhibitor (I) resulted in the formation of MNAi structures, which were unable to cleave the reporter substrate. As a result only low level background increase in fluorescence was observed over time with a baseline drift of approximately 20 units (from 390 to 410 units). The assembly facilitator (F2) and the activity inhibitor (I) bind to the same regions of the partzyme since they contain common sequence. However, the additional inhibitory sequence which is present on the activity inhibitor, but not on the assembly facilitator F2, results in formation of MNAi structures. Removal of this additional inhibitory sequence from the activity inhibitor can result in generation of an activator assembly facilitator F2. As such the addition or removal of inhibitory sequences provides a mechanism for switching from active MNAzymes to MNAi's or visa versa.

Example 8

An MNAzyme and MNAi Molecular Switch

The assembly facilitator required for active MNAzyme formation can comprise two or more component oligonucleotides. The presence or absence of an activity inhibitor oligonucleotide can promote the formation of MNAi structures. One skilled in the art will recognise that there are many designs for such MNAzymes and MNAi complexes. Examples of active MNAzyme structures are shown in FIG. 9 (Panels A to D; left hand side structures). Examples of MNAi structures are shown in FIG. 9 (Panels A to D; structures to the right of the active MNAzymes). This example demonstrates those structures illustrated in FIG. 9 panel C structures e (MNAzyme) and f (MNAi).

The MNAzyme produced in this experiment was assembled from two partzymes (FACA4/6(22) and 5FAC2B5(2)/6(33)) and three assembly facilitator components, Facilitator 1 (F1) and Facilitator 2 (F2) and Facilitator 3 (F3). This experiment also shows that the formation of complexes comprising an activity inhibitor (SubBi-2-FB) and Facilitators 1 (F1) and (F3) can produce MNAi complexes.

8.1 Partzyme Oligonucleotides

In the following sequences the bases in bold hybridize with the target nucleic acid (or assembly facilitator) sequence(s), bases underlined form part of the catalytic core of the assembled MNAzyme, and bases in italics hybridize to the substrate.

SEQ ID NO: 22 Partzyme A FACA4/6(22):
CAAACGAGTCCTGGCCTTGTCTAC<u>AACGA</u>GAGGCGTGAT SEQ ID NO: 23 Partzyme B 5FAC2B5(2)/6(33):
*CTGGGAGGAA*<u>GGCTAGC</u>TCTGTCCGAGGAAACCTTCGTCGTCCAGACTGCG

8.2 Reporter Substrate

The reporter substrate for this example was SubBi-6-TRB with the sequence 5' to 3' as below. SubBi-6-TRB was end-labelled with a Texas Red moiety at the 5' end and with a BHQ2 moiety at the 3' end. Cleavage of SubBi-6-TRB was monitored at 610 nm (Texas Red emission wavelength) with excitation at 585 nm (Texas Red excitation wavelength). The lower case bases represent RNA and the upper case bases represent DNA.

SEQ ID NO: 21 SubBi-6-TRB: ATCACGCCTCguTCCTCCCAG 8.3 Facilitator and Activity Inhibitor Oligonucleotides.

The sequences of the assembly facilitators used are written below 5' to 3'. The sequence in common between Assembly Facilitator F2 and Activity Inhibitor are in bold. The lower case bases represent RNA and the upper case bases represent DNA. Activity Inhibitor SubBi-2-FB was end-labelled with a 6-FAM moiety at the 5' end and a BHQ1 moiety at the 3' end.

SEQ ID NO: 24 Assembly Facilitator F1 STAB:
CGCAGTCTGGACGACG

SEQ ID NO: 25 Assembly Facilitator F2 d2p-1:
AAGGTTTCCTCg

SEQ ID NO: 4 Activity Inhibitor SubBi-2-FB:
AAGGTTTCCTCguCCCTGGGCA

SEQ ID NO: 20 Assembly Facilitator F3 FAC2:
GACAGAGACAAGGCCAGGACTCGTTTG 8.4 Reaction Components and Monitoring of MNAzyme Activity.

Real time monitoring of MNAzyme activity was performed on the SmartCycler (Cepheid) in a total reaction volume of 25 µL. Reactions were monitored isothermally at 52° C. for 30 minutes. The reactions were initiated by injection of the fluorescent substrate SubBi-6-TRB (5 µl of 1 µM solution) into the reaction mixture. The reaction mixture contained 1×PCR Buffer II (Applied Biosystems), 50 mM MgCl₂, 200 nM of each Partzyme FACA4/6(22) and 5FAC2B5(2)/6(33), 200 nM of Facilitator F1 STAB, 200 nM of facilitator F3 FAC2 and either 200 nM of the assembly facilitator F2 (d2p-1) or 200 nM of the activity inhibitor (SubBi-2-FB).

8.5 Results:

In this example, the assembly facilitator is made up of three oligonucleotide components. FIG. 9 shows a schematic representation of the structure formed by the MNA complexes, namely the active MNAzyme (panel C structure e) and MNAi (panel C structure f). The MNAzyme requires three assembly facilitator components (F1, F2 and F3) and two partzymes for assembly of catalytically active complexes. Alternatively the activity inhibitor (I) can bind to the partzymes and form an MNAi structure.

In this experiment incubation of the partzymes and three assembly facilitator components F1, F2 and F3 resulted in the formation of active MNAzymes which cleaved a reporter substrate and resulted in an increase in fluorescence over time of approximately 330 units (from 140 to 470 units). In contrast, incubation of the partzymes with two assembly facilitators (F1 and F3) and one activity inhibitor (I) resulted in the formation of MNAi structures, which were unable to cleave the reporter substrate. As a result only low level background increase in fluorescence was observed over time with a baseline drift of approximately 40 units (from 80 to 120 units). The assembly facilitator component (F2) and activity inhibitor bind to the same regions of the partzymes since they contain common sequence. However, the additional inhibitory sequence which is present on the activity inhibitor, but not on the assembly facilitator component F2, results in formation of MNAi structures. Removal of this additional inhibitory sequence from the activity inhibitor can result in generation of an activator assembly facilitator F2 component. As such the addition or removal of inhibitory sequences provides a mechanism for switching from active MNAzymes to MNAis or visa versa.

Example 9

Another MNAzyme and MNAi Molecular Switch

The assembly facilitator required for active MNAzyme formation can comprise two or more component oligonucleotides. The presence or absence of an activity inhibitor oligonucleotide can promote the formation of MNAi structures. One skilled in the art will recognise that there are many designs for such MNAzymes and MNAi complexes. Examples of active MNAzyme structures are shown in FIG. 9 (Panels A to D; left hand side structures). Examples of MNAi structures are shown in FIG. 9 (Panels A to D; structures to the right of the active MNAzymes). This example demonstrates those structures illustrated in FIG. 9 panel D structures g (MNAzyme) and h (MNAi).

The MNAzyme in this experiment was made up of partzymes which are designed to assemble in the presence of two assembly facilitator components F1 and F2 and cleave the reporter substrate SubBi-2-FB. The sensor arm of one of the partzymes (4SYNTB6/2(8)) is truncated to 8 bases. Another oligonucleotide, the Stabilizer Arm sA (B6/tag(13)), hybridises to the assembly facilitator F1 adjacent to the truncated sensor arm of the partzyme (4SYNTB6/2(8)) thus stabilising the MNAzyme complex. The assembly facilitator has two components F1 and F2.

9.1 Partzyme Oligonucleotides

In the following sequences the bases in bold hybridize with the target nucleic acid (or assembly facilitator) sequence(s), bases underlined form part of the catalytic core of the assembled MNAzyme, and bases in italics hybridize to the substrate.

```
SEQ ID NO: 26 Partzyme A 4SYNTA5/2(22):
CAAACGAGTCCTGGCCTTCGAGTACAACGAGAGGAAACCTT SEQ ID NO: 27 Partzyme B 4SYNTB6/2(8):
TGCCCAGGGAGGCTAGCGAAACCTT
```

9.2 Reporter Substrate

The reporter substrate for this example was SubBi-2-FB with the sequence 5' to 3' as below. SubBi-2-FB was end-labelled with a 6-FAM moiety at the 5' end and a BHQ1 moiety at the 3' end. Cleavage of SubBi-2-FB was monitored at 530 nm (FAM emission wavelength) with excitation at 485 nm (FAM excitation wavelength). The lower case bases represent RNA and the upper case bases represent DNA.

```
SubBi-2-FB:
AAGGTTTCCTCguCCCTGGGCA        SEQ ID NO: 4
```

9.3 Facilitator, Activity Inhibitor and Stabiliser Arm Oligonucleotides.

The sequences of the assembly facilitator components used are written below 5' to 3'. The lower case bases represent RNA and the upper case bases represent DNA. The sequence in common between Assembly Facilitator 1 and Activity Inhibitor are in bold.

```
Assembly Facilitator F2 (RO5/cA(18)):
                                     SEQ ID NO: 28
AAGGCCAGGACTCGTTTG Assembly Facilitator F1 (r2p-SYNT/cB(25):
                                     SEQ ID NO: 29
GGGAAGGTGTAATAAGGTTTCCTCg Activity Inhibitor (2-SYNT/cB(25)):
                                     SEQ ID NO: 30
GGGAAGGTGTAATAAGGTTTCCTCguCCCTGGGCA Stabiliser Arm sA (B6/tag(13)):
                                     SEQ ID NO: 31
ATTACACCTTCCC
```

9.4 Reaction Components and Monitoring of MNAzyme Activity.

Real time monitoring of MNAzyme activity was performed on the BMG LabTech FluoStar fluorometer in a total reaction volume of 50 µl. Reactions were monitored isothermally at 40° C. for 3 minutes. The reactions were initiated by injection of the fluorescent substrate SubBi-2-FB (10 µl of 1 µM solution) into the reaction mixture. The reaction mixture contained 1×PCR Buffer II (Applied Biosystems), 25 mM $MgCl_2$, 200 nM of each Partzyme 4SYNTA5/2(22) and 4SYNTB6/2(8), 200 nM of Stabiliser Arm B6/tag(13), 200 nM of Facilitator F2 RO5/cA(18) and 200 nM of either Assembly Faciliator F1 (r2p-SYNT/cB(25)) or Activity Inhibitor (2-SYNT/cB(25))

9.5 Results:

In this example, the assembly facilitator is made up of two oligonucleotide components. FIG. 9 shows schematic representation of the structure formed by the MNA, namely the active MNAzyme (panel D structure g) and MNAi (panel D structure h). The MNAzyme requires two assembly facilitator components (F1 and F2), two partzymes and one stabiliser arm for assembly of catalytically active complexes. Alternatively the activity inhibitor (I) can bind to the partzymes and form an MNAi structure.

In this experiment incubation of two partzymes, two assembly facilitator components F1 and F2 and one stabiliser arm resulted in the formation of active MNAzymes which cleaved a reporter substrate and resulted in an increase in fluorescence over time of approximately 28,000 units (from 12,000 to 40,000 units). In contrast, incubation of the partzymes with one assembly facilitator (F2), one stabiliser arm and one activity inhibitor (I) resulted in the formation of MNAi structures which were unable to cleave the reporter substrate. Only a low level background increase in fluorescence was observed over time with a baseline drift of approximately 1,500 units (from 12,000 to 13,500 units). The assembly facilitator component (F1) and activity inhibitor (I) bind to the same regions of the partzyme and stabiliser arm since they contain common sequence. However, the additional inhibitory sequence which is present on the activity inhibitor, but not on the assembly facilitator component F1, results in formation of MNAi structures. Removal of this additional inhibitory sequence from the activity inhibitor can result in generation of an activator assembly facilitator F1 component. As such the addition or removal of inhibitory sequences provides a mechanism for switching from active MNAzymes to MNAi's or visa versa.

Example 10

A SCUD Cascade

One mechanism for generating an MNAzyme replication cascade designed for target analyte detection uses the SCUD cascade strategy. The SCUD strategy can be incorporated into cascades in a variety of designs as illustrated, by way of example, in FIG. 6, where two MNA complexes are incorporated; in FIG. 10, where three MNA complexes are incorporated; and in FIG. 11 where both MNA complexes and a DNAzyme are incorporated in a cascade reaction.

SCUD method relies on the ability to control the assembly of active MNAzymes and MNAi from component oligonucleotides present in the mix. One exemplary schema of the SCUD cascade is illustrated in FIG. 10. In this strategy an initiating MNAzyme (Mt) is formed in the presence of target (T). This initiating MNAzyme cleaves a substrate (S1) thus creating one of the activator assembly facilitator components (S1f) required for formation of cascading MNAzyme 1 (Mc1). MNAzyme 1 then cleaves the substrate (S2) thus creating an additional activator assembly facilitator component required for formation of cascading MNAzyme 2 (Mc2). MNAzyme 2 then cleaves the substrate (S1) thus initiating a cascade reaction.

The following experimental example demonstrates the capacity of an initiating MNAzyme (Mt) to cleave a substrate (S1) into two fragments in the presence of target. It further demonstrates that the initiating MNAzyme (Mt) can cleave the S1 substrate into fragments one of which (S1f) can function as an activator assembly facilitator component which, together with two other facilitator components (F1 and F2), can form an MNAzyme Mc1, which is capable of cleaving a second substrate (S2).

In this experiment the initiating MNAzyme Mt was composed of partzymes RO5A5/2-P and RO5B6/2-P, which are designed to detect a section of the human RPLPO gene (RO5Target) and cleave the S1 substrate SubBi-2h-FB. A cleaved fragment of SubBi-2h-FB (SU) along with the F1 and F2 assembly facilitator components FAC5 and FAC6 bind to the sensor arms of the Mc1 cascading MNAzyme 1 comprising the partzymes CasA4(2h)/6 and CasB5(2h)/6. The fully assembled active cascading MNAzyme 1 was designed to cleave the substrate SubBi-6-TRB.

10.1 Partzyme Oligonucleotides

In the following sequences the bases in bold hybridize with the target nucleic acid (or assembly facilitator) sequence(s), bases underlined form part of the catalytic core of the assembled MNAzyme, and bases in italics hybridize to the substrate. The "-P" indicates 3' phosphorylation of the oligonucleotide.

```
Partzyme A RO5A5/2-P:
                                         SEQ ID NO: 51
CAAACGAGTCCTGGCCTTGTCTTACAACGAGAGGAAACCTT-P
```

-continued
```
Partzyme B RO5B6/2-P:
                                         SEQ ID NO: 32
TGCCCAGGGAGGCTAGCGTGGAGACGGATTACACCTTC-P Partzyme A CasA4(2h)/6:
                                         SEQ ID NO: 33
GTATCGTGTGTTCTTGCCCTCGTGCCCACAACGAGAGGCGTGAT Partzyme B CasB5(2h)/6:
                                         SEQ ID NO: 34
CTGGGAGGAAGGCTAGCTAGGGACGCACTCCTACCTCTA
```

10.2 Reporter Substrate

The S1 and S2 reporter substrates for this example were SubBi-2h-FB and SubBi-6-TRB, with the sequences 5' to 3', as below. SubBi-2h-FB was end-labelled with a 6-FAM moiety at the 5' end and internally labelled with a BHQ1 moiety at the 3' end. SubBi-6-TRB was end-labelled with a Texas Red moiety at the 5' end and with a BHQ2 moiety at the 3' end. The underlined bases indicate the position of the fluorophores. Cleavage of SubBi-2h-FB was monitored at 530 nm (FAM emission wavelength) with excitation at 485 nm (FAM excitation wavelength). Cleavage of SubBi-6-TRB was monitored at 610 nm (Texas Red emission wavelength) with excitation at 585 nm (Texas Red excitation wavelength). The lower case bases represent RNA and the upper case bases represent DNA.

```
SubBi-2h-FB:
AAGGTTTCCTCguCCCTGGGCACACGAGG    SEQ ID NO: 35

SubBi-6-TRB:
ATCACGCCTCguTCCTCCCAG            SEQ ID NO: 21
```

10.3 Facilitator Oligonucleotides.

Two molecules were used in this example as the assembly facilitator components to hybridize to the sensor arms of the partzymes CasA4(2h)/6 and CasB5(2h)/6. The sequences of the F1 and F2 assembly facilitators FAC5 and FAC6 are written below 5' to 3'.

```
Assembly Facilitator F1 FAC5:
GCAAGAACACACGATAC                SEQ ID NO: 36

Assembly Facilitator F2 FAC6:
TAGAGGTAGGAGTGCG                 SEQ ID NO: 37
```

10.4 Target Sequences.

The target sequence for this example was a synthetic oligonucleotide RO5Target with the sequence, 5' to 3', as below. This target sequence has the same sequence as a section of the human RPLPO gene, exon 5.

```
RO5Target:
                                         SEQ ID NO: 38
GAAGGTGTAATCCGTCTCCACAGACAAGGCCAGGACTCGTTTG
```

10.5 Reaction Components and Monitoring of MNAzyme Activity.

Real time monitoring of MNAzyme activity was performed on the SmartCycler (Cepheid) in a total reaction volume of 25 μL. Reactions were monitored isothermally at 50° C. for 12 minutes. The reactions were initiated by injection of the fluorescent substrates SubBi-2h-FB and SubBi-6-TRB (5 μl of 2.5 μM solution of each substrate for a final concentration of 0.5 μM each) into the reaction mixture. The reaction mixture contained 1×PCR Buffer II (Applied Biosystems), 25 mM $MgCl_2$, 500 nM of each Partzyme RO5A5/2-P, RO5B6/

2-P, CasA4(2h)/6 and CasB5(2h)/6, 500 nM of each facilitator component FAC5 and FAC6 and either 100 nM of RO5Target or no target (H$_2$O) control.

10.6 Results:

In the presence of RO5 target sequence, the partzymes RO5A5/2-P and RO5B6/2-P formed an initiating MNAzyme Mt, which cleaved the S1 substrate SubBi-2h-FB resulting in an increase in FAM fluorescence of approximately 1250 units (from 1200 to 2450 units). The cleaved S1 substrate resulted in generation of a S1f facilitator fragment which then functioned in concert with the F1 and F2 facilitator components FAC5 and FAC6 and the partzymes CasA4(2h)/6 and CasB5 (2h)/6 to form the Mc1 cascading MNAzyme 1. This MNAzyme 1 then cleaved the second S2 substrate SubBi-6-TRB thus causing an increase in the fluorescence of Texas Red of approximately 900 units (from 250 to 1150 units). As such, an increase in fluorescence of both FAM and Texas Red is indicative of the presence of the target sequence in this MNAzyme cascade reaction.

In the absence of RO5 target sequence, no increase in fluorescence of FAM was observed over time and only low level background increase in fluorescence was observed over time for Texas Red with a baseline drift of approximately 100 units (from 240 to 340 units). When target is not present, the partzymes RO5A5/2-P and RO5B6/2-P cannot form an initiating MNAzyme Mt and hence the S1 substrate SubBi-2h-FB is not cleaved and FAM fluorescence does not increase. In the absence of cleaved S1 substrate, no S1f facilitator fragment is present to direct formation of a Mc1 cascading MNAzyme 1. While the uncleaved S1 substrate SubBi-2h-FB can still bind to the complex comprising facilitators FAC5 and FAC6 and the partzymes CasA4(2h)/6 and CasB5(2h)/6 this results in an MNAi structure which is incapable of cleaving the S2 substrate SubBi-6-TRB. Consequently the level of fluorescence of Texas Red remains low. The absence of a significant increase in the fluorescence of both FAM and Texas Red is indicative of the absence of the target sequence in this MNAzyme cascade reaction.

Example 11

Detection of Target Using an Initiating MNAzyme Event Followed by SCUD Feedback Cascade Amplification and then DNAzyme Ligase Mediated MNAzyme Cleavage Readout The strategy used in this example is illustrated in FIG. 11. This example demonstrates aspects of the strategy as illustrated in the sections (i) to (iv) in the figure.

(i) A target nucleic acid (F1) directs the formation of an MNAzyme 1a which cleaves a substrate A and generates two cleavage products, product Aa which is required as a component in a ligation reaction (section ii) and a second product Ab which is required as an activator assembly facilitator in the aspect indicated in section (iii).

(ii) The product Aa has a 2',3'-cyclic phosphate at its 3' terminus and thus is suitable to function as a substrate for DNAzyme 2a, which has ligase activity. DNAzyme ligase 2a ligates the product Aa generated in the aspect in section (i) to another oligonucleotide ligation substrate B thus creating a new partzyme for MNAzyme 4a.

(iii) The product Ab functions as an activator assembly facilitator which directs the formation of active MNAzyme 3a from partzyme components. MNAzyme 3a cleaves substrate A generating two products Aa and Ab. The product Ab can then function as an activator assembly facilitator, which directs the formation of more active MNAzyme 3a. This MNAzyme 3a system results in a SCUD autocatalytic self replication feedback amplification cascade. This SCUD cascade results in further accumulation of Ab, which can function as a activator assembly facilitator for MNAzyme 3a, and in the accumulation of Aa, which can function as a substrate for DNAzyme 2a.

(iv) The ligation product generated by ligation of Aa and Substrate B forms a new ligated partzyme for MNAzyme 4a. MNAzyme 4a forms together with facilitator F4 and cleaves substrate C between a fluorophore and quencher dye pair resulting in an increase in fluorescent signal indicative of the presence of target nucleic acid F1.

In this example aspects (i), (ii) and (iii) occurred concurrently in a single tube at a single temperature. The readout detection step (aspect iv) was performed following the addition of further reagents to the reaction. The DNAzyme ligase used in this example has previously been reported to ligate RNA through the formation of a 2'-5' phosphodiester linkage from a 2',3'-cyclic phosphate and a 5'-hydroxyl group (Silverman et al). Apart from the requirement of a 5' substrate with a 2',3'-cyclic phosphate end, the DNAzyme ligase used in this example also requires a specific sequence motif at the ligation junction, being UA*G(A or G) (where * denotes the ligation site).

11.1 DNAzyme Ligase B

The DNA oligonucleotide sequence, which acts as a DNAzyme ligase is listed below.

```
SEQ ID NO 39:
DNAzyme ligase 7Z81-10/10:
CCTCTCGTTGACGGCGGAGTGATTGGGAGGTTAGCTCTAGTGAGTGC
```

11.2 Partzyme Oligonucleotides

In the following sequences the bases in bold hybridize with the target nucleic acid sequence, bases underlined form part of the catalytic core of the assembled MNAzyme, and bases in italics hybridize to the substrate.

The following are sequences of the partzymes, which form components of MNAzyme 1a:

```
Partzyme A miR20A2/1:
TACCTGCACTACGGTCGAAATAGTGAGT    SEQ ID NO: 40

Partzyme B miR20B3/1:
CATCTCTTCTCCGAGCTAAGCACTTTA     SEQ ID NO: 41
```

The following sequence corresponds to the partzyme, which associates with the ligation product/partzyme to form a component of MNAzyme 4a.

```
Partzyme B STB5/2(21):
                                SEQ ID NO: 42
TGCCCAGGGAGGCTAGCTCTGTCGTCGGAGTGGTCGTCG
```

The following are sequences of the partzymes, which form components of SCUD MNAzyme 3a:

```
Partzyme A 4SYNTA2/1i-10HP:
                                SEQ ID NO: 43
GGATGGGCACTAACGTGCCCATCCCATCTCCGGTCGAAATAGTGAGT Partzyme B 4SYNTB3/1i-12HP:
                                SEQ ID NO: 44
CATCTCTTCTCCGAGCTTCCCATCTCACGACGATAACGTCGTGAGATG
```

11.3 MNAzyme Substrate A (Substrate for MNAzyme 1a and 3a)

In the following sequence, the lower case bases represent RNA and the uppercase bases represent DNA.

```
preSub5:
CTGTAGCACTCACTAuaGGAAGAGATG     SEQ ID NO: 45
```

11.4 DNAzyme Ligase Substrate B

In the following sequence, the lower case base represents RNA and the uppercase bases represent DNA. The 3' DNAzyme ligase substrate was synthesised to have the sequence below and a 5' hydroxyl group:

```
preSub3:
gGAACAACGAGAGGAAACCTT           SEQ ID NO: 46
```

11.5 MNAzyme Substrate C (Fluorescent Reporter Substrate for MNAzyme 4a)

The reporter substrate used in this example was SubBi-2. In the current example, SubBi-2 was end-labelled with a 6-FAM moiety at the 5' end, a BHQ1 moiety at the 3' end and designated SubBi-2-FB. Cleavage of SubBi-2-FB was monitored at 520 nm (FAM emission wavelength) with excitation at 490 nm (FAM excitation wavelength). The sequence of SubBi-2-FB is listed below (5' to 3'); the lower case bases represent RNA and the upper case bases represent DNA.

```
SubBi-2-FB:
AAGGTTTCCTCguCCCTGGGCA          SEQ ID NO: 4
```

11.6 Target Sequence F1 for MNAzyme 1a

The target sequence recognised by MNAzyme 1a was a synthetic DNA oligonucleotide homologous to the human microRNA miR-20 RNA sequence. It had the following sequence:

```
D-20 target (MNAzyme 1a target):
TAAAGTGCTTATAGTGCAGGTA          SEQ ID NO: 47
```

11.7 Assembly Facilitator for MNAzyme 4a.

The assembly facilitator F4 required for MNAzyme 4a formation was a synthetic DNA oligonucleotide with the following sequence:

```
Assembly Facilitator F4 for MNAzyme 4a:
                                SEQ ID NO: 48
CGACGACCACTCCGACGACAGTCCTATAGTGAGTGCTACAG
```

11.8 Reaction Conditions

All reactions were performed in a single SmartCycler® SmartCap tube (Cepheid), as described below. The MNAzyme 1a cleavage, the DNAzyme 2a ligation and the SCUD MNAzyme 3a cascade amplification (aspects (i), (ii) and (iii), respectively) were performed concurrently in an initial single reaction volume of 15 via isothermal incubation on the SmartCycler® thermal cycler system (Cepheid) at 40° C. for 2 hours. The reaction contained 200 nM preSub5, 100 nM preSub3, 100 nM of DNAzyme ligase 7Z81-10/10, partzymes for MNAzyme 1a (50 nM miR20A2/1 and 300 nM miR20B3/1), 20 nM of partzymes for MNAzyme 3a (Partzyme A 4SYNTA2/1i-10HP and Partzyme B 4SYNTB3/1i-12HP), 150 mM NaCl, 2 mM KCl, 50 mM Tris HCl (pH 9.0 at 25° C.) and 50 mM MgCl$_2$ and either 100 nM of D-20 target, or 100 pM of D-20 target, or 100 fM of D-20 target, or no target (dH$_2$O only control).

Control reactions lacked the SCUD MNAzyme 3a partzyme components and as such underwent aspects (i), (ii) and (iv) only. These reactions contained 200 nM preSub5, 100 nM preSub3, 100 nM of DNAzyme ligase 7Z81-10/10, partzymes for MNAzyme 1a (50 nM miR20A2/1 and 300 nM miR20B3/1), 150 mM NaCl, 2 mM KCl, 50 mM Tris HCl (pH 9.0 at 25° C.) and 50 mM MgCl$_2$ and either 100 nM of D-20 target, or 100 pM of D-20 target, or 100 fM of D-20 target, or no target (dH$_2$O only control).

Following incubation of the SCUD and control reactions, a 10 µl aliquot of detection reagents were added to the Smart-Cap System tube to give final concentrations of 300 nM of partzyme STB5/2(21), 100 nM of the assembly facilitator F4 for MNAzyme 4a, 150 mM NaCl, 2 mM KCl, 50 mM Tris HCl (pH 9.0 at 25° C.), 50 mM MgCl$_2$ and 100 nM of the substrate SubBi-2-FB in a total reaction volume of 25 Reactions were thermocycled for 90 cycles from 55° C. to 80° C. (55° C. for 80 seconds, 80° C. for 20 seconds) and fluorescence was monitored at 55° C. on the SmartCycler® (Cepheid).

The increase in fluorescence due to cleavage of MNAzyme substrate C (SubBi-2-FB) was monitored over time for the SCUD and control reactions. A threshold level of fluorescence was set at 100 units of fluorescence and the amount of time for each reaction to attain the threshold fluorescence level was measured.

11.9 Results

The fluorescence was measured during the thermocycling phase (aspect (iv)), which followed the initial isothermal phase (including aspects (i) and (ii) for control reactions and aspects (i), (ii) and (iii) for reactions including the SCUD amplification cascade). In the reaction containing the SCUD cascade components and 100 nM of target, the threshold fluorescence was attained within one cycle and the reaction reached a plateau at 10 cycles (Table 4). In the reaction containing the SCUD cascade components and 100 pM of target, the threshold fluorescence was reached at the 19$^{th}$ cycle and the reaction had still not reached a plateau after 80 cycles. In the reaction containing the SCUD cascade components and 100 fM of target, the threshold fluorescence was reached at 18 cycles and the reaction had still not reached a plateau after 80 cycles.

In contrast the reaction containing the SCUD cascade components but lacking target failed to reach a threshold value after 80 cycles of thermocycling. As such, the attainment of threshold fluorescence was indicative of the presence of target nucleic acid in these reactions.

TABLE 4

| Time to reach threshold fluorescence. | | |
|---|---|---|
| Initial concentration | SCUD | Control |
| 100 nM | 1 cycle | 1 cycle |
| 100 pM | 19 cycles | 59 cycles |
| 100 fM | 18 cycles | NS |
| No target | NS | NS |

Time (minutes) taken to reach threshold of 100 units
(NS—no signal above threshold)

In the control reactions, which lacked the SCUD cascade components, but contained 100 nM of target, the threshold fluorescence was attained within one cycle and the reaction reached a plateau at 34 cycles (Table 4). In the control reaction containing 100 pM of target, the threshold fluorescence was reached at 59 cycles and the reaction had still not reached a plateau after 80 cycles. In the control reaction containing 100 fM of target, the threshold fluorescence was not reached after 80 cycles. Similarly, the control reaction which lacked target failed to reach a threshold value after 80 cycles. As such, the attainment of threshold fluorescence was indicative of the presence of target nucleic acid in these reactions. The observations above are consistent with the following enzymatic amplification steps in the reactions containing all components for aspects (i), (ii), (iii) and (iv) (FIG. 11). Firstly, MNAzyme 1a cleaves substrate A in the presence of F1 specific target (D-20) producing two fragments (Aa and Ab) (aspect (i)). The Aa fragment was the 5' fragment (CTGTAG-CACTCACTAua) (SEQ ID NO:49) that had a 2',3'-cyclic phosphate terminus. Secondly, the Ab product functions as a activator assembly facilitator component, which directs the formation of active MNAzyme 3a. MNAzyme 3a cleaves substrate A generating two products Aa and Ab. The product Ab can then function as a facilitator, which directs the formation of more active MNAzyme 3a. Thus the MNAzyme 3a system results in a SCUD autocatalytic self replicating feedback amplification cascade (aspect (iii)). This SCUD cascade also results in further accumulation of Aa, which can function as a substrate for DNAzyme 2a. Thirdly, the 5' fragment Aa ligates to a second ligase substrate B present in the reaction mix and this results in the formation of a new oligonucleotide (ligation product Aa/B) with the sequence of CTGTAG-CACTCACTAuagGAACAACGAGAGGAAACCTT (SEQ ID NO:50) (where upper case represent DNA bases and lower case represent RNA bases) (aspect (ii)). This ligation product in turn functions as a partzyme component for MNAzyme 4a. Finally, this newly created partzyme associates with a second partzyme (STB5/2(21)) and an F4 assembly facilitator to create MNAzyme 4a (aspect (iv)). MNAzyme 4a then cleaves MNAzyme substrate C (SubBi-2-FB) resulting in separation of a fluorophore and quencher dye pair thus causing an increase in fluorescence.

In the control reactions containing only components for aspects (i), (ii) and (iv) (FIG. 11) the observations above are consistent with the following events. Firstly, MNAzyme 1a cleaves MNAzyme substrate A in the presence of F1 specific target (D-20) producing two fragments (Aa and Ab) (aspect (i)). The Aa fragment is the 5' fragment (CTGTAGCACT-CACTAua) (SEQ ID NO:49) that had a 2',3'-cyclic phosphate terminus. The 5' fragment Aa ligates to a second ligase substrate B present in the reaction mix and this results in the formation of a new oligonucleotide (ligation product (Aa/B) (aspect (ii)). This ligation product in turn functions as a partzyme component for MNAzyme 4a. Finally, this newly created partzyme associates with a second partzyme (STB5/2(21)) and an F4 assembly facilitator to create MNAzyme 4a (aspect (iv)). MNAzyme 4a then cleaves MNAzyme substrate C (SubBi-2-FB) resulting in separation of a fluorophore quencher dye pair thus causing an increase in fluorescence.

The reactions that lacked target demonstrate that the development of a fluorescence signal in reactions, which either contained or lacked the SCUD MNAzyme components, was dependent on the presence of target nucleic acid. In reactions that contained SCUD MNAzyme components but which lacked target, no facilitator fragment Ab was formed and hence the intact substrate A bound to the partzymes for MNAzyme 3a and formed an MNAi complex. FIG. 9 shows schematic representation of the structures formed by the SCUD MNA complexes, namely the active MNAzyme 3a (panel A structure a) and MNAi (panel A structure b). The MNAzyme requires an assembly facilitator (F1 in panel A structure a in FIG. 9); or activator assembly facilitator (Ab in FIG. 11 aspect (iii)), which can be generated by cleavage of a substrate. The intact substrate can bind to the MNAi structure and function as an activity inhibitor (I) as shown in FIG. 9 panel A structure b. The partzymes used in this experiment to create MNAzyme 3a had sensor arms with regions of self complementarity at the termini of both partzymes. The assembly facilitator binds in the regions between the region of complementarity (FIG. 9 panel A structure a and FIG. 11 (iii) MNAzyme 3a).

Comparison of the limits of detection of reactions which either contained or lacked the SCUD MNAzyme components demonstrate that the presence of the SCUD components results in amplification of the signal which allows detection of lower amounts of target. Reactions which lacked the SCUD MNAzyme 3a partzyme components had a limit of detection of $1 \times 10^9$ molecules (100 pM starting concentration). In comparison the reaction containing the SCUD components were able to detect $1 \times 10^6$ molecules (100 fM starting concentration). Further, a signal above threshold was detected for $1 \times 10^9$ molecules after 19 cycles in the reaction containing SCUD components compared to 59 cycles for reactions lacking SCUD partzyme components for MNAzyme 3a. As such, the presence of the SCUD components (partzymes for MNAzyme 3a) in conjunction with an initiating MNAzyme (1a) was capable of generating the activator assembly facilitator component Ab thus lowering both the time for detection and the limit of detection. The mechanism relies on feedback with each SCUD MNAzyme 3a generating more facilitators for more MNAzyme 3a providing a mechanism for signal amplification (aspect (iii) FIG. 11). This SCUD signal amplification method allows signal amplification by a mechanism which relies solely on the catalytic activity of nucleic acid enzymes and not on protein enzymes such as those used in other nucleic acid target amplification methods such as the PCR. Further the SCUD amplification occurred isothermally during the first phase of the experiment where reagents were incubated at 40° C. In conclusion SCUD is capable of autocatalytic self replication causing signal amplification under isothermal conditions. SCUD allows increased sensitivity and speed of detection in a format which does not require protein enzymes.

Example 12

A Full Adder Using MNA Complexes

MNA complexes, including MNAzymes, can be exploited to develop molecular full adders. One exemplary design schema for how a full adder based on MNAzymes could be constructed is presented in FIG. 12.

A full adder receives input on three channels (A, B, C), and produces output on two channels (X, Y) based on the input, according to the following table, Table 5;

| Input A | Input B | Input C | Output X | Output Y |
|---------|---------|---------|----------|----------|
| On      |         |         | On       |          |
|         | On      |         | On       |          |
|         |         | On      | On       |          |
| On      | On      |         |          | On       |
| On      |         | On      |          | On       |
|         | On      | On      |          | On       |
| On      | On      | On      | On       | On       |

For clarity, missing (or "off") signals are denoted by an empty cell in the table. In summary, output X is on in the presence of either exactly one or all three inputs, and output Y is on in the presence of two or three inputs. Whereas a full adder is normally implemented in circuit logic using electrical signals as input and output, the system can be implemented using biological processes, with the inputs represented by detectable events, and the outputs represented either by detectable events or detectable effects.

As can be seen from the table, in addition to the null case (no inputs), there are 7 possible combinations of inputs. Three of these are the case where there is exactly one input present (represented by the logic NANDNAND), three are the case where there are two inputs present (represented by the logic AND) and one where all three inputs are present (represented by the logic ANDAND).

In one system depicted in FIG. 12, these seven logic gates are designed for use in a single test tube whereby any combination of inputs added to the tube will produce an expected result (for example, fluorescence). The gates are all constructed separately before addition to the reaction vessel. In FIG. 12, the black oligonucleotides have been pre-complexed before the gates are pooled, and comprise the actual gates, the blue and green substrates represent substrates with different fluorophores attached, and comprise the two output signals, and the FAC ('facilitator') molecules constitute the inputs. The partzymes of each gate will each be comprised of unique sequence, except where both reporter and sensor arms bind the same substrate and FAC or C oligonucleotide. In these cases, the same partzyme can be used in the construction of two separate gates, such as the B partzymes of AND gates 2 and 3, the B partzymes of NANDNAND gates 2 and 3, and the B partzymes of NANDNAND gate 1 and the ANDAND gate shown in FIG. 12. The FAC1 and FAC2 oligonucleotides act as assembly facilitators, while FAC3 acts as an arm stabilizer, however in this schema, all FAC oligonucleotides serve the same purpose, which is to activate/inactivate logic gates. The 'C' oligonucleotides (C1, C2, C3) are complementary to their corresponding FAC oligonucleotides and have been pre-complexed with the partzymes. When added to the reaction vessel, the FACs will peel off their complementary C oligonucleotides via a branch migration process, inactivating the gates which contain the complementary C oligonucleotide. This process is made possible by elongating the C oligonucleotides and their corresponding FAC oligonucleotides, in order to provide free sequence where branch migration can be initiated.

With this design, addition of any one and only one FAC will provide a first fluorescent colour (in this example, as shown in FIG. 12, a 'blue' fluorescence), any combination of 2 FACs will produce a second fluorescent colour ('green' fluorescence in FIG. 12), and when all three FACs are introduced to the reaction vessel, both fluorescent colours will be produced ('blue' and 'green' in FIG. 12).

The following explanation is provided with reference to FIG. 12. If, for example, no FAC molecule is present, all complexes will remain inactive as not all components required for each complex to become active are available. There will be no fluorescence.

For example, if FAC1 only is an input:
  FAC1 activates the first NANDNAND gate in FIG. 12 when it binds with the pre-complexed partzymes, the C2 and C3 oligonucleotides, and the substrate, producing blue fluorescence. It also peels off the C1 oligonucleotide of the $2^{nd}$ and $3^{rd}$ NANDNAND gates, which are in any case inactive because FAC2 and FAC3 are not available to form an active MNAzyme.
  When only FAC1 is available the ANDAND and AND gates are not active as they require other FAC molecules to allow activation.
If, for example, FAC1 and FAC2 are inputs, the following would occur:

The $3^{rd}$ AND gate of FIG. 12 is active as both required oligonucleotides are available to form an active MNAzyme, producing green fluorescence.
The other two AND gates of FIG. 12 will not be activated as they require FAC3.
The ANDAND gate will not be active as only two of the required FAC molecules are available.
FAC1 and FAC2 are available for the complexes of the $1^{st}$ and $2^{nd}$ NANDNAND gates of FIG. 12, respectively. However, FAC1 will peel off its complementary C1 oligonucleotide in the $2^{nd}$ NANDNAND gate of FIG. 12, so that it will not be active. FAC2 will peel off its complementary C2 oligonucleotide in the 1st NANDNAND gate of FIG. 12, so that it will not be active. The third NANDNAND gate is not active because it requires FAC3 (and because C1 and C2 will also be peeled off by FAC1 and FAC2, respectively).
Thus there is no blue fluorescence from any gate.
Only the relevant AND gate provides green fluorescence.
If, for example, all three FAC oligonucleotides are present:
The AND gates, and ANDAND gate are activated, producing green and blue fluorescence, respectively.
The NANDNAND gates will not be activated by virtue of the fact that the 'C' oligonucleotides will be peeled off by their respective FAC oligonucleotide.
One of skill in the art would recognize that such a schema can be applied in an analogous way to any other combination of FAC oligonucleotide or oligonucleotides.

It will be understood by one of skill in the art that output from one full adder can be used as input for another full adder.

REFERENCES

Patents and Patent Publications

PCT International Publication No. WO 99/45146
PCT International Publication No. WO 99/50452
U.S. Pat. No. 6,140,055
U.S. Pat. No. 6,201,113
U.S. Pat. No. 6,365,724

Other References

Achenbach, J., Nutiu, R. and Li, Y. (2005) Structure-switching allosteric deoxyribozymes. Analytica Chimica Acta. 534(1): 41-51.
Barany, F. (1991) Genetic disease detection and DNA amplification using cloned thermostable ligase. PNAS, 88: 189-193.
Benenson, Y., Paz-Elizur, T., Adar, R., Keinan, E., Livneh, Z. and Shapiro, E. (2001) Programmable and autonomous computing machine made of biomolecules. Nature. November 22; 414(6862):430-4
Benenson, Y., Gil, B., Ben-Dor, U., Adar, R. and Shapiro, E. (2004) An autonomous molecular computer for logical control of gene expression. Nature. May 27; 429(6990): 423-9
Beyer, S. and Simmel, F. C (2006) A modular DNA signal translator for the controlled release of a protein by an aptamer. Nucleic Acids Research, 34: 1581-1587
Breaker, R. (1997) DNA enzymes. Nat Biotech. 15: 427-431.
Breaker, R. R. and Joyce, G. F. (1994) A DNA enzyme that cleaves RNA. Chem Biol. December; 1(4): 223-9.
Brown, A., Li, J., Pavot, C. and Lu, Y. (2003) A lead-dependent DNAzyme with a two-step mechanism. Biochem. June 17; 42(23): 7152-61.

Cairns, M., King, A. and Sun, L. (2000) Nucleic acid mutation analysis using catalytic DNA. Nucl Acids Res. 28(3): e9.

Cairns, M., King, A. and Sun, L. (2003) Optimisation of the 10-23 DNAzyme-substrate pairing interactions enhanced RNA cleavage activity at purine-cytosine target sites. Nucl Acids Res. June 1; 31(11): 2883-9.

Carmi, N., Shultz, L. A. and Breaker, R. R. (1996) In vitro selection of self-cleaving DNAs. Chem Biol. 3(12): 1039-46.

Cox, J. C. and Ellington, A. D. (2001) DNA computation function. Curr Biol. May 1; 11(9):R336.

Cruz, R. P., Withers, J. B. and Li, Y. (2004) Dinucleotide junction cleavage versatility of 8-17 deoxyribozyme. Chem Biol. January; 11(1): 57-67.

Cuenoud, B. and Szostak, J. W. (1995) A DNA metalloenzyme with DNA ligase activity. Nature. 375(6532): 611-4.

Elghanian, R., Storhoff, J., Mucic, R., Letsinger, R. and Mirkin, C. (1997) Selective colorimetric detection of polynucleotides based on the distance-dependent optical properties of gold nanoparticles. Science. 277: 1078-1079.

Emilsson, G. M. and Breaker, R. R. (2002) Deoxyribozymes: new activities and new applications. Cell. Mol. Life Sci. 59, 596-607.

Haseloff, J. and Gerlach, W. L. (1988) Simple RNA enzymes with new and highly specific endoribonuclease activities. Nature. August 18; 334(6183): 585-91.

Huizenga, D. and Szostak, J. (1995) A DNA aptamer that binds adenosine and ATP. Biochemistry. 34: 656-665

Illangasekare, M., Sanchez, G., Nickles, T. and Yarus, M. (1995) Aminoacyl-RNA synthesis catalyzed by an RNA. Science. 267(5198): 643-7.

Lee, J. F., Hesselberth, J. R., Meyers, L. A. and Ellington, A. D. (2004) Aptamer Database. Nucl Acids Res. 32(90001): D95-100.

Li, Y. and Sen, D. (1996) A catalytic DNA for porphyrin metallation [letter]. Nat Struct Biol. 3(9): 743-7.

Liu, J. and Lu, Y. (2004) Adenosine-dependent assembly of aptazyme-functionalized gold nanoparticles and its application as a colorimetric biosensor. Analytical Chemistry. 76: 1627-1632.

Lohse, P. A. and Szostak, J. W. (1996) Ribozyme-catalysed amino-acid transfer reactions. Nature. 381(6581): 442-4.

Mirkin, C., Letsinger, R., Mucic, R. and Storhoff, J. (1996) A DNA-based method for rationally assembling nanoparticles into macroscopic materials. Nature. 382: 607-609.

Paul, N. and Joyce, G. (2004) Minimal self-replicating systems. Current Opinion in Chemical Biology. 8(6): 634-639.

Perreault, J., Labuda, D., Usman, N., Yang, J. and Cedergren, R. (1991) Relationship between 2'-hydroxyls and magnesium binding in the hammerhead RNA domain: a model for ribozyme catalysis. Biochemistry. 30(16): 4020-5.

Perreault, J., Wu, T., Cousineau, B., Ogilvie, K. and Cedergren, R. (1990) Mixed deoxyribo- and ribo-oligonucleotides with catalytic activity. Nature. 344(6266): 565-7.

Prior, T. K., Semlow, D. R. Flynn-Charlebois, Rashid, I. And Silverman, S. K. (2004) Structure-function correlations derived from faster variants of a RNA ligase deoxyribozyme. Nucleic Acids Research, 32, 1075-1082.

Raillard, S. A. and Joyce, G. F. (1996) Targeting sites within HIV-1 cDNA with a DNA-cleaving ribozyme. Biochemistry. 35(36): 11693-701.

Sando, S., Sasaki, T., Kanatani, K. and Aoyama, Y. (2003) Amplified Nucleic Acid Sensing Using Programmed Self-Cleaving DNAzyme. J. Am. Chem. Soc.; (Communication); 125(51); 15720-15721

Santoro, S. and Joyce, G. (1997) A general purpose RNA cleaving DNA enzyme. Proc Natl Acad Sci USA. 94: 4262-4266.

Santoro, S. W. and Joyce, G. F. (1998) Mechanism and utility of an RNA-cleaving DNA enzyme. Biochem. 37(38): 13330-42.

Schubert, S., Furste, J., Werk, D., Grunert, H., Zeichhardt, H., Erdmann, V. and Kurreck, J. (2004) Gaining target access for deoxyribozymes. J Mol Biol. May 28; 339(2): 355-63.

Schweitzer, B. and Kingsmore, S. (2001) Combining nucleic acid amplification and detection. Current Opinion in Biotechnology, 12: 21-27.

Sidorov, A., Grasby, J. and Williams, D. (2004) Sequence-specific cleavage of RNA in the absence of divalent metal ions by a DNAzyme incorporating imidazolyl and amino functionalities. Nucl Acids Res. March 5; 32(4): 1591-601.

Silverman, S. (2004) Breaking up is easy to do (if you're a DNA enzyme that cleaves RNA). Chem Biol. January; 11(1): 7-8.

Stojanovic, M. N. and Stefanovic, D. (2003) A Deoxyribozyme-Based Molecular Automaton. Nature Biotechnology 21, 1069-1074

Tabor, J. J., Levy, M. and Ellington, A. D. (2006) Deoxyribozymes that recode sequence information. Nucleic Acids Res. 34(8): 2166-2172

Tarasow, T. M., Tarasow, S. L. and Eaton, B. E. (1997) RNA-catalysed carbon-carbon bond formation. Nature. 389(6646): 54-7.

Todd, A. V., Fuery, C. J., Impey, H. L., Applegate, T. L. and Haughton, M. A. (2000) DzyNA-PCR: Use of DNAzymes to detect and quantify nucleic acid in a fluorescent real time format. Clinical Chemistry 46:5 625-630.

Warashina, M., Kuwabara, T., Nakamatsu, Y. and Taira, K. (1999) Extremely high and specific activity of DNA enzymes in cells with a Philadelphia chromosome. Chem Biol. April; 6(6): 237-50.

Zaborowska, Z., Furste, J., Erdmann, V. and Kurreck, J. (2002) Sequence requirements in the catalytic core of the "10-23" DNA enzyme. J Biol Chem. 277(43): 240617-22.

The invention claimed is:

1. A multi-component nucleic acid inhibited proenzyme (MNAi) comprising at least two or more component oligonucleotides, a first assembly facilitator component comprising at least one nucleic acid, and at least one activity inhibitor oligonucleotide, wherein at least a first component oligonucleotide and a second component oligonucleotide are capable of self-assembly when hybridized to the at least one activity inhibitor oligonucleotide, wherein each of said at least first and said second component oligonucleotides comprises a substrate arm portion, a catalytic core portion, and a sensor arm portion, wherein each catalytic core portion is flanked by a substrate arm and by a sensor arm, wherein the catalytic core portions are of a DNAzyme, and wherein upon self-assembly, the sensor arm portions of said first and second component oligonucleotides act as sensor arms, the substrate arm portions of the first and second component oligonucleotides act as substrate arms by hybridizing to a substrate nucleic acid, and the catalytic core portions of the first and second component oligonucleotides form a catalytic core; and wherein said activity inhibitor oligonucleotide comprises a first domain comprising a second assembly facilitator component that hybridizes with at least one of said sensor arms and a second domain that does not hybridize to said sensor arms, wherein the first and second assembly facilitator components can hybridize to one or more of the sensor arms forming a junction between the first and second assembly facilitator components, wherein upon self-assembly said first and second component oligonucleotides are maintained in proximity for association of their respective catalytic core portions to form a complete catalytic core inhibited by disruption of secondary structure at said junction by the second domain of the activity inhibitor oligonucleotide, and wherein the catalytic core can be active only after separation of the second domain of the activity inhibitor oligonucleotide from the first domain of the activity inhibitor oligonucleotide.

2. The MNAi of claim 1 wherein at least one component of the MNAi comprises an aptamer or portion thereof wherein said aptamer or portion thereof binds a ligand selected from the group comprising proteins, glycoproteins, lipids, lipoproteins, cells, viruses, bacteria, archaea, fungi, antibodies, metabolites, pathogens, toxins, contaminants, poisons, small molecules, polymers, metal ions, metal salts, prions or any derivatives, portions or combinations thereof.

3. The MNAi of claim 1, wherein modification of the activity inhibitor can provide a detectable effect.

4. The MNAi of claim 1, wherein the activity inhibitor oligonucleotide can be displaced by an activator oligonucleotide component.

5. The MNAi of claim 4, wherein the activator is an assembly facilitator.

6. The MNAi of claim 5, wherein the first assembly facilitator is a target.

7. The MNAi of claim 6, wherein the target is to be detected, identified or quantitated.

8. The MNAi of claim 1, further comprising a substrate of the DNAzyme.

9. The MNAi of claim 8, wherein the substrate comprises a detectable moiety and a quencher.

10. The MNAi of claim 1, wherein the activity inhibitor oligonucleotide comprises a site cleavable by a catalytic nucleic acid.

11. The MNAi of claim 1, wherein the activity inhibitor oligonucleotide can be removed or displaced.

12. The MNAi of claim 11, wherein the activity inhibitor oligonucleotide can be removed by a modulator oligonucleotide which functions by branch chain migration.

* * * * *

SEQUENCE LISTING

```
<160> NUMBER OF SEQ ID NOS: 51

<210> SEQ ID NO 1
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
```

<222> LOCATION: (38)
<223> OTHER INFORMATION: Phosphorylated thymine

<400> SEQUENCE: 1
actggatgtc catctgtctg acaacgagag gaaaccctt          38

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)
<223> OTHER INFORMATION: Phosphorylated cytosine

<400> SEQUENCE: 2
tgcccaggga ggctagctta tac          23

<210> SEQ ID NO 3
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (15)
<223> OTHER INFORMATION: Phosphorylated guanine

<400> SEQUENCE: 3
cttcgtgagg gtgag          15

<210> SEQ ID NO 4
<211> LENGTH: 22
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 4
aaggtttcct cguccctggg ca          22

<210> SEQ ID NO 5
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
tgccccctca ccctcacgaa ggtatacaga cagatggaca tccagttggt ga          52

<210> SEQ ID NO 6
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

```
<221> NAME/KEY: modified_base
<222> LOCATION: (40)
<223> OTHER INFORMATION: Phosphorylated thymine

<400> SEQUENCE: 6
caaacgagtc ctggccttgt ctacaacgag aggaaacctt                                40

<210> SEQ ID NO 7
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (47)
<223> OTHER INFORMATION: Phosphorylated cytosine

<400> SEQUENCE: 7
tgcccaggga ggctagctgt ggagacggat tacaccttcc cacttgc                        47

<210> SEQ ID NO 8
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
gcaagtggga aggtgtaatc cgtctccaca gacaaggcca ggactcgttt g                   51

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
gcaagtggga aggtgtaatc cgtct                                                25

<210> SEQ ID NO 10
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
ccacagacaa ggccaggact cgtttg                                               26

<210> SEQ ID NO 11
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
aaggtttcct cgtccctggg caccacagac aaggccagga ctcgtttg                       48

<210> SEQ ID NO 12
```

```
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
aacgtacact gcacgcggtc gaaatagtga gtacctgggg gagtattgcg gaggaaggt      59

<210> SEQ ID NO 13
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
catctcttct ccgagcgtct gtaccgtgta c                                   31

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
gtacacggta cagaccgtgc agtgtacgtt                                     30

<210> SEQ ID NO 15
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
ccaggtactc actatt                                                    16

<210> SEQ ID NO 16
<211> LENGTH: 20
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 16
actcactata ggaagagatg                                                20

<210> SEQ ID NO 17
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
caaacgagtc ctggccttgt ctacaacgag aggaaacctt                          40
```

```
<210> SEQ ID NO 18
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
tgcccaggga ggctagctct gtccgaggcg tgat                                    34

<210> SEQ ID NO 19
<211> LENGTH: 11
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 19
atcacgcctc g                                                             11

<210> SEQ ID NO 20
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
gacagagaca aggccaggac tcgtttg                                            27

<210> SEQ ID NO 21
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 21
atcacgcctc gutcctccca g                                                  21

<210> SEQ ID NO 22
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
caaacgagtc ctggccttgt ctacaacgag aggcgtgat                               39

<210> SEQ ID NO 23
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 23
ctgggaggaa ggctagctct gtccgaggaa accttcgtcg tccagactgc g    51

<210> SEQ ID NO 24
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
cgcagtctgg acgacg    16

<210> SEQ ID NO 25
<211> LENGTH: 12
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 25
aaggtttcct cg    12

<210> SEQ ID NO 26
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
caaacgagtc ctggccttcg agtacaacga gaggaaacct t    41

<210> SEQ ID NO 27
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
tgcccaggga ggctagcgaa acctt    25

<210> SEQ ID NO 28
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
aaggccagga ctcgtttg    18

<210> SEQ ID NO 29
<211> LENGTH: 25
<212> TYPE: DNA
<213> ORGANISM: Artificial Sequence
<220> FEATURE:

<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 29
gggaaggtgt aataaggttt cctcg                                           25

<210> SEQ ID NO 30
<211> LENGTH: 35
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 30
gggaaggtgt aataaggttt cctcguccct gggca                                35

<210> SEQ ID NO 31
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31 attacaccttt ccc                                                       13

<210> SEQ ID NO 32
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (38)
<223> OTHER INFORMATION: Phosphorylated cytosine

<400> SEQUENCE: 32
tgcccaggga ggctagcgtg gagacggatt acaccttc                             38

<210> SEQ ID NO 33
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
gtatcgtgtg ttcttgccct cgtgcccaca acgagaggcg tgat                      44

<210> SEQ ID NO 34
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
ctgggaggaa ggctagctag ggacgcactc ctacctcta                              39

<210> SEQ ID NO 35
<211> LENGTH: 29
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 35
aaggtttcct cguccctggg cacacgagg                                        29

<210> SEQ ID NO 36
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
gcaagaacac acgatac                                                     17

<210> SEQ ID NO 37
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
tagaggtagg agtgcg                                                      16

<210> SEQ ID NO 38
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
gaaggtgtaa tccgtctcca cagacaaggc caggactcgt ttg                        43

<210> SEQ ID NO 39
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
cctctcgttg acggcggagt gattgggagg ttagctctag tgagtgc                    47

<210> SEQ ID NO 40
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 40
tacctgcact acggtcgaaa tagtgagt                                              28

<210> SEQ ID NO 41
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
catctcttct ccgagctaag cacttta                                               27

<210> SEQ ID NO 42
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
tgcccaggga ggctagctct gtcgtcggag tggtcgtcg                                  39

<210> SEQ ID NO 43
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
ggatgggcac taacgtgccc atcccatctc cggtcgaaat agtgagt                         47

<210> SEQ ID NO 44
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
catctcttct ccgagcttcc catctcacga cgataacgtc gtgagatg                        48

<210> SEQ ID NO 45
<211> LENGTH: 27
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 45
ctgtagcact cactauagga agagatg                                               27

<210> SEQ ID NO 46
<211> LENGTH: 21
<212> TYPE: DNA
<213> ORGANISM: Artificial Sequence
<220> FEATURE:
```

```
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 46
ggaacaacga gaggaaacct t                                              21

<210> SEQ ID NO 47
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
taaagtgctt atagtgcagg ta                                             22

<210> SEQ ID NO 48
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
cgacgaccac tccgacgaca gtcctatagt gagtgctaca g                        41

<210> SEQ ID NO 49
<211> LENGTH: 17
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 49
ctgtagcact cactaua                                                   17

<210> SEQ ID NO 50
<211> LENGTH: 38
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 50
ctgtagcact cactauagga acaacgagag gaaaccctt                           38

<210> SEQ ID NO 51
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (41)
```

```
<223> OTHER INFORMATION: Phosphorylated thymine

<400> SEQUENCE: 51
caaacgagtc ctggccttgt cttacaacga gaggaaacct t                         41
```